US009611462B2

(12) United States Patent
Ang et al.

(10) Patent No.: US 9,611,462 B2
(45) Date of Patent: Apr. 4, 2017

(54) ENDOGLUCANASE 1B (EG1B) VARIANTS

(71) Applicant: Codexis, Inc., Redwood City, CA (US)

(72) Inventors: Ee Lui Ang, Singapore (SG); Ellen D. Eberhard, Fallbrook, CA (US); Xiyun Zhang, Fremont, CA (US); Wei Zhang, Singapore (SG); Jing Tian, Singapore (SG); Derek J. Smith, Singapore (SG); Vesna Mitchell, San Jose, CA (US)

(73) Assignee: Codexis, Inc., Redwood City, CA (US)

( * ) Notice: Subject to any disclaimer, the term of this patent is extended or adjusted under 35 U.S.C. 154(b) by 341 days.

(21) Appl. No.: 14/366,761

(22) PCT Filed: Dec. 18, 2012

(86) PCT No.: PCT/US2012/070236
§ 371 (c)(1),
(2) Date: Jun. 19, 2014

(87) PCT Pub. No.: WO2013/096244
PCT Pub. Date: Jun. 27, 2013

(65) Prior Publication Data
US 2014/0370552 A1    Dec. 18, 2014

Related U.S. Application Data

(60) Provisional application No. 61/577,804, filed on Dec. 20, 2011.

(51) Int. Cl.
*C12N 9/42* (2006.01)
*C12P 19/14* (2006.01)
*C12P 19/02* (2006.01)

(52) U.S. Cl.
CPC ............ *C12N 9/2437* (2013.01); *C12P 19/02* (2013.01); *C12P 19/14* (2013.01); *C12Y 302/01004* (2013.01)

(58) Field of Classification Search
None
See application file for complete search history.

(56) References Cited

U.S. PATENT DOCUMENTS

| | | |
|---|---|---|
| 3,990,944 A | 11/1976 | Gauss et al. |
| 3,990,945 A | 11/1976 | Huff et al. |
| 4,356,196 A | 10/1982 | Hultquist |
| 4,461,648 A | 7/1984 | Foody |
| 4,486,553 A | 12/1984 | Wesch |
| 4,556,430 A | 12/1985 | Converse et al. |
| 4,600,590 A | 7/1986 | Dale |
| 5,037,663 A | 8/1991 | Dale |
| 5,171,592 A | 12/1992 | Holtzapple et al. |
| 5,605,793 A | 2/1997 | Stemmer |
| 5,811,238 A | 9/1998 | Stemmer et al. |
| 5,811,381 A | 9/1998 | Emalfarb et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 5,939,544 A | 8/1999 | Karstens et al. |
| 6,015,707 A | 1/2000 | Emalfarb et al. |
| 6,090,595 A | 7/2000 | Foody et al. |
| 6,096,548 A | 8/2000 | Stemmer |
| 6,106,888 A | 8/2000 | Dale et al. |
| 6,117,679 A | 9/2000 | Stemmer |
| 6,132,970 A | 10/2000 | Stemmer |
| 6,165,793 A | 12/2000 | Stemmer |
| 6,176,176 B1 | 1/2001 | Dale et al. |
| 6,180,406 B1 | 1/2001 | Stemmer |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |

(Continued)

FOREIGN PATENT DOCUMENTS

| | | |
|---|---|---|
| EP | 0137280 B1 | 3/1992 |
| WO | 95/22625 A1 | 8/1995 |

(Continued)

OTHER PUBLICATIONS

Berka, R.M., et al., 2011, "Comparative genomic analysis of the thermophilic biomass-degrading fungi *Myceliophthora thermophila* and *Thielavia terrestris*", Nature Biotechnology, vol. 29, No. 10, pp. 922-927.*

UniProtKB/TrEMBL accession No. G2R8K6_THITE Thelavia terrestris strain ATCC 38088 / NRRL 8126 amino acid sequence supplied as an Appendix to the Office communication.*

Altschul, S.F., et al., "Gapped BLAST and PSI-BLAST: a new generation of protein database search programs," Nucleic Acids Res., 25(17):3389-3402 [1997].

Blaiseau, P.-L., et al., "Primary structure of a chitinase-encoding gene (chi1) from the filamentous fungus *Aphanocladium album*: similarity to bacterial chitinases," Gene, 120(2):243-248 [1992].

Boel, E., et al., "Two different types of intervening sequences in the glucoamylase gene from *Aspergillus niger*," EMBO J., 3(7):1581-1585 [1984].

(Continued)

*Primary Examiner* — Nashaat Nashed
*Assistant Examiner* — William W Moore
(74) *Attorney, Agent, or Firm* — Codexis, Inc.

(57) ABSTRACT

The present invention provides endoglucanase 1b (EG1b) variants suitable for use in saccharification reactions. The present application further provides genetically modified fungal organisms that produce EG1b variants, as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures.

13 Claims, No Drawings

(56) References Cited

U.S. PATENT DOCUMENTS

| | | |
|---|---|---|
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,573,086 B1 | 6/2003 | Emalfrab et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,946,296 B2 | 9/2005 | Patten et al. |
| 6,961,664 B2 | 11/2005 | Selfinov et al. |
| 6,995,017 B1 | 2/2006 | Stemmer |
| 7,024,312 B1 | 4/2006 | Selfinov et al. |
| 7,058,515 B1 | 6/2006 | Selfinov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,399,627 B2 | 7/2008 | Emalfarb et al. |
| 7,419,809 B2 | 9/2008 | Foody et al. |
| 7,421,347 B2 | 9/2008 | Selfinov et al. |
| 7,430,477 B2 | 9/2008 | Selfinov et al. |
| 7,465,791 B1 | 12/2008 | Hallberg et al. |
| 7,534,564 B2 | 5/2009 | Patten et al. |
| 7,620,500 B2 | 11/2009 | Mundorff et al. |
| 7,620,502 B2 | 11/2009 | Selfinov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,754,457 B2 | 7/2010 | Foody et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selfinov et al. |
| 7,868,138 B2 | 1/2011 | Stemmer et al. |
| 7,873,499 B2 | 1/2011 | Selfinov et al. |
| 7,904,249 B2 | 3/2011 | Selfinov et al. |
| 7,957,912 B2 | 6/2011 | Selfinov et al. |
| 2007/0031953 A1 | 2/2007 | Dunson, Jr. et al. |
| 2007/0238155 A1 | 10/2007 | Gusakov et al. |
| 2008/0057541 A1 | 3/2008 | Hill et al. |
| 2008/0104724 A1 | 5/2008 | Sticklen et al. |
| 2008/0194005 A1 | 8/2008 | Emalfarb et al. |
| 2008/0220990 A1 | 9/2008 | Fox |
| 2008/0299613 A1* | 12/2008 | Merino ............... C07K 14/37 435/69.1 |
| 2009/0061484 A1 | 3/2009 | Scott et al. |
| 2009/0099079 A1 | 4/2009 | Emalfarb et al. |
| 2009/0123979 A1* | 5/2009 | Xu ............... C12P 7/10 435/101 |
| 2009/0209009 A1 | 8/2009 | Tolan et al. |
| 2009/0312196 A1 | 12/2009 | Colbeck et al. |
| 2009/0328259 A1* | 12/2009 | Harris ............... C07K 14/5431 800/298 |
| 2010/0267089 A1 | 10/2010 | Yang et al. |
| 2014/0234907 A1* | 8/2014 | Zhang ............... C12N 9/2437 435/72 |

FOREIGN PATENT DOCUMENTS

| | | |
|---|---|---|
| WO | 96/00787 A1 | 1/1996 |
| WO | 97/00078 A1 | 1/1997 |
| WO | 97/35966 A1 | 10/1997 |
| WO | 98/12307 A1 | 3/1998 |
| WO | 98/15633 A1 | 4/1998 |
| WO | 98/27230 A1 | 6/1998 |
| WO | 98/31821 A2 | 7/1998 |
| WO | 00/42651 A1 | 7/2000 |
| WO | 01/75767 A2 | 10/2001 |
| WO | 2007/075899 A2 | 7/2007 |
| WO | 2007/115201 A2 | 10/2007 |
| WO | 2008/073914 A2 | 6/2008 |
| WO | 2009/033071 A2 | 3/2009 |
| WO | 2009/045651 A2 | 4/2009 |
| WO | 2009/085859 A2 | 7/2009 |
| WO | 2009/085935 A2 | 7/2009 |
| WO | 2009/152336 A1 | 12/2009 |
| WO | 2010/022511 A1 | 3/2010 |
| WO | 2010/107303 A2 | 9/2010 |
| WO | 2010/107644 A2 | 9/2010 |

OTHER PUBLICATIONS

Botstein, D., et al., "Strategies and Applications ofin Vitro Mutagenesis," Science, 229(4719):1193-1201 [1985].

Brigham, J.S., et al., "Hemicellulases: Diversity and Applications," in Handbook on Bioethanol (C. Wyman ed.) pp. 119-141, Taylor and Francis, Washington DC, (1995).

Carter, P., "Site-directed mutagenesis," Biochem. J., 237:1-7 [1986].

Case, M.E, et al., "Efficient transformation of Neurospora crassa by utilizing hybrid plasmid DNA," Proc. Natl. Acad. Sci. USA, 76(10):5259-5263 [1979].

Cho, Y., et al., "A high throughput targeted gene disruption method for Alternaria brassicicola functional genomics using linear minimal element (LME) constructs," Mol Plant Microbe Interact,19(1):7-15 [2006].

Christians, F.C., et al. "Directed evolution of thymidine kinase for AZT phosphorylation using DNA family shuffling," Nat. Biotechnol., 17:259-264 [1999].

Combier, J.-P., et al., "Agrobacterium tumefaciens-mediated transformation as a tool for insertional mutagenesis in the symbiotic ectomycorrhizal fungus *Hebeloma cylindrosporum*," FEMS Microbiol Lett., 220:141-8 [2003].

Crameri A., et al., "DNA shuffling of a family of genes from diverse species accelerates directed evolution," Nature, 391:288-291 [1998].

Crameri, A., et al., "Improved green fluorescent protein by molecular evolution using DNA shuffling," Nat. Biotechnol., 14:315-319 [1996].

Crameri, A., et al., "Molecular evolution of an arsenate detoxification pathway by DNA shuffling," Nat. Biotechnol., 15:436-438 [1997].

(56) References Cited

OTHER PUBLICATIONS

Dale, S.J., et al., "Oligonucleotide-Directed Random Mutagenesis Using the Phosphorothioate Method," Meth. Mol. Biol., 57:369-74 [1996].
Dayhoff, M.O. et al., In Atlas of Protein Sequence and Structure, "A model of evolutionary change in proteins," vol. 5, Suppl. 3, Natl. Biomed. Res. Round, Washington D.C. [1978], pp. 345-352.
Drissen, R.E.T., et al., "Modelling ethanol production from cellulose: separate hydrolysis and fermentation versus simultaneous saccharification and fermentation," Biocat. Biotransform., 27:27-35 [2009].
Firon, A., et al., "Identification of Essential Genes in the Human Fungal Pathogen Aspergillus fumigatus by Transposon Mutagenesis," Eukaryot. Cell, 2(2):247-55 [2003].
Foreman P.K., et al., "Transcriptional Regulation of Biomass-degrading Enzymes in the Filamentous Fungus *Trichoderma reesei*," J. Biol. Chem., 278(34):31988-31997 [2003].
Garg. A.K., "An addition to the genus *Chrysosporium corda*," Mycopathologia, 30(3-4):221-224 [1966].
Glenn, J.K., et al., "Mn(II) Oxidation Is the Principal Function of the Extracellular Mn-Peroxidase from Phanerochaete chrysosporium," Arch. Biochem. Biophys., 251(2):688-696 [1986].
Guo, Z., et al., "3'-End-Forming Signals of Yeast mRNA," Mol. Cell. Biol., 15(11):5983-5990 [1995].
Harris, P.V., et al., "Stimulation of Lignocellulosic Biomass Hydrolysis by Proteins of Glycoside Hydrolase Family 61: Structure and Function of a Large, Enigmatic Family," Biochem., 49:3305-3316 [2010].
Harvey, P.J., et al., "Veratryl alcohol as a mediator and the role of radical cations in lignin biodegradation by Phanerochaete chrysosporium," FEBS Lett., 195(1,2):242-246 [1986].
Henikoff, S., et al., "Amino acid substitution matrices from protein blocks," Proc. Natl. Acad. Sci. USA, 89:10915-10919 [1992].
Hong, J., et al., "Cloning and functional expression of thermostable beta-glucosidase gene from Thermoascus aurantiacus," Appl. Microbiol. Biotechnol, 73:1331-1339 [2007].
Johnstone, I.L., et al., "Cloning an Aspergillus nidulans developmental gene by transformation," EMBO J.,4(5):1307-1311 [1985].
Kelly, J.M., et al., "Transformation of Asoergillus niger by the amdS gene of Aspergillus nidulans," EMBO J., 4(2):475-479 [1985].
Kinsey, J.A., et al., "Transformation of Neurospora crassa with the Cloned am (Glutamate Dehydrogenase) Gene," Mol. Cell. Biol., 4:117-122 [1984].
Kramer, B., et al., "Different base/base mismatches are corrected with different efficiencies by the methyl-directed DNA mismatch-repair system of *E. coli*," Cell, 38:879-887 [1984].
Limon, C., et al., "Primary structure and expression pattern of the 33-kDa chitinase gene from the nucoparasitic fungus *Trichocherma harzianum*," Curr. Genet., 28:478-83 [1995].
Ling, M.M., et al., "Approaches to DNA Mutagenesis: An Overview," Anal. Biochem., 254(2):157-78 [1997].
Mahadevan S.A. , et al, "Site-directed mutagenesis and CBM engineerng of Cel5A (Thermotoga maritima)", FEMS Microbiology Letters, 287:205-211 [2008].
Maruyama, J., "Multiple gene disruptions by marker recycling with highly efficient gene-targeting background (delta-ligD) in Aspergillus oryzae," Biotechnol Lett., 30:1811-1817 [2008].
McCleary, B.V., et al., "Measurement of resistant starch by enzymatic digestion in starch and selected plant materials: collaborative study," J. AOAC Int'l., 85(5):1103-11 [2002].
Minshull, J., et al., "Protein evolution by molecular breeding," Curr. Op. Chem. Biol., 3:284-290 [1999].
Nunberg, J.H., et al., "Molecular Cloning and Characterization of the Glucoamylase Gene of Aspergillus awamori," Mol. Cell Biol., 4(11):2306-2315 [1984].
Parry, N.J., et al., "Biochemical characterization and mechanism of action of a thermostable beta-glucosidase purified from Thermoascus aurantiacus," Biochem. J., 353:117-127[2001].
Porath, J., "Immobilized metal ion affinity chromatography," Protein Expression and Purification, 3:263-281 [1992].
Romanos, M.A., et al., "Foreign gene expression in yeast: a review," Yeast 8:423-488 [1992].
Rothstein, R.J., "One-step gene disruption in Yeast," Meth. Enzymol., 101:202-211 [1983].
Rotsaert, F.A.J., et al., "Site-directed mutagenesis of the heme axial ligands in the hemoflavoenzyme cellobiose dehydrogenase," Arch. Biochem. Biophys., 390(2):206-14 [2001].
Saloheimo, M., et al., "Swollenin, a Trichoderma reesei protein with sequence similarity to the plant expansins, exhibits disruption activity on cellulosic materials," Eur. J. Biochem., 269:4202-4211 [2002].
Sheir-Neiss, G., et al., "Characterization of the secreted cellulases of Trichoderma reesei wild type and mutants during controlled fermentations," Appl. Microbial. Biotechnol., 20:46-53 [1984].
Simonen, M., et al., "Protein Secretion in *Bacillus* Species," Microbiological Reviews, 57:109-137 [1993].
Smith, M., "In Vitro Mutagenesis," Ann. Rev. Genet., 19:423-462 [1985].
Stemmer, W.P.C. "DNA shuffling by random fragmentation and reassembly: In vitro recombination for molecular evolution," Proc. Nat. Acad. Sci. USA, 91:10747-10751 [1994].
Stemmer, W.P.C., "Rapid evolution of a protein in vitro by DNA shuffling," Nature, 370:389-391 [1994].
Takahashi, T., et al., "Efficient gene disruption in the koji-mold *Aspergillus sojae* using a novel variation of the positive-negative method," Mel. Gen. Genom., 272: 344-352 [2004].
Taussig, R., et al., "Nucleotide sequence of the yeast SUC2 gene for invertase," Nucl. Acids Res., 11(6):1943-54 [1983].
Tilburn, J., et al., "Transformation by integration in Aspergillus nidulans," Gene 26:205-221 [1983].
Trinder, P., "Determination of Glucose in Blood Using Glucose Oxidase with an Alternative Oxygen Acceptor," Ann. Clin. Biochem., 6:24-27 [1969].
Viikari, L., et al., "Thermostable enzymes in lignocellulose hydrolysis," Adv. Biochem. Eng. Biotechnol., 108:121-45 [2007].
Weil, J., et al., "Pretreatment of Yellow Poplar Sawdust by Pressure Cooking in Water," Appl. Biochem. Biotechnol., 68(1-2): 21-40 [1997].
Wells, J.A., et al., "Cassette mutagenesis: an efficient method for generation of multiple mutations at defined sites," Gene, 34:315-323 [1985].
Wilson, I.A., et al., "The structure of antigenic determinant in a protein," Cell, 37:767-778 [1984].
Yelton, M.M., et al., "Transformation of Aspergillus nidulans by using a trpC plasmid," Proc. Natl. Acad. Sci. USA, 81:1480-1474 [1984].
You, B., et al., "Gene-specifc disruption in the fillamentous fungus *Cercospora nicotianae* using a split-marker approach," Arch Micriobiol., 191:615-622 [2009].
Zhang, J.-H., et al., "Directed evolution of a fucosidase from a galactosidase by DNA shuffling and screening" Proc. Nat. Acad. Sci. U.S.A., 94:4504-4509 [1997].
GenBank Accession No. AEO58196.1 dated Jul. 23, 2012.
GenBank Accession No. AEO67421.1 dated Sep. 2, 2014.
SwissProt Accession No. P00724 dated Feb. 22, 2012.

* cited by examiner

SEQUENCE LISTING

```
<160> NUMBER OF SEQ ID NOS: 9

<210> SEQ ID NO 1
<211> LENGTH: 1395
<212> TYPE: DNA
<213> ORGANISM: Myceliophthora thermophila

<400> SEQUENCE: 1
atggggcaga agactctcca ggggctggtg gcggcggcgg cactggcagc ctcggtggcg      60
aacgcgcagc aaccgggcac cttcacgccc gaggtgcatc cgacgctgcc gacgtggaag     120
tgcacgacga gcggcgggtg cgtccagcag gacacgtcgg tggtgctcga ctggaactac     180
cgctggttcc acaccgagga cggtagcaag tcgtgcatca cctctagcgg cgtcgaccgg     240
accctgtgcc cggacgaggc gacgtgcgcc aagaactgct tcgtcgaggg cgtcaactac     300
acgagcagcg gggtcgagac gtccggcagc tccctcaccc tccgccagtt cttcaagggc     360
tccgacggcg ccatcaacag cgtctccccg cgcgtctacc tgctcggggg agacggcaac     420
tatgtcgtgc tcaagctcct cggccaggag ctgagcttcg acgtggacgt atcgtcgctc     480
ccgtgcggcg agaacgcggc cctgtacctg tccgagatgg acgcgacggg aggacggaac     540
gagtacaaca cgggcggggc cgagtacggg tcgggctact gtgacgccca gtgccccgtg     600
cagaactgga acaacggac gctcaacacg ggccgggtgg gctcgtgctg caacgagatg     660
```

-continued

```
gacatcctcg aggccaactc caaggccgag gccttcacgc cgcacccctg catcggcaac      720
tcgtgcgaca agagcgggtg cggcttcaac gcgtacgcgc gcggttacca caactactgg      780
gcccccggcg gcacgctcga cacgtcccgg cctttcacca tgatcacccg cttcgtcacc      840
gacgacggca ccacctcggg caagctcgcc cgcatcgagc gcgtctacgt ccaggacggc      900
aagaaggtgc ccagcgcggc gcccgggggg gacgtcatca cggccgacgg gtgcacctcc      960
gcgcagccct acgcggcct ttccggcatg ggcgacgccc tcggccgcgg catggtcctg      1020
gccctgagca tctggaacga cgcgtccggg tacatgaact ggctcgacgc cggcagcaac      1080 ggccctgca gcgacaccga gggtaacccg tccaacatcc tggccaacca cccggacgcc      1140
cacgtcgtgc tctccaacat ccgctggggc gacatcggct ccaccgtcga caccggcgat      1200
ggcgacaaca acggcggcgg ccccaacccg tcatccacca ccaccgctac cgctaccacc      1260
acctcctccg gcccggccga gcctacccag acccactacg gccagtgtgg agggaaagga      1320
tggacgggcc ctaccgctg cgagacgccc tacacctgca agtaccagaa cgactggtac      1380
tcgcagtgcc tgtag                                                        1395
```

<210> SEQ ID NO 2
<211> LENGTH: 464
<212> TYPE: PRT
<213> ORGANISM: Myceliophthora thermophila

<400> SEQUENCE: 2

```
Met Gly Gln Lys Thr Leu Gln Gly Leu Val Ala Ala Ala Ala Leu Ala
1               5                   10                  15

Ala Ser Val Ala Asn Ala Gln Gln Pro Gly Thr Phe Thr Pro Glu Val
            20                  25                  30

His Pro Thr Leu Pro Thr Trp Lys Cys Thr Thr Ser Gly Gly Cys Val
        35                  40                  45

Gln Gln Asp Thr Ser Val Val Leu Asp Trp Asn Tyr Arg Trp Phe His
    50                  55                  60

Thr Glu Asp Gly Ser Lys Ser Cys Ile Thr Ser Ser Gly Val Asp Arg
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Glu Thr Ser Gly Ser Ser Leu
            100                 105                 110

Thr Leu Arg Gln Phe Phe Lys Gly Ser Asp Gly Ala Ile Asn Ser Val
        115                 120                 125

Ser Pro Arg Val Tyr Leu Leu Gly Asp Gly Asn Tyr Val Val Leu
    130                 135                 140

Lys Leu Leu Gly Gln Glu Leu Ser Phe Asp Val Asp Val Ser Ser Leu
145                 150                 155                 160

Pro Cys Gly Glu Asn Ala Ala Leu Tyr Leu Ser Glu Met Asp Ala Thr
                165                 170                 175

Gly Gly Arg Asn Glu Tyr Asn Thr Gly Gly Ala Glu Tyr Gly Ser Gly
            180                 185                 190

Tyr Cys Asp Ala Gln Cys Pro Val Gln Asn Trp Asn Asn Gly Thr Leu
        195                 200                 205

Asn Thr Gly Arg Val Gly Ser Cys Cys Asn Glu Met Asp Ile Leu Glu
    210                 215                 220

Ala Asn Ser Lys Ala Glu Ala Phe Thr Pro His Pro Cys Ile Gly Asn
225                 230                 235                 240
```

```
Ser Cys Asp Lys Ser Gly Cys Gly Phe Asn Ala Tyr Ala Arg Gly Tyr
                245                 250                 255

His Asn Tyr Trp Ala Pro Gly Gly Thr Leu Asp Ser Arg Pro Phe
            260                 265                 270

Thr Met Ile Thr Arg Phe Val Thr Asp Asp Gly Thr Thr Ser Gly Lys
        275                 280                 285

Leu Ala Arg Ile Glu Arg Val Tyr Val Gln Asp Gly Lys Lys Val Pro
        290                 295                 300

Ser Ala Ala Pro Gly Gly Asp Val Ile Thr Ala Asp Gly Cys Thr Ser
305                 310                 315                 320

Ala Gln Pro Tyr Gly Gly Leu Ser Gly Met Gly Asp Ala Leu Gly Arg
                325                 330                 335

Gly Met Val Leu Ala Leu Ser Ile Trp Asn Asp Ala Ser Gly Tyr Met
            340                 345                 350

Asn Trp Leu Asp Ala Gly Ser Asn Gly Pro Cys Ser Asp Thr Glu Gly
        355                 360                 365

Asn Pro Ser Asn Ile Leu Ala Asn His Pro Asp Ala His Val Val Leu
        370                 375                 380

Ser Asn Ile Arg Trp Gly Asp Ile Gly Ser Thr Val Asp Thr Gly Asp
385                 390                 395                 400

Gly Asp Asn Asn Gly Gly Gly Pro Asn Pro Ser Ser Thr Thr Thr Ala
                405                 410                 415

Thr Ala Thr Thr Thr Ser Ser Gly Pro Ala Glu Pro Thr Gln Thr His
            420                 425                 430

Tyr Gly Gln Cys Gly Gly Lys Gly Trp Thr Gly Pro Thr Arg Cys Glu
        435                 440                 445

Thr Pro Tyr Thr Cys Lys Tyr Gln Asn Asp Trp Tyr Ser Gln Cys Leu
        450                 455                 460

<210> SEQ ID NO 3
<211> LENGTH: 441
<212> TYPE: PRT
<213> ORGANISM: Myceliophthora thermophila

<400> SEQUENCE: 3

Gln Pro Gly Thr Phe Thr Pro Glu Val His Pro Thr Leu Pro Thr Trp
1               5                   10                  15

Lys Cys Thr Thr Ser Gly Gly Cys Val Gln Gln Asp Thr Ser Val Val
            20                  25                  30

Leu Asp Trp Asn Tyr Arg Trp Phe His Thr Glu Asp Gly Ser Lys Ser
        35                  40                  45

Cys Ile Thr Ser Ser Gly Val Asp Arg Thr Leu Cys Pro Asp Glu Ala
    50                  55                  60

Thr Cys Ala Lys Asn Cys Phe Val Glu Gly Val Asn Tyr Thr Ser Ser
65                  70                  75                  80

Gly Val Glu Thr Ser Gly Ser Ser Leu Thr Leu Arg Gln Phe Phe Lys
                85                  90                  95

Gly Ser Asp Gly Ala Ile Asn Ser Val Ser Pro Arg Val Tyr Leu Leu
            100                 105                 110

Gly Gly Asp Gly Asn Tyr Val Val Leu Lys Leu Leu Gly Gln Glu Leu
        115                 120                 125

Ser Phe Asp Val Asp Val Ser Ser Leu Pro Cys Gly Glu Asn Ala Ala
    130                 135                 140

Leu Tyr Leu Ser Glu Met Asp Ala Thr Gly Gly Arg Asn Glu Tyr Asn
```

```
                145                 150                 155                 160
        Thr Gly Gly Ala Glu Tyr Gly Ser Gly Tyr Cys Asp Ala Gln Cys Pro
                        165                 170                 175
        Val Gln Asn Trp Asn Asn Gly Thr Leu Asn Thr Gly Arg Val Gly Ser
                        180                 185                 190
        Cys Cys Asn Glu Met Asp Ile Leu Glu Ala Asn Ser Lys Ala Glu Ala
                        195                 200                 205
        Phe Thr Pro His Pro Cys Ile Gly Asn Ser Cys Asp Lys Ser Gly Cys
                210                 215                 220
        Gly Phe Asn Ala Tyr Ala Arg Gly Tyr His Asn Tyr Trp Ala Pro Gly
        225                 230                 235                 240
        Gly Thr Leu Asp Thr Ser Arg Pro Phe Thr Met Ile Thr Arg Phe Val
                        245                 250                 255
        Thr Asp Asp Gly Thr Thr Ser Gly Lys Leu Ala Arg Ile Glu Arg Val
                        260                 265                 270
        Tyr Val Gln Asp Gly Lys Lys Val Pro Ser Ala Ala Pro Gly Gly Asp
                        275                 280                 285
        Val Ile Thr Ala Asp Gly Cys Thr Ser Ala Gln Pro Tyr Gly Gly Leu
                290                 295                 300
        Ser Gly Met Gly Asp Ala Leu Gly Arg Gly Met Val Leu Ala Leu Ser
        305                 310                 315                 320
        Ile Trp Asn Asp Ala Ser Gly Tyr Met Asn Trp Leu Asp Ala Gly Ser
                        325                 330                 335
        Asn Gly Pro Cys Ser Asp Thr Glu Gly Asn Pro Ser Asn Ile Leu Ala
                        340                 345                 350
        Asn His Pro Asp Ala His Val Val Leu Ser Asn Ile Arg Trp Gly Asp
                        355                 360                 365
        Ile Gly Ser Thr Val Asp Thr Gly Asp Gly Asp Asn Asn Gly Gly Gly
                        370                 375                 380
        Pro Asn Pro Ser Ser Thr Thr Thr Ala Thr Ala Thr Thr Thr Ser Ser
        385                 390                 395                 400
        Gly Pro Ala Glu Pro Thr Gln Thr His Tyr Gly Gln Cys Gly Gly Lys
                        405                 410                 415
        Gly Trp Thr Gly Pro Thr Arg Cys Glu Thr Pro Tyr Thr Cys Lys Tyr
                        420                 425                 430
        Gln Asn Asp Trp Tyr Ser Gln Cys Leu
                        435                 440

<210> SEQ ID NO 4
<211> LENGTH: 1395
<212> TYPE: DNA
<213> ORGANISM: Artificial Sequence
<220> FEATURE:
<223> OTHER INFORMATION: Synthetic polynucleotide from round 2 of
      evolution

<400> SEQUENCE: 4
atggggcaga agactctcca ggggctggtg gcggcggcgg cactggcagc ctcggtggcg     60
aacgcgcagc aaccgggcac cttcacgccc gaggtgcatc cgacgctgcc gacgtggaag    120
tgcacgacga cgccggggtg cgtccagcag gacacgtcgg tggtgctcga ctggaactac    180 cgctggatte acaccgagga cggtagcaag tcgtgcatca cctctagcgg cgtcgaccgg    240
accctgtgcc cggacgaggc gacgtgcgcc aagaactgct tcgtcgaggg cgtcaactac    300
acgagcagcg gggtcgagac gtccggcagc tccctcaccc tccgccagtt cttcaagggc    360
```

```
tccgacggcg ccatcaacag cgtctccccg cgcgtctacc tgctcggggg agacggcaac    420
tatgtcgtgc tcaagctcct cggccaggag ctgagcttcg acgtggacgt atcgtcgctc    480
ccgtgcggcg agaacgcggc cctgtacctg tccgagatgg acgcgacggg aggacggaac    540
gagtacaaca cgggcggggc cgagtacggg tcgggctact gtgacgccca gtgccccgtg    600
cagaactgga acaacgggac gctcaacacg ggccgggtgg gctcgtgctg caacgagatg    660
gacatcctcg aggccaactc caaggccgag gccttcacgc cgcacccctg catcggcaac    720
tcgtgcgaca agagcgggtg cggcttcaac gcgtacgcgc gcggttacca caactactgg    780 gccccggcg gcacgctcga cacgtccgg cctttcacca tgatcacccg cttcgtcacc    840
gacgacggca ccacctcggg caagctcgcc cgcatcgagc gcgtctacgt ccaggacggc    900
aagaaggtgc ccagcgcggc gcccgggggg gacgtcatca cggccgacgg gtgcacctcc    960
gcgcagccct acggcggcct ttccggcatg ggcgacgccc tcggccgcgg catggtcctg   1020
gccctgagca tctggaacga cgcgtccggg tacatgaact ggctcgacgc cggcagcaac   1080 ggccctgca gcgacaccga gggtaacccg tccaacatcc tggccaacca cccggacgcc   1140
cacgtcgtgc tctccaacat ccgctggggc gacatcggct ccaccgtcga caccggcgat   1200
ggcgacaaca acgcggcgg ccccaacccg tcatccacca ccaccgctac cgctaccacc   1260
acctcctccg gcccggccga gcctacccag acccactacg ccagtgtgg agggaaagga   1320 tggacgggcc ctacccgctg cgagacgccc tacacctgca gtaccagaa cgactggtac   1380 tcgcagtgcc tgtag                                                   1395
```

<210> SEQ ID NO 5
<211> LENGTH: 464
<212> TYPE: PRT
<213> ORGANISM: Artificial Sequence
<220> FEATURE:
<223> OTHER INFORMATION: Synthetic polypeptide from round 2 of evolution

<400> SEQUENCE: 5

```
Met Gly Gln Lys Thr Leu Gln Gly Leu Val Ala Ala Ala Leu Ala
1               5                   10                  15

Ala Ser Val Ala Asn Ala Gln Gln Pro Gly Thr Phe Thr Pro Glu Val
            20                  25                  30

His Pro Thr Leu Pro Thr Trp Lys Cys Thr Thr Ser Gly Gly Cys Val
        35                  40                  45

Gln Gln Asp Thr Ser Val Val Leu Asp Trp Asn Tyr Arg Trp Ile His
    50                  55                  60

Thr Glu Asp Gly Ser Lys Ser Cys Ile Thr Ser Ser Gly Val Asp Arg
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Glu Thr Ser Gly Ser Ser Leu
            100                 105                 110

Thr Leu Arg Gln Phe Phe Lys Gly Ser Asp Gly Ala Ile Asn Ser Val
        115                 120                 125

Ser Pro Arg Val Tyr Leu Leu Gly Gly Asp Gly Asn Tyr Val Val Leu
    130                 135                 140

Lys Leu Leu Gly Gln Glu Leu Ser Phe Asp Val Asp Val Ser Ser Leu
145                 150                 155                 160

Pro Cys Gly Glu Asn Ala Ala Leu Tyr Leu Ser Glu Met Asp Ala Thr
                165                 170                 175
```

Gly Gly Arg Asn Glu Tyr Asn Thr Gly Gly Ala Glu Tyr Gly Ser Gly
            180                 185                 190

Tyr Cys Asp Ala Gln Cys Pro Val Gln Asn Trp Asn Asn Gly Thr Leu
        195                 200                 205

Asn Thr Gly Arg Val Gly Ser Cys Cys Asn Glu Met Asp Ile Leu Glu
    210                 215                 220

Ala Asn Ser Lys Ala Glu Ala Phe Thr Pro His Pro Cys Ile Gly Asn
225                 230                 235                 240

Ser Cys Asp Lys Ser Gly Cys Gly Phe Asn Ala Tyr Ala Arg Gly Tyr
                245                 250                 255

His Asn Tyr Trp Ala Pro Gly Gly Thr Leu Asp Thr Ser Arg Pro Phe
            260                 265                 270

Thr Met Ile Thr Arg Phe Val Thr Asp Asp Gly Thr Thr Ser Gly Lys
        275                 280                 285

Leu Ala Arg Ile Glu Arg Val Tyr Val Gln Asp Gly Lys Lys Val Pro
    290                 295                 300

Ser Ala Ala Pro Gly Gly Asp Val Ile Thr Ala Asp Gly Cys Thr Ser
305                 310                 315                 320

Ala Gln Pro Tyr Gly Gly Leu Ser Gly Met Gly Asp Ala Leu Gly Arg
                325                 330                 335

Gly Met Val Leu Ala Leu Ser Ile Trp Asn Asp Ala Ser Gly Tyr Met
            340                 345                 350

Asn Trp Leu Asp Ala Gly Ser Asn Gly Pro Cys Ser Asp Thr Glu Gly
        355                 360                 365

Asn Pro Ser Asn Ile Leu Ala Asn His Pro Asp Ala His Val Val Leu
    370                 375                 380

Ser Asn Ile Arg Trp Gly Asp Ile Gly Ser Thr Val Asp Thr Gly Asp
385                 390                 395                 400

Gly Asp Asn Asn Gly Gly Gly Pro Asn Pro Ser Ser Thr Thr Thr Ala
                405                 410                 415

Thr Ala Thr Thr Thr Ser Ser Gly Pro Ala Glu Pro Thr Gln Thr His
            420                 425                 430

Tyr Gly Gln Cys Gly Gly Lys Gly Trp Thr Gly Pro Thr Arg Cys Glu
        435                 440                 445

Thr Pro Tyr Thr Cys Lys Tyr Gln Asn Asp Trp Tyr Ser Gln Cys Leu
    450                 455                 460

<210> SEQ ID NO 6
<211> LENGTH: 1395
<212> TYPE: DNA
<213> ORGANISM: Artificial Sequence
<220> FEATURE:
<223> OTHER INFORMATION: Synthetic polynucleotide from round 3 of
      evolution

<400> SEQUENCE: 6
atggggcaga agactctcca ggggctggtg gcggcggcgg cactggcagc ctcggtggcg      60
aacgcgcagc aaccgggcac cttcacgccc gaggtgcatc cgacgctgcc gacgtggaag     120
tgcacgacga gcggcgggtg cgtccagcag gacacgtcgg tggtgctcga ctggaactac     180
cgctggattc acacccgtga cggtagcaag tcgtgcatca cctctagcgg cgtcgaccgg     240
accctgtgcc cggacgaggc gacgtgcgcc aagaactgct tcgtcgaggg cgtcaactac     300
acgagcagcg gggtcgagac gtccggcagc tccctcaccc tccgccagtt cttcaagggc     360
tccgacggcg ccatcaacag cgtctccccg cgcgtctacc tgctcggggg agacggcaac     420

```
tatgtcgtgc tcaagctcct cggccaggag ctgagcttcg acgtggacgt atcgtcgctc      480
ccgtgcggcg agaacgcggc cctgtacctg tccgagatgg acgcgacggg aggacggaac      540
gagtacaaca cgggcggggc cgagtacggg tcgggctact gtgacgccca gtgccccgtg      600
atgaactgga acaacgggac gctcaacacg ggccgggtgg gctcgtgctg cagcgagatg      660
gacatcctcg aggccaactc ctttgccgag gccttcacgc cgcacccctg catcggcaac      720
tcgtgcgaca gagcgggtg cggcttcaac gcgtacgcgc gcggttacca caactactgg      780
gcccccggcg gcacgctcga cacgtcccgg cctttcaccg tgatcacccg cttcgtcacc      840
gacgacggca ccacctcggg caagctcgcc cgcatcgagc gcgtctacgt ccaggacggc      900
aagaaggtgc ccagcgcggc gcccggggg gacgtcatca cggccgacgg gtgcacctcc       960
gcgcagccct acggcggcct ttccggcatg ggcgacgccc tcggccgcgg catggtcctg     1020
gccctgagca tctggaacga cgcgtccacc tacatgaact ggctcgacgc cggcagcaac     1080
ggccccctgca gcgacaccga gggtaacccg tccaacatcc tggccaacca cccggacgcc     1140
cacgtcgtgc tctccaacat ccgctggggc gacatcggct ccaccgtcga caccggcgat     1200
ggcgacaaca acggcggcgg ccccaacccg tcatccacca ccaccgctac cgctaccacc     1260
acctcctccg gcccggccga gcctacccag acccactacg ccagtgtgg agggaaagga      1320
tggacgggcc ctacccgctg cgagacgccc tacacctgca agtaccagaa cgactggtac     1380
tcgcagtgcc tgtag                                                      1395
```

<210> SEQ ID NO 7
<211> LENGTH: 464
<212> TYPE: PRT
<213> ORGANISM: Artificial Sequence
<220> FEATURE:
<223> OTHER INFORMATION: Synthetic polypeptide from round 3 of evolution

<400> SEQUENCE: 7

```
Met Gly Gln Lys Thr Leu Gln Gly Leu Val Ala Ala Ala Leu Ala
1               5                   10                  15

Ala Ser Val Ala Asn Ala Gln Gln Pro Gly Thr Phe Thr Pro Glu Val
            20                  25                  30

His Pro Thr Leu Pro Thr Trp Lys Cys Thr Thr Ser Gly Gly Cys Val
        35                  40                  45

Gln Gln Asp Thr Ser Val Val Leu Asp Trp Asn Tyr Arg Trp Ile His
    50                  55                  60

Thr Arg Asp Gly Ser Lys Ser Cys Ile Thr Ser Ser Gly Val Asp Arg
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Glu Thr Ser Gly Ser Ser Leu
            100                 105                 110

Thr Leu Arg Gln Phe Phe Lys Gly Ser Asp Gly Ala Ile Asn Ser Val
        115                 120                 125

Ser Pro Arg Val Tyr Leu Leu Gly Asp Gly Asn Tyr Val Val Leu
    130                 135                 140

Lys Leu Leu Gly Gln Glu Leu Ser Phe Asp Val Asp Val Ser Ser Leu
145                 150                 155                 160

Pro Cys Gly Glu Asn Ala Ala Leu Tyr Leu Ser Glu Met Asp Ala Thr
                165                 170                 175

Gly Gly Arg Asn Glu Tyr Asn Thr Gly Gly Ala Glu Tyr Gly Ser Gly
            180                 185                 190
```

-continued

Tyr Cys Asp Ala Gln Cys Pro Val Met Asn Trp Asn Gly Thr Leu
            195                 200                 205

Asn Thr Gly Arg Val Gly Ser Cys Cys Ser Glu Met Asp Ile Leu Glu
    210                 215                 220

Ala Asn Ser Phe Ala Glu Ala Phe Thr Pro His Pro Cys Ile Gly Asn
225                 230                 235                 240

Ser Cys Asp Lys Ser Gly Cys Gly Phe Asn Ala Tyr Ala Arg Gly Tyr
            245                 250                 255

His Asn Tyr Trp Ala Pro Gly Gly Thr Leu Asp Thr Ser Arg Pro Phe
            260                 265                 270

Thr Val Ile Thr Arg Phe Val Thr Asp Asp Gly Thr Thr Ser Gly Lys
            275                 280                 285

Leu Ala Arg Ile Glu Arg Val Tyr Val Gln Asp Gly Lys Lys Val Pro
            290                 295                 300

Ser Ala Ala Pro Gly Gly Asp Val Ile Thr Ala Asp Gly Cys Thr Ser
305                 310                 315                 320

Ala Gln Pro Tyr Gly Gly Leu Ser Gly Met Gly Asp Ala Leu Gly Arg
            325                 330                 335

Gly Met Val Leu Ala Leu Ser Ile Trp Asn Asp Ala Ser Thr Tyr Met
            340                 345                 350

Asn Trp Leu Asp Ala Gly Ser Asn Gly Pro Cys Ser Asp Thr Glu Gly
            355                 360                 365

Asn Pro Ser Asn Ile Leu Ala Asn His Pro Asp Ala His Val Val Leu
            370                 375                 380

Ser Asn Ile Arg Trp Gly Asp Ile Gly Ser Thr Val Asp Thr Gly Asp
385                 390                 395                 400

Gly Asp Asn Asn Gly Gly Pro Asn Pro Ser Ser Thr Thr Thr Ala
            405                 410                 415

Thr Ala Thr Thr Thr Ser Ser Gly Pro Ala Glu Pro Thr Gln Thr His
            420                 425                 430

Tyr Gly Gln Cys Gly Gly Lys Gly Trp Thr Gly Pro Thr Arg Cys Glu
            435                 440                 445

Thr Pro Tyr Thr Cys Lys Tyr Gln Asn Asp Trp Tyr Ser Gln Cys Leu
            450                 455                 460

<210> SEQ ID NO 8
<211> LENGTH: 1395
<212> TYPE: DNA
<213> ORGANISM: Artificial Sequence
<220> FEATURE:
<223> OTHER INFORMATION: Synthetic polynucleotide from round 4 of
      evolution

<400> SEQUENCE: 8
atggggcaga agactctcca ggggctggtg gcggcggcgc aactggcagc ctcggtggcg      60
aacgcgcagc aaccgggcac cttcacgccc gaggtgcatc cgacgctgcc gacgtggaag     120
tgcacgacga gcggcgggtg cgtccagcag gacacgtcgg tggtgctcga ctggaactac     180
cgctggattc acacccgtga cggtagcaag tcgtgcatca cctctagcgg cgtcgaccgg     240
accctgtgcc cggacgaggc gacgtgcgcc aagaactgct cgtcgagggg cgtcaactac     300
acgagcagcg gggtcgagac gtccggcagc tccctcaccc tccgccagtt cttcaagggc     360
tccgacggcg ccatcaacag cgtctccccg cgcgtctacc tgctcgggga gacggcaac     420 tatgtcgtgc tcaagctcct cggccaggag ctgagcttcg acgtggacgt atcgtcgctc     480

```
ccgtgcggcg agaacgcggc cctgtacctg tccgagatgg acgcgacggg aggacggaac      540
gagtacaaca cgggcggggc cgagtacggg tcgggctact gtgacgccca gtgccccgtg      600
atgaactgga acaacgggac gctcaacacg ggccgggtgg gctcgtgctg cagcgagatg      660
gacatcctcg aggccaactc ctttgccgag gccttcacgc cgcacccctg catcggcaac      720
tcgtgcgaca agagcgggtg cggcttcaac gcgtacgcgc gcggttacca caactactgg      780
gcccccggcg gcacgctcga cacgtccggg cctttcaccg tgatcacccg cttcgtcacc      840
gacgacggca ccacctcggg caagctcgcc cgcatcgagc gcgtctacgt ccaggacggc      900
aagaaggtgc ccagcgcggc gcccgggggg gacgtcatca cggccgacgg gtgcacctcc      960
gcgcagccct acggcggcct ttccggcatg ggcgacgccc tcggccgcgg catggtcctg     1020
gccctgagca tctggaacga cgcgtccacc tacatgaact ggctcgacgc cggcagcaac     1080
ggcccctgca gcgacaccga gggtaacccg tccaacatcc tggccaacca cccggacgcc     1140
cacgtcgtgc tctccaacat ccgctggggc gacatcggct ccaccgtcga caccggcgat     1200
ggcgacaaca acgcggcgg ccccaacccg tcatccacca ccaccgctac cgctaccacc     1260
acctcctccg gcccggccga gcctacccag acccactacg gccagtgtgg agggaaagga     1320
tggacgggcc ctacccgctg cgagacgccc tacacctgca gtaccagaa cgactggtac     1380 tcgcagtgcc tgtag                                                       1395
```

<210> SEQ ID NO 9
<211> LENGTH: 464
<212> TYPE: PRT
<213> ORGANISM: Artificial Sequence
<220> FEATURE:
<223> OTHER INFORMATION: Synthetic polypeptide from round 4 of evolution

<400> SEQUENCE: 9

```
Met Gly Gln Lys Thr Leu Gln Gly Leu Val Ala Ala Gln Leu Ala
1               5                   10                  15

Ala Ser Val Ala Asn Ala Gln Gln Pro Gly Thr Phe Thr Pro Glu Val
            20                  25                  30

His Pro Thr Leu Pro Thr Trp Lys Cys Thr Thr Ser Gly Gly Cys Val
        35                  40                  45

Gln Gln Asp Thr Ser Val Val Leu Asp Trp Asn Tyr Arg Trp Ile His
    50                  55                  60

Thr Arg Asp Gly Ser Lys Ser Cys Ile Thr Ser Ser Gly Val Asp Arg
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Glu Thr Ser Gly Ser Ser Leu
            100                 105                 110

Thr Leu Arg Gln Phe Phe Lys Gly Ser Asp Gly Ala Ile Asn Ser Val
        115                 120                 125

Ser Pro Arg Val Tyr Leu Leu Gly Gly Asp Gly Asn Tyr Val Val Leu
    130                 135                 140

Lys Leu Leu Gly Gln Glu Leu Ser Phe Asp Val Asp Val Ser Ser Leu
145                 150                 155                 160

Pro Cys Gly Glu Asn Ala Ala Leu Tyr Leu Ser Glu Met Asp Ala Thr
                165                 170                 175

Gly Gly Arg Asn Glu Tyr Asn Thr Gly Gly Ala Glu Tyr Gly Ser Gly
            180                 185                 190

Tyr Cys Asp Ala Gln Cys Pro Val Met Asn Trp Asn Asn Gly Thr Leu
```

```
              195                 200                 205
Asn Thr Gly Arg Val Gly Ser Cys Cys Ser Glu Met Asp Ile Leu Glu
        210                 215                 220

Ala Asn Ser Phe Ala Glu Ala Phe Thr Pro His Pro Cys Ile Gly Asn
225                 230                 235                 240

Ser Cys Asp Lys Ser Gly Cys Gly Phe Asn Ala Tyr Ala Arg Gly Tyr
                245                 250                 255

His Asn Tyr Trp Ala Pro Gly Gly Thr Leu Asp Thr Ser Arg Pro Phe
            260                 265                 270

Thr Val Ile Thr Arg Phe Val Thr Asp Asp Gly Thr Thr Ser Gly Lys
            275                 280                 285

Leu Ala Arg Ile Glu Arg Val Tyr Val Gln Asp Gly Lys Lys Val Pro
        290                 295                 300

Ser Ala Ala Pro Gly Gly Asp Val Ile Thr Ala Asp Gly Cys Thr Ser
305                 310                 315                 320

Ala Gln Pro Tyr Gly Gly Leu Ser Gly Met Gly Asp Ala Leu Gly Arg
                325                 330                 335

Gly Met Val Leu Ala Leu Ser Ile Trp Asn Asp Ala Ser Thr Tyr Met
            340                 345                 350

Asn Trp Leu Asp Ala Gly Ser Asn Gly Pro Cys Ser Asp Thr Glu Gly
        355                 360                 365

Asn Pro Ser Asn Ile Leu Ala Asn His Pro Asp Ala His Val Val Leu
370                 375                 380

Ser Asn Ile Arg Trp Gly Asp Ile Gly Ser Thr Val Asp Thr Gly Asp
385                 390                 395                 400

Gly Asp Asn Asn Gly Gly Gly Pro Asn Pro Ser Ser Thr Thr Thr Ala
                405                 410                 415

Thr Ala Thr Thr Thr Ser Ser Gly Pro Ala Glu Pro Thr Gln Thr His
            420                 425                 430

Tyr Gly Gln Cys Gly Gly Lys Gly Trp Thr Gly Pro Thr Arg Cys Glu
            435                 440                 445

Thr Pro Tyr Thr Cys Lys Tyr Gln Asn Asp Trp Tyr Ser Gln Cys Leu
450                 455                 460
```

US 9,611,462 B2

ENDOGLUCANASE 1B (EG1B) VARIANTS

CROSS REFERENCE TO RELATED APPLICATIONS

The present application is a national application filed under 35 USC §371 and claims priority to international application to PCT International Application No. PCT/US2012/070236, filed Dec. 18,2012, and U.S. Prov. Appln. Ser. No. 61/577,804, filed on Dec. 20, 2011. The present application hereby incorporates both of these priority applications by reference, in its entireties and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX6-100WO1_ST25.TXT, created on Dec. 18, 2012, 28,496 bytes, machine format IBM-PC, MS-Windows operating system, is hereby incorporated by reference.

FIELD OF THE INVENTION

The present invention provides endoglucanase 1b (EG1b) variants suitable for use in saccharitication reactions. The present application further provides genetically modified fungal organisms that produce EG1b variants, as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures.

BACKGROUND

Interest has arisen in fermentation of carbohydrate-rich biomass to p provide alternatives to petrochemical sources for fuels and organic chemical precursors. There is great interest in using lignocellulosic feedstocks where the plant cellulose is broken down to sugars and subsequently converted to desired end products, such as organic chemical precursors. Lignocellulosic biomass is primarily composed of cellulose, hemicelluloses, and lignin. Cellulose and hemicellulose can be hydrolyzed in a saccharification process to sugars that can be subsequently converted to various products via fermentation. The major fermentable sugars from lignocelluloses are glucose and xylose. For economical ethanol yields, a process that can effectively convert all the major sugars present in cellulosic feedstock would be highly desirable.

SUMMARY OF THE INVENTION

The present invention provides endoglucanase 1b (EG1b) variants suitable for use in saccharification reactions. The present application further provides genetically modified fungal organisms that produce EG1b variants, as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures.

The present invention provides variant endoglucanases and/or biologically active variant endoglucanase fragments comprising (a) an amino acid sequence comprising at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to a wild-type endoglucanase (SEQ ID NO:3); and (b) an amino acid substitution from one or more of the amino acid residues selected from 5, 6, 7, 8, 9, 10, 11, 12, 13, 14, 15, 16, 17, 18, 19, 20, 21, 22, 34, 38, 39, 43, 49, 63, 66, 75, 85, 126, 137, 143, 201, 218, 228, 241, 269, 274, 282, 328, 342, 342, 350, 397, 398, 399, 400, 401, 403, 404, 405, 407, 408, 409, 411, 412, 413, 414, 415, 417, 418, 419, 420, 425, 428, 433, 434, 435, 438, 439, 440, 443, 444, 446, 457, and 464, wherein the residues are numbered with reference to SEQ ID NO:2. In some embodiments, the endoglucanase variants and/or biologically active variant endoglucanase fragments comprise one or more amino acid substitutions selected from T5, L6, Q7, G8, L9, V10, A11. A12, A13. A14, L15, A16, A17, S18, V19, A20, N21, A22, P34, T38, W39, T43, Q49, F63, E66, S75, D85, N126, G137, V143, Q201, N218, K228, S241, S269, M274, D282, S328, L342, L342, G350, D397, T398, G399, D400, G401, N403, N403, N404, G405, G407, P408, P408, N409, S411, S412, T413, T414, T415, T417, T417, A418, T419, T420, P425, P428, Y433, G434, Q435, Q435, G438, K439, G440, G443, P444, R446, N457, and L464, wherein the residues are numbered with reference to SEQ ID NO:2. In some additional embodiments, the endoglucanase variants and/or biologically active variant endoglucanase fragments comprise one or more amino acid substitutions selected from 5L, 5N, 6I, 6K, 6M, 6S, 6T, 7C, 7S, 7T, 7V, 7Y, 8D, 8H, 8I, 8L, 8N, 8Q, 8R, 8S, 8T, 8V, 8Y, 9F, 10M, 11C, 11G, 11I, 11L, 11S, 11T, 11V, 11Y, 12L, 12V, 13C, 13I, 13L, 13M, 13T, 13W, 14I, 14L, 14M, 14Q, 14T, 14V, 15F, 16H, 16I, 16N, 16T, 17C, 17F, 17H, 17N, 17S, 17V, 17W, 17Y, 18C, 18E, 18G, 18I, 18M, 18P, 18Q, 18Y, 19I, 19L, 19T, 20I, 21H, 21K, 22S, 34R, 38A, 39R, 43C, 49R, 63I, 66R, 75P, 85V, 126K, 137T, 143M, 201L, 201M, 218S, 228F, 241K, 269L, 274V, 282G, 328Q, 342F, 342A, 350S, 397Y, 398M, 399C, 400R, 401 D, 403D, 403M, 404L, 405C, 405Y, 405W, 407R, 408E, 408G, 409W, 411A, 412Q, 413E, 413P, 414L, 415G, 417G, 417H, 418C, 418S, 419G, 420G, 420I, 420L, 420K, 425S, 425L, 428C, 428V, 433F, 433V, 434D, 434P, 435G, 435K, 435R, 438A, 439P, 440D, 440R, 440T, 443E, 443S, 444Q, 446G, 457H, and 464Q, wherein the residues are numbered with reference to SEQ ID NO:2. In some further embodiments, the endoglucanase variants and/or biologically active endoglucanase variant fragments comprise one or more amino acid substitutions selected from T5L, T5N, L6I, L6K, L6M, L6S, L6T, Q7C, Q7S, Q7T, Q7V, Q7Y, G8D, G8H, G8I, G8L, G8N, G8Q, G8R, G8S, G8T, G8V, G8Y, L9F, V10M, A11C, A11G, A11I, A11L, A11S, A11T, A11V, A11Y, A12L, A12V, A13C, A13I, A13L, A13M, A13T, A13W, A14I, A14L, A14M, A14Q, A14T, A14V, L15F, A16H, A16I, A16N, A16T, A17C, A17F, A17H, A17N, A17S, A17V, A17W, A17Y, S18C, S18E, S18G, S18I, S18M, S18P, S18Q, S18Y, V19I, V19L, V19T, A20I, N21H, N21K, A22S, P34R, T38A, W39R, T43C, Q49R, F63I, E66R, S75P, D85V, N126K, G137T, V143M, Q201L, Q201M, N218S, K228F, S241K, S269L, M274V, D282G, S328Q, L342F, L342A, G350S, D397Y, T398M, G399C, D400R, D401 D, N403D, N403M, N404L, G405C, G405Y, G405W, G407R, P408E, P408G, N409W, S41 IA, S412Q, T413E, T413P, T414L, T415G, T417G, T417H, A418C, A418S, T419G, T420G, T420I, T420L, T420K, P425S, P425L, P428C, P428V, Y433F, Y433V, G434D, G434P, Q435G, Q435K, Q435R, G438A, K439P, G440D, G440R, G440T, G443E, G443S, P444Q, R446G, N457H, and L464Q, wherein the residues are numbered with reference to SEQ ID NO:2. In some additional embodiments, the endoglucanase variants and/or biologically active endoglucanase variant fragments comprises at least one substitution selected from N403D/M, T419G, P425L, N404L, P428V, L340M, D400R, A418S, G440D, N346D, G401D, Q435G, R446G, and T417G, wherein the residues are numbered with reference to SEQ ID NO:2.

The present invention provides endoglucanase variants and/or biologically active endoglucanase variant fragments comprising polypeptide sequences comprising at least about 60%, at least about 65%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to a polypeptide sequence set forth in any of SEQ ID NOS:5, 7and/or 9. In some embodiments, the variant endoglucanase sequence comprises the sequence set forth in any of SEQ ID NOS:5, 7 and 9. In some embodiments, the variant endoglucanases and/or biologically active variant endoglucanases are endoglucanase 1b (EG1b) variants and/or fragments. In some embodiments, the variant endoglucanase and/or biologically active endoglucanase fragments are *Myceliophthora thermophila* EG1b variants and/or fragments. In some embodiments, the endoglucanase variants and/or biologically active endoglucanase variant fragments have increased thermoactivity at pH about 4-5 and about 65° C. in comparison to wild-type endoglucanase 1b (SEQ ID NO:3). In some additional embodiments, the endoglucanase variants and/or biologically active endoglucanase variant fragments have increased activity on cellulose in comparison to wild-type endoglucanase 1b (SEQ ID NO: 3). The present invention also provides biologically active variant endoglucanase fragments of any of SEQ ID NOS:5, 7 and/or 9.

The present invention provides enzyme compositions comprising at least one endoglucanase variant and/or biologically active endoglucanase variant fragment. In some embodiments, the enzyme compositions further comprise at least one additional enzyme. In some additional embodiments, the enzyme compositions further comprise one or more enzymes selected from cellulases, hemicellulases, xylanases, amylases, glucoamylases, proteases, esterases, lipases, pectinases, and/or arabinases. In some embodiments, the enzyme compositions comprise one or more enzyme(s) selected from endoglucanases (EG), β-glucosidases (BGL), Type 1 cellobiohydrolases (CBH 1), and/or Type 2 cellobiohydrolases (CBH2).

The present invention provides polynucleotides comprising nucleic acid sequences encoding the endoglucanase variants and/or biologically active endoglucanase variant fragments, and/or polynucleotides that hybridize under stringent hybridization conditions to at least one polynucleotide and/or at least one polynucleotide complement that encodes at least one polypeptide comprising at least one amino acid sequence provided herein.

The present invention provides recombinant nucleic acid constructs comprising at least one polynucleotide sequence encoding at least one variant endoglucanase and/or at least one biologically active endoglucanase fragment, wherein the polynucleotide is selected from: (a) a polynucleotide that encodes a polypeptide comprising an amino acid sequence comprising at least about 60%, at least about 65%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89% u, at least about 90%0, at least about 91%, at least about 92%, at least about 93%, at least about 94%, at least about 95%, at least about 96%, at least about 97%, at least about 98%, or at least about 99% identity to SEQ ID NOS:5, 7 and/or 9, wherein the amino acid sequence comprises at least one substitution and/or substitution set provided herein; (b) a polynucleotide that hybridizes under stringent hybridization conditions to at least a fragment of a polynucleotide that encodes a polypeptide comprising the amino acid sequence of SEQ ID NOS: 1, 4, 6, and/or 8, and wherein said amino acid sequence comprises at least one substitution and/or at least one substitution set provided herein; and/or (c) a polynucleotide that hybridizes under stringent hybridization conditions to the complement of at least a fragment of a polynucleotide that encodes a polypeptide comprising the amino acid sequence of SEQ ID NOS: 1, 4, 6, and/or 8, and wherein said amino acid sequence comprises at least one substitution and/or at least one substitution set provided herein. In some embodiments, the polynucleotide sequence comprises at least about 60%, at least about 65%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to SEQ ID NOS: 1, 4, 6, and/or 8, and wherein said polynucleotide sequence comprises at least one mutation and/or at least one mutation set provided herein. In some further embodiments, the polynucleotide sequence is operably linked to a promoter. In some additional embodiments, the promoter is a heterologous promoter. In some yet additional embodiments, the nucleic acid sequence is operably linked to at least one additional regulatory sequence.

The present invention provides recombinant host cells that express at least one polynucleotide sequence encoding at least one endoglucanase variant and/or at least one biologically active endoglucanase variant fragment, such that at least one endoglucanase variant and/or at least one biologically active endoglucanase variant fragment is produced. In some embodiments, the at least one endoglucanase variant and/or biologically active endoglucanase variant fragment is secreted from the host cell. In some embodiments, the host cell further produces at least one enzyme selected from endoglucanases (EG), β-glucosidases (BGL), Type 1 cellobiohydrolases (CBH 1), Type 2cellobiohydrolases (CBH2), and GH61s. In some embodiments, the host cell is a yeast or filamentous fungal cell. In some further embodiments, the tilamentous fungal cell is a *Myceliophthora*, a *Chrysosporium*, a *Thielavia*, a *Trichoderma*, or an

*Aspergillus* cell. In some additional embodiments, the filamentous fungal cell is a *Myceliophthora thermophila*.

The present invention provides methods for producing at least one fermentable sugar from a biomass substrate, comprising contacting the biomass substrate with at least one enzyme composition as provided herein, under culture conditions whereby fermentable sugars are produced.

The present invention also provides methods for producing at least one fermentable sugar from a biomass substrate, wherein the biomass substrate is a feedstock or at least one feedstock, comprising contacting the feedstock with at least one enzyme composition as provided herein, under culture conditions whereby fermentable sugars are produced. In some embodiments, at least one enzyme composition comprises at least one enzyme selected from endoglucanases (EG), β-glucosidases (BGL), Type 1 cellobiohydrolases (CBH1), and Type 2 cellobiohydrolases (CBH2). In some embodiments, the methods further comprise pretreating the biomass substrate and/or feedstock prior to contacting the biomass substrate and/or feedstock with at least one enzyme composition. In some additional embodiments, the biomass substrate and/or feedstock comprises wheat grass, wheat straw, barley straw, sorghum, rice grass, sugarcane, sugar beet, bagasse, switchgrass, corn stover, corn cobs, corn fiber, grains, or a combination thereof. In some yet additional embodiments, the fermentable sugar comprises glucose and/or xylose. In some further embodiments, the methods further comprise recovering at least one fermentable sugar. In yet some additional embodiments, the methods further comprise contacting the at least one fermentable sugar with a microorganism under conditions such that said microorganism produces at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams. In some further embodiments, the fermentation product is an alcohol selected from ethanol and butanol. In some embodiments, the alcohol is ethanol. In some additional embodiments of the methods, the biomass substrate is a cellulosic and/or lignocellulosic feedstock.

The present invention also provides methods for producing an end product from a biomass substrate, comprising: a) contacting the feedstock with at least one composition comprising at least one enzyme, under conditions whereby at least one fermentable sugar is produced from the biomass substrate; and b) contacting the fermentable sugar with a microorganism under conditions such that the microorganism uses the fermentable sugar to produce an end-product. In some embodiments, the present invention provides methods for producing an end product from a feedstock, comprising: a) contacting the feedstock with at least one composition comprising at least one enzyme, under conditions whereby at least one fermentable sugar is produced from the feedstock; and b) contacting the fermentable sugar with a microorganism under conditions such that the microorganism uses the fermentable sugar to produce an end-product. In some embodiments, the composition comprising at least one enzyme comprises wild-type endoglucanase 1b (EG1b) and/or at least one variant endoglucanase 1b (EG1b). In some additional embodiments, the wild-type and/or variant EG1b is an *M. thermophila* EG1b. In some further embodiments, the methods comprise simultaneous saccharification and fermentation reactions (SSF), while in some embodiments the methods comprise separate saccharification and fermentation reactions (SHF). In some additional embodiments, the methods comprise hybrid saccharification and fermentation (HSF), while in still some further embodiments, the methods comprise consolidated bioprocessing (CBP). In some embodiments, the feedstock is a cellulosic and/or lignocellulosic feedstock.

The present invention further provides methods of producing a fermentation end product from a biomass substrate, comprising: a) obtaining at least one fermentable sugar produced according to at least one method set forth herein; and b) contacting the fermentable sugar with a microorganism in a fermentation to produce at least one fermentation end product. The present invention also provides methods of producing a fermentation end product from a feedstock, comprising: a) obtaining at least one fermentable sugar produced according to at least one method set forth herein; and b) contacting the fermentable sugar with a microorganism in a fermentation to produce at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams. In some embodiments, the fermentation end product is at least one alcohol selected from ethanol and butanol. In some embodiments of the methods, the microorganism is selected from eukaryotes and prokaryotes. In some additional embodiments, the microorganism is a yeast, while in some further embodiments, the microorganism is a bacterium. In some embodiments, the microorganism is selected from *Clostridium. Thermoanaerobacter*, and *Bacillus*. In some additional embodiments, the methods further comprise recovering the fermentation end product.

DESCRIPTION OF THE INVENTION

The present invention provides endoglucanase 1b (EG1b) variants suitable for use in saccharification reactions. The present application further provides genetically modified fungal organisms that produce EG1b variants, as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures. In some embodiments, the EG1b is obtained from *Myceliophthora thermophila*.

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the some methods and materials are described herein. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, the term "cellulase" refers to any enzyme that is capable of degrading cellulose. Thus, the term encompasses enzymes capable of hydrolyzing cellulose (β-1,4-glucan or β-D-glucosidic linkages) to shorter cellulose chains, oligosaccharides, cellobiose and/or glucose. "Cellulases" are divided into three sub-categories of enzymes: 1,4-β-D-glucan glucanohydrolase ("endoglucanase" or "EG"); 1,4-β-D-glucan cellobiohydrolase ("exoglucanase," "cellobiohydrolase," or "CBH"); and β-D-glucoside-glucohydrolase ("β-glucosidase," "cellobiase," "BG," or "BGL"). These enzymes act in concert to catalyze the hydrolysis of cellulose-containing substrates. Endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose, β-glucosidases split the cellobiose into glucose monomers.

As used herein, the terms "endoglucanase" and "EG" refer to a category of cellulases (EC 3.2.1.4) that catalyze the hydrolysis of internal β-1,4 glucosidic bonds of cellulose.

As used herein, "EG1" refers to a carbohydrate active enzyme expressed from a nucleic acid sequence coding for a glycohydrolase (GH) Family 7 catalytic domain classified under EC 3.2.1.4 or any protein, polypeptide or catalytically active fragment thereof. In some embodiments, the EG 1 is functionally linked to a carbohydrate binding module (CBM), such as a Family 1 cellulose binding domain.

As used herein, the term "EG1b polypeptide" refers to a polypeptide comprising EG1b activity. In some embodiments, the EG1b polypeptide comprises the sequence set forth in SEQ ID NO:2.

As used herein, the term "EG1b polynucleotide" refers to a polynucleotide encoding a polypeptide comprising EG1b activity.

As used herein, the term "EG1b activity" refers to the enzymatic activity of EG1b (i.e., hydrolyzing a cellulose-containing substrate).

As used herein, the terms "wild-type EG1b polynucleotide," "wild-type EG1b DNA," and "wild-type EG1b nucleic acid" refer to SEQ ID NO: 1. SEQ ID NO:2 is the pre-mature peptide sequence (i.e., containing a signal peptide) of EG1b that is expressed by a naturally occurring *Myceliophthora thermophila* strain.

As used herein, the term "variant" refers to a EG1b polypeptide or polynucleotide encoding a EG1b polypeptide comprising one or more modifications relative to wild-type C1 EG1b or the wild-type polynucleotide encoding C1 EG1b (such as substitutions, insertions, deletions, and/or truncations of one or more amino acid residues or of one or more specific nucleotides or codons in the polypeptide or polynucleotide, respectively), and biologically active fragments thereof. In some embodiments, the variant is a "C1 variant" derived from a C1 EG1b polypeptide and comprising one or more modifications relative to wild-type C1 EG1b or the wild-type polynucleotide encoding wild-type C1 EG1b, or a biologically active fragment thereof.

As used herein, the terms "enzyme variant" and "variant enzyme" are used in reference to enzymes that are similar to a reference enzyme, particularly in their function, but have mutations in their amino acid sequence that make them different in sequence from the wild-type or another reference enzyme. Enzyme variants (e.g., "EG1b variants") can be made by a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific) or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. After the variants are produced, they can be screened for the desired property (e.g., high or increased; or low or reduced activity, increased thermal and/or alkaline stability, etc.).

As used herein, "combinatorial variant" refers to any variant that has a combination of two or more mutations (e.g., substitutions). In some embodiments, the combination of mutations results in changes in enzyme activity (e.g., improved thermostability, improved thermoactivity, improved specific activity, etc.).

The terms "improved" or "improved properties," as used in the context of describing the properties of a EG1b variant, refers to a EG1b variant polypeptide that exhibits an improvement in a property or properties as compared to the wild-type C1 CBH2a or a specified reference polypeptide. Improved properties may include increased protein expression, increased thermoactivity, increased thermostability, increased pH activity, increased stability (e.g., increased pH stability), increased product specificity, increased specific activity, increased substrate specificity, increased resistance to substrate or end-product inhibition, increased chemical stability, reduced inhibition by glucose, increased resistance to inhibitors (e.g., acetic acid, lectins, tannic acids, and phenolic compounds), and altered pH/temperature profile.

As used herein the phrase "improved thermoactivity" or "increased thermoactivity" refers to a variant enzyme displaying an increase, relative to a reference enzyme (e.g., a wild-type EG1b), in the amount of EG1b enzymatic activity (e.g., substrate hydrolysis) in a specified time under specified reaction conditions, for example, elevated temperature. Exemplary methods for measuring EG1b activity are provided in the Examples and include, but are not limited to, measuring cellobiose production from crystalline cellulose as measured by colorimetric assay or HPLC. To compare EG1b activity of two recombinantly expressed proteins, the specific activity (activity per mole enzyme or activity per gram enzyme) can be compared. Alternatively, cells expressing and secreting the recombinant proteins can be cultured under the same conditions and the EG1b activity per volume culture medium can be compared.

As used herein, the term "improved thermostability" or "increased thermostability" refers to a variant enzyme displaying an increase in "residual activity" relative to a reference enzyme (e.g., a wild-type EG1b or a second variant enzyme). Residual activity is determined by (1) exposing the variant enzyme or reference enzyme to stress conditions of elevated temperature, optionally at lowered pH, for a period of time and then determining EG1b activity; (2) exposing the variant enzyme or reference enzyme to unstressed conditions for the same period of time and then determining EG1b activity; and (3) calculating residual activity as the ratio of activity obtained under stress conditions (1) over the activity obtained under unstressed conditions (2). For example, the EG1b activity of the enzyme exposed to stress conditions ("a") is compared to that of a control in which the enzyme is not exposed to the stress conditions ("b"), and residual activity is equal to the ratio a/b. A variant with increased thermostability will have greater residual activity than the wild-type enzyme. In one embodiment the enzymes are exposed to stress conditions of 55° C. at pH 5.0 for 1 hr, but other cultivation conditions, such as conditions described herein, can be used. Exemplary methods for measuring residual EG1b activity are provided in the Examples and include, but are not limited to, measuring cellobiose production from crystalline cellulose as measured by colorimetric assay or HPLC.

As used herein, the term "EG2" refers to a carbohydrate active enzyme expressed from a nucleic acid sequence coding for a glycohydrolase (GH) Family 5 catalytic domain classified under EC 3.2.1.4 or any protein, polypeptide or catalytically active fragment thereof. In some embodiments, the EG2 is functionally linked to a carbohydrate binding module (CBM), such as a Family 1 cellulose binding domain.

As used herein, the term "EG3" refers to a carbohydrate active enzyme expressed from a nucleic acid sequence coding for a glycohydrolase (GH) Family 12 catalytic domain classified under EC 3.2.1.4 or any protein, polypeptide or catalytically active fragment thereof. In some embodiments, the EG3 is functionally linked to a carbohydrate binding module (CBM), such as a Family 1 cellulose binding domain.

As used herein, the term "EG4" refers to a carbohydrate active enzyme expressed from a nucleic acid sequence coding for a glycohydrolase (GH) Family 61 catalytic domain classified under EC 3.2.1.4 or any protein, polypeptide or fragment thereof. In some embodiments, the EG4 is functionally linked to a carbohydrate binding module (CBM), such as a Family 1 cellulose binding domain.

As used herein, the term "EG5" refers to a carbohydrate active enzyme expressed from a nucleic acid sequence coding for a glycohydrolase (GH) Family 45 catalytic domain classified under EC 3.2.1.4 or any protein, polypeptide or fragment thereof. In some embodiments, the EG5 is functionally linked to a carbohydrate binding module (CBM), such as a Family 1 cellulose binding domain.

As used herein, the term "EG6" refers to a carbohydrate active enzyme expressed from a nucleic acid sequence coding for a glycohydrolase (GH) Family 6 catalytic domain classified under EC 3.2.1.4 or any protein, polypeptide or fragment thereof. In some embodiments, the EG6 is functionally linked to a carbohydrate binding module (CBM), such as a Family 1 cellulose binding domain.

As used herein, the terms "cellobiohydrolase" and "CBH" refer to a category of cellulases (EC 3.2.1.91) that hydrolyze glycosidic bonds in cellulose.

As used herein, the terms "CBH1" and "type 1 cellobiohydrolase" refer to a carbohydrate active enzyme expressed from a nucleic acid sequence coding for a glycohydrolase (GH) Family 7 catalytic domain classified under EC 3.2.1.91 or any protein, polypeptide or catalytically active fragment thereof. In some embodiments, the CBH1 is functionally linked to a carbohydrate binding module (CBM), such as a Family 1 cellulose binding domain.

As used herein, the terms "CBH2" and "type 2 cellobiohydrolase" refer to a carbohydrate active enzyme expressed from a nucleic sequence coding for a glycohydrolase (GH) Family 6 catalytic domain classified under EC 3.2.1.91 or any protein, polypeptide or catalytically active fragment thereof. Type 2 cellobiohydrolases are also commonly referred to as "the Cel6 family." The CBH2 may be functionally linked to a carbohydrate binding module (CBM), such as a Family 1 cellulose binding domain.

As used herein, the terms "β-glucosidase," "cellobiase," and "BGL" refers to a category of cellulases (EC 3.2.1.21) that catalyze the hydrolysis of cellobiose to glucose.

As used herein, the term "glycoside hydrolase 61" and "GH61" refers to a category of cellulases that enhance cellulose hydrolysis when used in conjunction with one or more additional cellulases. The GH61 family of cellulases is described, for example, in the Carbohydrate Active Enzymes (CAZY) database (See e.g., Harris et al., Biochem., 49(15): 3305-16 [2010]).

A "hemicellulase" as used herein, refers to a polypeptide that can catalyze hydrolysis of hemicellulose into small polysaccharides such as oligosaccharides, or monomeric saccharides. Hemicelluloses include xylan, glucuronoxylan, arabinoxylan, glucomannan and xyloglucan. Hemicellulases include, for example, the following: endoxylanases, b-xylosidases, a-L-arabinofuranosidases, a-D-glucuronidases, feruloyl esterases, coumaroyl esterases, a-galactosidases, b-galactosidases, b-mannanases, and b-mannosidases. In some embodiments, the present invention provides enzyme mixtures that comprise EG1 b and one or more hemicellulases.

As used herein, "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the present invention. Some specific types of proteases include but are not limited to, cysteine proteases including pepsin, papain and serine proteases including chymotrypsins, carboxypeptidases and metalloendopeptidases.

As used herein, "lipase" includes enzymes that hydrolyze lipids, fatty acids, and acylglycerides, including phosphoglycerides, lipoproteins, diacyiglycerols, and the like. In plants, lipids are used as structural components to limit water loss and pathogen infection. These lipids include waxes derived from fatty acids, as well as cutin and suberin.

As used herein, the terms "isolated" and "purified" are used to refer to a molecule (e.g., an isolated nucleic acid, polypeptide, etc.) or other component that is removed from at least one other component with which it is naturally associated.

As used herein, "polynucleotide" refers to a polymer of deoxyribonucleotides or ribonucleotides in either single- or double-stranded form, and complements thereof.

The terms "protein" and "polypeptide" are used interchangeably herein to refer to a polymer of amino acid residues.

The term "EG1b polynucleotide" refers to a polynucleotide that encodes an endoglucanase 1b polypeptide.

In addition, the terms "amino acid" "polypeptide," and "peptide" encompass naturally-occurring and synthetic amino acids, as well as amino acid analogs. Naturally occurring amino acids are those encoded by the genetic code, as well as those amino acids that are later modified (e.g., hydroxyproline, γ-carboxyglutarmate, and O-phosphoserine). As used herein, the term "amino acid analogs" refers to compounds that have the same basic chemical structure as a naturally occurring amino acid (i.e., an α-carbon that is bound to a hydrogen, a carboxyl group, an amino group, and an R group, including but not limited to homoserine, norleucine, methionine sulfoxide, and methionine methyl sulfonium). In some embodiments, these analogs have modified R groups (e.g., norleucine) and/or modified peptide backbones, but retain the same basic chemical structure as a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, the amino acid residue number in a test sequence determined by simply counting from the N-terminus will not necessarily be the same as the number of its corresponding position in the reference sequence. For example, in a case where a test sequence has a deletion relative to an aligned reference sequence, there will be no amino acid in the variant that corresponds to a position in the reference sequence at the site of deletion. Where there is an insertion in an aligned test sequence, that insertion will not correspond to a numbered amino acid position in the reference sequence. In the case of truncations or fusions there can be stretches of amino acids in either the reference or aligned sequence that do not correspond to any amino acid in the corresponding sequence.

As used herein, the terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. The following nomenclature may be used to describe substitutions in a test sequence relative to a reference sequence polypeptide or nucleic acid sequence: "R-#-V," where # refers to the position in the reference sequence, R refers to the amino acid (or base) at that position in the reference sequence, and V refers to the amino acid (or base) at that position in the test sequence. In some embodiments, an amino acid (or base) may be called "X," by which is meant any amino acid (or base). As a non-limiting example, for a variant polypeptide described with reference to a wild-type EG1b polypeptide (e.g., SEQ ID NO:2), "T43C" indicates that in the polypeptide being compared, the T at position 43 of the reference sequence is replaced by C, with amino acid position being determined by optimal alignment of the variant sequence with SEQ ID NO:2.

As used herein, the term "reference enzyme" refers to an enzyme to which another enzyme of the present invention (e.g., a "test" enzyme, such as an EG1b variant) is compared in order to determine the presence of an improved property in the other enzyme being evaluated. In some embodiments, a reference enzyme is a wild-type enzyme (e.g., wild-type EG1b). In some embodiments, the reference enzyme is an enzyme to which a test enzyme of the present invention is compared in order to determine the presence of an improved property in the test enzyme being evaluated, including but not limited to improved thermoactivity, improved thermostability, and/or improved stability. In some embodiments, a reference enzyme is a wild-type enzyme (e.g., wild-type EG1b).

As used herein, the term "biologically active fragment," refers to a polypeptide that has an amino-terminal and/or carboxy-terminal deletion(s) and/or internal deletion(s), but where the remaining amino acid sequence is identical to the corresponding positions in the sequence to which it is being compared (e.g., a full-length EG1b of the present invention) and that retains substantially all of the activity of the full-length polypeptide. In some embodiments, the biologically active fragment is a biologically active EG1b fragment. A biologically active fragment can comprise about 60%, about 65%, about 70%, about 75%, about 80%, about 85%, at about 90%, about 91%, about 92%, about 93%, about 94%, about 95%, about 96%, about 97%, about 98%, or about 99% of a full-length EG1b polypeptide.

As used herein, the term "overexpress" is intended to encompass increasing the expression of a protein to a level greater than the cell normally produces. It is intended that the term encompass overexpression of endogenous, as well as heterologous proteins.

As used herein, the term "recombinant" refers to a polynucleotide or polypeptide that does not naturally occur in a host cell. In some embodiments, recombinant molecules contain two or more naturally-occurring sequences that are linked together in a way that does not occur naturally. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. Recombinant cells contain at least one recombinant polynucleotide or polypeptide. A nucleic acid construct, nucleic acid (e.g., a polynucleotide), polypeptide, or host cell is referred to herein as "recombinant" when it is non-naturally occurring, artificial or engineered. "Recombination," "recombining" and generating a "recombined" nucleic acid generally encompass the assembly of at least two nucleic acid fragments.

The present invention also provides a recombinant nucleic acid construct comprising an EG1b polynucleotide sequence that hybridizes under stringent hybridization conditions to the complement of a polynucleotide which encodes a polypeptide comprising the amino acid sequence of SEQ ID NO:2.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS 50° C. (low stringency), at 55° C. (medium stringency), at 60° C. (medium-high stringency), at 65° C. (high stringency), or at 70° C. (very high stringency).

As used herein, "identity" or "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

In some embodiments, the terms "percent identity," "% identity", "percent identical," and "% identical," are used interchangeably herein to refer to the percent amino acid or polynucleotide sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following ClustalW parameters to achieve slow/more accurate pairwise optimal alignments- DNA/Protein Gap Open Penalty: 15/10; DNA/Protein Gap Extension Penalty:6.66/0.1; Protein weight matrix: Gonnet series; DNA weight matrix: Identity.

As used herein the term "comparison window." includes reference to a segment of any one of a number of contiguous positions from about 20 to about 464 (e.g., about 50 to about 300 contiguous positions, about 50 to 250 contiguous positions, or also about 100 to about 200 contiguous positions), in which a sequence may be compared to a reference sequence of the same number of contiguous positions after the two sequences are optimally aligned. As noted, in some embodiments the comparison is between the entire lengths of the two sequences, or, if one sequence is a fragment of the other, the entire length of the shorter of the two sequences. Optimal alignment of sequences for comparison and determination of sequence identity can be determined by a sequence comparison algorithm or by visual inspection, as well-known in the art. When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities fir the test sequences relative to the reference sequence, based on the program parameters.

Two sequences are "aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well known in the art (See, e.g., Dayhoff et al., in Dayhoff [ed.], *Atlas of Protein Sequence and Structure.*" Vol. 5, Suppl. 3, Natl. Biomed. Res. Round., Washington D.C. [1978]; pp. 345-352; and Henikoff et al., Proc. Natl. Acad. Sci. USA, 89:10915-10919 [1992], both of which are incorporated herein by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 [1997], which is incorporated herein by reference), and made available to the public at the National Center for Biotechnology Information Website). Optimal alignments, including multiple alignments can be prepared using readily available programs such as PSI-BLAST (See e.g., Altschul et al., supra).

The present invention also provides a recombinant nucleic acid construct comprising an EG1b polynucleotide sequence that hybridizes under stringent hybridization conditions to the complement of a polynucleotide which encodes a polypeptide comprising the amino acid sequence of SEQ ID NO:2, wherein the polypeptide is capable of catalyzing the degradation of cellulose. Two nucleic acid or polypeptide sequences that have 100% sequence identity are said to be "identical." A nucleic acid or polypeptide sequence are said to have "substantial sequence identity" to a reference sequence when the sequences have at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%, or greater sequence identity as determined using the methods described herein, such as BLAST using standard parameters.

As used herein, the term "pre-protein" refers to a protein including an amino-terminal signal peptide (or leader sequence) region attached. The signal peptide is cleaved from the pre-protein by a signal peptidase prior to secretion to result in the "mature" or "secreted" protein.

As used herein, the terms "signal sequence," signal peptide," "leader sequence" and "leader peptide" refer to a sequence of amino acid residues bound at the amino terminus of a nascent protein during protein translation, which when recognized by the signal recognition particle, or analog thereof, results in the transport of the nascent protein either directly to the cell membrane, or to the periplasmic space, or to the outside of the cell, or to the organelle of destination to be subsequently secreted outside of the cell. The nucleotides responsible for the encoding of the signal peptide can also be referred to as a "signal sequence."

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. An "expression vector" has a promoter sequence operably linked to the DNA sequence (e.g., transgene) to drive expression in a host cell, and in some embodiments a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, the term "operably linked" refers to a configuration in which a control sequence is appropriately placed at a position relative to the coding sequence of the DNA sequence such that the control sequence influences the expression of a polypeptide.

As used herein, the term "promoter" refers to a polynucleotide sequence, particularly a DNA sequence, that initiates and facilitates the transcription of a target gene sequence in the presence of RNA polymerase and transcription regulators. In some embodiments, promoters include DNA sequence elements that ensure proper binding and activation of RNA polymerase, influence where transcription will start, affect the level of transcription and, in the case of inducible promoters, regulate transcription in response to environmental conditions. Promoters are located 5' to the transcribed gene and, as used herein, include the sequence 5' from the translation start codon (i.e., in some embodiments, including the 5' untranslated region of the mRNA, typically comprising 100-200bp). Most often, the core promoter sequences lie within 1-2 kb of the translation start site, more often within 1 kbp and often within 750 bp, 500 bp or 200 bp of the translation start site. By convention, the promoter sequence is usually provided as the sequence on the coding strand of the gene it controls.

As used herein, the term "inducible promoter" refers to a promoter that initiates transcription only when the host cell comprising the inducible promoter is exposed to particular environmental factors (e.g., temperature or light responsive promoters), chemical factors (e.g., promoters induced by small molecules, such as IPTG or tetracycline), metabolic factors (e.g., promoters induced or repressed by glucose or metabolites, promoters active during exponential growth phase), physical factors and the like.

As used herein, the term "constitutive promoter" refers to a promoter that drives transcription at about the same level under a variety of environmental or growth conditions. In some embodiments, the term "constitutive promoter" refers to a promoter that is glucose-independent (i.e., is not induced by or repressed by glucose levels). Glucose independent regulation can be determined as described in the Examples below. In additional embodiments, the term "constitutive promoter" refers to a promoter that is not growth dependent (i.e., drives transcription during both exponential and non-exponential growth phases).

As used herein, the term "promoter activity" refers to the level of expression or activity of the gene and/or polypeptide operably linked to the promoter of interest. Any suitable method for determining/measuring promoter activity finds use in the present invention. For example, promoter activity can be measured by estimating the levels of expression of transcript, production of protein, or protein activity by one of ordinary skill in the art by well known methods, including but not limited to quantitative real-time PCR (qRT-PCR), Northern blot hybridization, SDS-PAGE analysis, and/or enzyme activity assays.

As used herein, the term "terminator" refers to a polynucleotide sequence that signals RNA polymerase to terminate transcription.

As used herein, the term "heterologous" refers to a nucleic acid or polypeptide that is cloned and or expressed in a context different from how it is present in nature. The term "heterologous," when used to describe a promoter and an operably linked coding sequence, means that the promoter and the coding sequence are not associated with each other in nature. In some embodiments, a promoter and a heterologous coding sequence are from two different organisms. In some alternative embodiments, a promoter and a heterologous coding sequence are from the same organism, provided the particular promoter does not direct the transcription of the coding sequence in the wild-type organism. Thus, as used herein, an amino acid or nucleotide sequence (e.g., a promoter sequence, signal peptide, terminator sequence, etc.) is "heterologous" to another sequence with which it is operably linked if the two sequences are not associated in nature.

As used herein, the terms "host cell" and "host strain" refer to suitable hosts for expression vectors comprising DNA provided herein. In some embodiments, the host cells are prokaryotic or eukaryotic cells that have been transformed or transfected with vectors constructed using recombinant DNA techniques as known in the art. Transformed hosts are capable of either replicating vectors encoding at least one protein of interest and/or expressing the desired protein of interest. In addition, reference to a cell of a particular strain refers to a parental cell of the strain as well as progeny and genetically modified derivatives. Genetically modified derivatives of a parental cell include progeny cells that contain a modified genome or episomal plasmids that confer for example, antibiotic resistance, improved fermentation, etc. In some embodiments, host cells are genetically modified to have characteristics that improve protein secretion, protein stability or other properties desirable for expression and/or secretion of a protein. For example, knockout of Alp 1function results in a cell that is protease deficient. Knockout of pyr5 function results in a cell with a pyrimidine deficient phenotype. In some embodiments, host cells are modified to delete endogenous cellulase protein-encoding sequences or otherwise eliminate expression of one or more endogenous cellulases. In some embodiments, expression of one or more endogenous cellulases is inhibited to increase production of cellulases of interest. Genetic modification can be achieved by any suitable genetic engineering techniques and/or classical microbiological techniques (e.g., chemical or UV mutagenesis and subsequent selection). Using recombinant technology, nucleic acid molecules can be introduced, deleted, inhibited or modified, in a manner that results in increased yields of EG1b within the organism or in the culture. For example, knockout of Alp1 function results in a cell that is protease deficient. Knockout of pyr5 function results in a cell with a pyrimidine deficient phenotype. In some genetic engineering approaches, homologous recombination is used to induce targeted gene modifications by specifically targeting a gene in vivo to suppress expression of the encoded protein. In an alternative approach, siRNA, antisense, and/or ribozyme technology finds use in inhibiting gene expression.

As used herein, the term "introduced" used in the context of inserting a nucleic acid sequence into a cell, means transformation, transduction, conjugation, transfection, and/or any other suitable method(s) known in the art for inserting nucleic acid sequences into host cells. Any suitable means for the introduction of nucleic acid into host cells find use in the present invention.

As used herein, the terms "transformed" and "transformation" used in reference to a cell refer to a cell that has a non-native nucleic acid sequence integrated into its genome or has an episomal plasmid that is maintained through multiple generations.

As used herein, the term "C1" refers to *Myceliophthora thermophila*, including the fungal strain described by Garg (See, Garg, Mycopathol., 30: 3-4 [1966]). As used herein, "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, all of which are incorporated herein by reference, and include, without limitation. *Chrysosporium lucknowense* Garg 27K, VKM-F 3500 D (Accession No. VKM F-3500-D). C1 strain UV13-6 (Accession No. VKM F-3632 D), C1 strain NG7C-19 (Accession No. VKM F-3633 D), and C1 strain UV 18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006, CBS (Centraalbureau voor Schimmelcultures) 122188, CBS 251.72, CBS 143.77, CBS 272.77, CBS122190, CBS122189, and VKM F-3500D. Exemplary C1 derivatives include modified organisms in which one or more endogenous genes or sequences have been deleted or modified and/or one or more heterologous genes or sequences have been introduced. Derivatives include, but are not limited to UV 18#100fΔalp1, UV 18#100fΔpyr5Δalp1, UV18#100.fΔalp1Δpep4Δalp2, UV18#100.fΔpyr5Δalp1Δpep4Δalp2 and UV18#100.fΔpyr4Δpyr5Δalp1Δpep4Δalp2, as described in WO2008073914 and WO2010107303, each of which is incorporated herein by reference.

As used herein, the terms "improved thermoactivity" and "increased thermoactivity" refer to an enzyme (e.g., a "test" enzyme of interest) displaying an increase, relative to a reference enzyme, in the amount of enzymatic activity (e.g., substrate hydrolysis) in a specified time under specified reaction conditions, for example, elevated temperature.

As used herein, the terms "improved thermostability" and "increased thermostability" refer to an enzyme (e.g., a "test" enzyme of interest) displaying an increase in "residual activity" relative to a reference enzyme. Residual activity is determined by (1) exposing the test enzyme or reference enzyme to stress conditions of elevated temperature, optionally at lowered pH, for a period of time and then determining EG1b activity; (2) exposing the test enzyme or reference enzyme to unstressed conditions for the same period of time and then determining EG1 b activity; and (3) calculating residual activity as the ratio of activity obtained under stress conditions (1) over the activity obtained under unstressed conditions (2). For example, the EG1b activity of the enzyme exposed to stress conditions ("a") is compared to that of a control in which the enzyme is not exposed to the stress conditions ("b"), and residual activity is equal to the ratio a/b. A test enzyme with increased thermostability will have greater residual activity than the reference enzyme. In some embodiments, the enzymes are exposed to stress conditions of 55° C. at pH 5.0 for 1 hr. but other cultivation conditions can be used.

As used herein, the term "culturing" refers to growing a population of microbial cells under suitable conditions in a liquid or solid medium.

As used herein, the term "saccharification" refers to the process in which substrates (e.g., cellulosic biomass) are broken down via the action of cellulases to produce fermentable sugars (e.g. monosaccharides such as but not limited to glucose).

As used herein, the term "fermentable sugars" refers to simple sugars (e.g., monosaccharides, disaccharides and short oligosaccharides), including but not limited to glucose, xylose, galactose, arabinose, mannose and sucrose. Indeed, a fermentable sugar is any sugar that a microorganism can utilize or ferment.

As used herein the term "soluble sugars" refers to water-soluble hexose and pentose monomers and oligomers of up to about seven monomer units.

As used herein, the term "fermentation" is used broadly to refer to the cultivation of a microorganism or a culture of microorganisms that use simple sugars, such as fermentable sugars, as an energy source to obtain a desired product.

As used herein, the term "feedstock" refers to any material that is suitable for use in production of an end product. It is intended that the term encompass any material suitable for use in saccharification reactions. In some embodiments, the term encompasses material obtained from nature that is in an unprocessed or minimally processed state, although it is not intended that the term be limited to these embodiments. In some embodiments, the term encompasses biomass and biomass substrates comprising any suitable compositions for use in production of fermentable sugars. In some embodiments, the feedstock is "pre-treated" before and/or while it is being used as a substrate in a saccharification reaction.

The terms "biomass," and "biomass substrate," encompass any suitable materials for use in saccharification reactions. The terms encompass, but are not limited to materials that comprise cellulose (i.e., "cellulosic biomass," "cellulosic feedstock," and "cellulosic substrate"). Biomass can be derived from plants, animals, or microorganisms, and may include, but is not limited to agricultural, industrial, and forestry residues, industrial and municipal wastes, and terrestrial and aquatic crops grown for energy purposes. Examples of biomass substrates include, but are not limited to, wood, wood pulp, paper pulp, corn fiber, corn grain, corn cobs, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, switchgrass, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to cultivated crops (e.g., grasses, including C4 grasses, such as switch grass, cord grass, rye grass, miscanthus, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in some alternative embodiments, the biomass comprises a mixture of fibers that originate from different biomasses. In some embodiments, the biomass may also comprise transgenic plants that express ligninase and/or cellulase enzymes (See e.g., US 2008/0104724 A1). Thus, the term "biomass" encompasses any living or dead biological material that contains a polysaccharide substrate, including but not limited to cellulose, starch, other forms of long-chain carbohydrate polymers, and mixtures of such sources. It may or may not be assembled entirely or primarily from glucose or xylose, and may optionally also contain various other pentose or hexose monomers. Xylose is an aldopentose containing five carbon atoms and an aldehyde group. It is the precursor to hemicellulose, and is often a main constituent of biomass.

A biomass substrate is said to be "pretreated" when it has been processed by some physical and/or chemical means to facilitate saccharification. A pretreated lignocellulosic feedstock, or pretreated lignocellulose, is a lignocellulosic feedstock that has been subjected to physical and/or chemical processes to make the fiber more accessible and/or receptive to the actions of cellulolytic enzymes. As described further herein, in some embodiments, the biomass substrate is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion, irradiation, or exposure to hot water, etc.), mechanical pretreatment (e.g., grinding or milling) and biological pretreatment (e.g., application of lignin-solubilizing microorganisms and/or enzymes, including but not limited to peroxidases) and combinations thereof, to increase the susceptibility of cellulose to hydrolysis. In some embodiments, the substrate is slurried prior to pretreatment. In some embodiments, the consistency of the slurry is between about 2% and about 30% and more typically between about 4% and about 15%. In some embodiments, the slurry is subjected to a water and/or acid soaking operation prior to pretreatment. In some embodiments, the slurry is dewatered using any suitable method to reduce steam and chemical usage prior to pretreatment. Examples of dewatering devices include, but are not limited to pressurized screw presses (See e.g., WO 2010/022511, incorporated herein by reference) pressurized filters and extruders.

In some embodiments, the pretreatment is carried out to hydrolyze hemicellulose, and/or a portion thereof present in the cellulosic substrate to monomeric pentose and hexose sugars (e.g., xylose, arabinose, mannose, galactose, and/or any combination thereof). In some embodiments, the pretreatment is carried out so that nearly complete hydrolysis of the hemicellulose and a small amount of conversion of cellulose to glucose occurs. In some embodiments, an acid concentration in the aqueous slurry from about 0.02% (w/w) to about 2% (w/w), or any amount therebetween, is typically used for the treatment of the cellulosic substrate. Any suitable acid finds use in these methods, including but not limited to, hydrochloric acid, nitric acid, and/or sulfuric acid. In some embodiments, the acid used during pretreatment is sulfuric acid. Steam explosion is one method of performing acid pretreatment of biomass substrates (See e.g., U.S. Pat. No. 4,461,648). Another method of pretreating the slurry involves continuous pretreatment (i.e., the cellulosic biomass is pumped though a reactor continuously). This methods are well-known to those skilled in the art (See e.g., U.S. Pat. No. 7,754,457).

In some embodiments, alkali is used in the pretreatment. In contrast to acid pretreatment, pretreatment with alkali may not hydrolyze the hemicellulose component of the biomass. Rather, the alkali reacts with acidic groups present on the hemicellulose to open up the surface of the substrate.

In some embodiments, the addition of alkali alters the crystal structure of the cellulose so that it is more amenable to hydrolysis. Examples of alkali that find use in the pretreatment include, but are not limited to ammonia, ammonium hydroxide, potassium hydroxide, and sodium hydroxide. One method of alkali pretreatment is Ammonia Freeze Explosion, Ammonia Fiber Explosion or Ammonia Fiber Expansion ("AFEX" process; See e.g., U.S. Pat. Nos. 5,171,592; 5,037,663; 4,600,590; 6,106,888; 4,356,196; 5,939,544; 6,176,176; 5,037,663 and 5,171,592). During this process, the cellulosic substrate is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. In some embodiments, the flashed ammonia is then recovered using methods known in the art. In some alternative methods, dilute ammonia pretreatment is utilized. The dilute ammonia pretreatment method utilizes more dilute solutions of ammonia or ammonium hydroxide than AFEX (See e.g., WO2009/045651 and US 2007/0031953). This pretreatment process may or may not produce any monosaccharides.

An additional pretreatment process for use in the present invention includes chemical treatment of the cellulosic substrate with organic solvents, in methods such as those utilizing organic liquids in pretreatment systems (See e.g., U.S. Pat. No. 4,556,430; incorporated herein by reference). These methods have the advantage that the low boiling point liquids easily can be recovered and reused. Other pretreatments, such as the Organosolv™ process, also use organic liquids (See e.g., U.S. Pat. No. 7,465,791, which is also incorporated herein by reference). Subjecting the substrate to pressurized water may also be a suitable pretreatment method (See e.g., Weil et al. (1997) Appl. Biochem. Biotechnol., 68(1-2): 21-40 [1997], which is incorporated herein by reference). In some embodiments, the pretreated cellulosic biomass is processed after pretreatment by any of several steps, such as dilution with water, washing with water, buffering, filtration, or centrifugation, or any combination of these processes, prior to enzymatic hydrolysis, as is familiar to those skilled in the art. The pretreatment produces a pretreated feedstock composition (e.g., a "pretreated feedstock slurry") that contains a soluble component including the sugars resulting from hydrolysis of the hemicellulose, optionally acetic acid and other inhibitors, and solids including unhydrolyzed feedstock and lignin. In some embodiments, the soluble components of the pretreated feedstock composition are separated from the solids to produce a soluble fraction. In some embodiments, the soluble fraction, including the sugars released during pretreatment and other soluble components (e.g., inhibitors), is then sent to fermentation. However, in some embodiments in which the hemicellulose is not effectively hydrolyzed during the pretreatment one or more additional steps are included (e.g., a further hydrolysis step(s) and/or enzymatic treatment step(s) and/or further alkali and/or acid treatment) to produce fermentable sugars. In some embodiments, the separation is carried out by washing the pretreated feedstock composition with an aqueous solution to produce a wash stream and a solids stream comprising the unhydrolyzed, pretreated feedstock. Alternatively, the soluble component is separated from the solids by subjecting the pretreated feedstock composition to a solids-liquid separation, using any suitable method (e.g., centrifugation, microfiltration, plate and frame filtration, cross-flow filtration, pressure filtration, vacuum filtration, etc.). Optionally, in some embodiments, a washing step is incorporated into the solids-liquids separation. In some embodiments, the separated solids containing cellulose, then undergo enzymatic hydrolysis with cellulase enzymes in order to convert the cellulose to glucose. In some embodiments, the pretreated feedstock composition is fed into the fermentation process without separation of the solids contained therein. In some embodiments, the unhydrolyzed solids are subjected to enzymatic hydrolysis with cellulase enzymes to convert the cellulose to glucose after the fermentation process. In some embodiments, the pretreated cellulosic feedstock is subjected to enzymatic hydrolysis with cellulase enzymes.

As used herein, the term "lignocellulosic biomass" refers to any plant biomass comprising cellulose and hemicellulose, bound to lignin. In some embodiments, the biomass may optionally be pretreated to increase the susceptibility of cellulose to hydrolysis by chemical, physical and biological pretreatments (such as steam explosion, pulping, grinding, acid hydrolysis, solvent exposure, and the like, as well as combinations thereof). Various lignocellulosic feedstocks find use, including those that comprise fresh lignocellulosic feedstock, partially dried lignocellulosic feedstock, fully dried lignocellulosic feedstock, and/or any combination thereof. In some embodiments, lignocellulosic feedstocks comprise cellulose in an amount greater than about 20%, more preferably greater than about 30%, more preferably greater than about 40% (w/w). For example, in some embodiments, the lignocellulosic material comprises from about 20% to about 90% (w/w) cellulose, or any amount therebetween, although in some embodiments, the lignocellulosic material comprises less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5% cellulose (w/w). Furthermore, in some embodiments, the lignocellulosic feedstock comprises lignin in an amount greater than about 10%, more typically in an amount greater than about 15% (w/w). In some embodiments, the lignocellulosic feedstock comprises small amounts of sucrose, fructose and/or starch. The lignocellulosic feedstock is generally first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In some embodiments, at least 90% by weight of the particles produced from the size reduction have lengths less than between about $\frac{1}{16}$ and about 4 in (the measurement may be a volume or a weight average length). In some embodiments, the equipment used to reduce the particle size reduction is a hammer mill or shredder. Subsequent to size reduction, the feedstock is typically slurried in water, as this facilitates pumping of the feedstock. In some embodiments, lignocellulosic feedstocks of particle size less than about 6 inches do not require size reduction.

As used herein, the term "lignocellulosic feedstock" refers to any type of lignocellulosic biomass that is suitable for use as feedstock in saccharification reactions.

As used herein, the term "pretreated lignocellulosic feedstock," refers to lignocellulosic feedstocks that have been subjected to physical and/or chemical processes to make the fiber more accessible and/or receptive to the actions of cellulolytic enzymes, as described above.

As used herein, the term "recovered" refers to the harvesting, isolating, collecting, or recovering of protein from a cell and/or culture medium. In the context of saccharification, it is used in reference to the harvesting of fermentable sugars produced during the saccharification reaction from the culture medium and/or cells. In the context of fermentation, it is used in reference to harvesting the fermentation product from the culture medium and/or cells. Thus, a process can be said to comprise "recovering" a product of a reaction (such as a soluble sugar recovered from saccharitication) if the process includes separating the product from other components of a reaction mixture subsequent to at least some of the product being generated in the reaction.

As used herein, the term "slurry" refers to an aqueous solution in which are dispersed one or more solid components, such as a cellulosic substrate.

As used herein, "increasing" the yield of a product (such as a fermentable sugar) from a reaction occurs when a particular component of interest is present during the reaction (e.g., EG 1 b) causes more product to be produced, compared with a reaction conducted under the same conditions with the same substrate and other substituents, but in the absence of the component of interest (e.g., without EG1b).

As used herein, a reaction is said to be "substantially free" of a particular enzyme if the amount of that enzyme compared with other enzymes that participate in catalyzing the reaction is less than about 2%, about 1%, or about 0.1% (wt/wt).

As used herein, "fractionating" a liquid (e.g., a culture broth) means applying a separation process (e.g., salt precipitation, column chromatography, size exclusion, and filtration) or a combination of such processes to provide a solution in which a desired protein (such as an EG1b protein, a cellulase enzyme, and/or a combination thereof) comprises a greater percentage of total protein in the solution than in the initial liquid product.

As used herein, the term "enzymatic hydrolysis", refers to a process comprising at least one cellulases and at least one glycosidase enzyme and/or a mixture glycosidases that act on polysaccharides, (e.g., cellulose), to convert all or a portion thereof to fermentable sugars. "Hydrolyzing" cellulose or other polysaccharide occurs when at least some of the glycosidic bonds between two monosaccharides present in the substrate are hydrolyzed, thereby detaching from each other the two monomers that were previously bonded.

It is intended that the enzymatic hydrolysis be carried out with any suitable type of cellulase enzymes capable of hydrolyzing the cellulose to glucose, regardless of their source, including those obtained from fungi, such as *Trichoderma* spp., *Aspergillus* spp., *Hypocrea* spp., *Humicola* spp., *Neurospora* spp., *Orpinomyces* spp., *Gibberella* spp., *Emericella* spp., *Chaetomium*spp., *Chrysosporium* spp., *Fusarium* spp., *Penicillium* spp., *Magnaporthe* spp., *Phanerochaete* spp., *Trametes* spp., *Lentinula edodes, Gleophyllum trabeiu, Ophiostoma piliferum, Corpinus cinereus, Geomyces pannorum, Cryptococcus laurentii. Aureobasidium pullulans, Amorphotheca resinae, Leucosporidium scotti, Cunninghamella elegans, Thermomyces lanuginosus, Myceliophthora thermophila*, and *Sporotrichum thermophile*, as well as those obtained from bacteria of the genera *Bacillus. Thermomyces, Clostridium, Streptomyces* and *Thermobifida*. Cellulase compositions typically comprise one or more cellobiohydrolase, endoglucanase, and beta-glucosidase enzymes. In some cases, the cellulase compositions additionally contain hemicellulases, esterases, swollenins, cips, etc. Many of these enzymes are readily commercially available.

In some embodiments, the enzymatic hydrolysis is carried out at a pH and temperature that is at or near the optimum for the cellulase enzymes being used. For example, the enzymatic hydrolysis may be carried out at about 30° C. to about 75° C., or any suitable temperature therebetween, for example a temperature of about 30° C., about 35° C., about 40° C., about 45° C., about 50° C., about 55° C., about 60° C., about 65° C., about 70° C., about 75° C., or any temperature therebetween, and a pH of about 3.5 to about 7.5, or any pH therebetween (e.g., about 3.5, about 4.0, about 4.5, about 5.0, about 5.5, about 6.0, about 6.5, about 7.0, about 7.5, or any suitable pH therebetween). In some embodiments, the initial concentration of cellulose, prior to the start of enzymatic hydrolysis, is preferably about 0.1% (w/w) to about 20% (w/w), or any suitable amount therebetween (e.g., about 0.1%, about 0.5%, about 1%, about 2%, about 4%, about 6%, about 8%, about 10%, about 12%, about 14%, about 15%, about 18%, about 20%, or any suitable amount therebetween.) In some embodiments, the combined dosage of all cellulase enzymes is about 0.001 to about 100 mg protein per gram cellulose, or any suitable amount therebetween (e.g., about 0.001, about 0.01, about 0.1, about 1, about 5, about 10, about 15, about 20, about 25, about 30, about 40, about 50, about 60, about 70, about 80, about 90, about 100 mg protein per gram cellulose or any amount therebetween. The enzymatic hydrolysis is carried out for any suitable time period. In some embodiments, the enzymatic hydrolysis is carried out for a time period of about 0.5 hours to about 200 hours, or any time therebetween (e.g., about 2 hours to about 100 hours, or any suitable time therebetween). For example, in some embodiments, it is carried out for about 0.5, about 1, about 2, about 5, about 7, about 10, about 12, about 14, about 15, about 20, about 25, about 30, about 35, about 40, about 45, about 50, about 55, about 60, about 65, about 70, about 75, about 80, about 85, about 90, about 95, about 100, about 120, about 140, about 160, about 180, or about 200 hours, or any suitable time therebetween.)

In some embodiments, the enzymatic hydrolysis is batch hydrolysis, continuous hydrolysis, and/or a combination thereof. In some embodiments, the hydrolysis is agitated, unmixed, or a combination thereof. The enzymatic hydrolysis is typically carried out in a hydrolysis reactor. The cellulase enzyme composition is added to the pretreated lignocellulosic substrate prior to, during, or after the addition of the substrate to the hydrolysis reactor. Indeed it is not intended that reaction conditions be limited to those provided herein, as modifications are well-within the knowledge of those skilled in the art. In some embodiments, following cellulose hydrolysis, any insoluble solids present in the resulting lignocellulosic hydrolysate, including but not limited to lignin, are removed using conventional solid-liquid separation techniques prior to any further processing. In some embodiments, these solids are burned to provide energy for the entire process.

As used herein, the term "by-product" refers to an organic molecule that is an undesired product of a particular process (e.g., saccharification).

DETAILED DESCRIPTION OF THE INVENTION

The present invention provides endoglucanase 1b (EG1b) variants suitable for use in saccharification reactions. The present application further provides genetically modified fungal organisms that produce EG1b variants, as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures.

In some embodiments, the EG1b is obtained from *Myceliophthora thermophila*.

In some embodiments, the present invention provides methods and compositions suitable for use in the degradation of cellulose. In some additional embodiments, the present invention provides EG1b enzymes suitable for use in saccharification reactions to hydrolyze cellulose components in biomass feedstock. In some additional embodiments, the EG1b enzymes are used in combination with additional enzymes, including but not limited to EG1a, EG2, EG3, EG5, EG6, cellobiohydrolase(s), GH61s, etc., in saccharification reactions.

Fungi, bacteria, and other organisms produce a variety of cellulases and other enzymes that act in concert to catalyze decrystallization and hydrolysis of cellulose to yield fermentable sugars. One such fungus is *M. thermophila*, which is described hereinabove. One cellulase of interest is the EG1b enzyme. The EG1b sequences provided herein are particularly useful for the production of fermentable sugars from cellulosic biomass. In one aspect, the present invention provides EG1b variants that have improved properties, relative to wild-type *M. thermophila* EG1b (SEQ ID NO:2), under process conditions used for saccharification of biomass. Improved properties, described hereinabove, include properties such as increased thermostability and/or increased thermoactivity and/or increased pH tolerance. In another aspect, the present invention relates to methods of generating fermentable sugars from cellulosic biomass, by contacting the biomass with a cellulase composition comprising at least one EG1b and/or EG1b variant as described herein under conditions suitable for the production of fermentable sugars. Increased thermostability, especially at extreme pH, can be useful for improving yields in saccharification, improving rates of saccharification. Various aspects of the invention are described in the following sections.

EG1b Variants

The present invention provides EG1b variants, and biologically active fragments thereof, comprising improved properties over a wild-type EG1b. In some embodiments, the EG1b variants exhibit increased thermostability in comparison to a wild-type EG1b (e.g., EG1b comprising the amino acid sequence of SEQ ID NO:2) under conditions relevant to commercial cellulose hydrolysis processes. In some embodiments, the present invention provides a recombinant EG1b variant comprising at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprising an amino acid substitution at one or more positions selected from 5, 6, 7, 8, 9, 10, 11, 12, 13, 14, 15, 16, 17, 18, 19, 20, 21, 22, 34, 38, 39, 43, 49, 63, 66, 75, 85, 126, 137, 143, 201, 218, 228, 241, 269, 274, 282, 328, 342, 342, 350, 397, 398, 399, 400, 401, 403, 404, 405, 407, 408, 409, 411, 412, 413, 414, 415, 417, 418, 419, 420, 425, 428, 433, 434, 435, 438, 439, 440, 443, 444, 446, 457, and 464, wherein the positions are numbered with reference to SEQ ID NO:2, and wherein the variant has increased thermostability and/or activity on cellulose and/or biomass substrate(s), in comparison to wild-type *M. thermophila* EG1b (SEQ ID NO:2). In some embodiments, a EG1b variant has an amino acid sequence that is encoded by a nucleic acid that hybridizes under high stringency conditions to the complement of SEQ ID NO:2 (e.g., over substantially the entire length of a nucleic acid exactly complementary to SEQ ID NO:2) and comprises an amino acid substitution at one or more positions selected from 5, 6, 7, 8, 9, 10, 11, 12, 13, 14, 15, 16, 17, 18, 19, 20, 21, 22, 34, 38, 39, 43, 49, 63, 66, 75, 85, 126, 137, 143, 201, 218, 228, 241, 269, 274, 282, 328, 342, 342, 350, 397, 398, 399, 400, 401, 403, 404, 405, 407, 408, 409, 411, 412, 413, 414, 415, 417, 418, 419, 420, 425, 428, 433, 434, 435, 438, 439, 440, 443, 444, 446, 457, and 464, wherein the positions are numbered with reference to SEQ ID NO:2.

In some embodiments, the EG1b variant comprises at least about 1, at least about 2, at least about 3, at least about 4, at least about 5, at least about 6, at least about 7, at least about 8, at least about 9, or at least about 10 or more amino acid residues which have been substituted (e.g., with substitutions described herein) as compared to the amino acid sequence of the wild-type EG1b protein from which the EG1b variant is derived.

It will be appreciated that in some embodiments, secreted EG1b variants of the present invention encompass additional amino acid substitutions beyond those listed above (such as additional conservative substitutions), as well as variants that are less-than-full length compared to a wild-type secreted EG1b protein, and those that contain additional residues at the amino and/or carboxy termini. Thus, EG1b variants of the present invention may comprise insertions and/or deletions (e.g., truncation at the amino- and/or carboxy-termini) relative to SEQ ID NO: 1. For illustration and not limitation, in some embodiments the variant are longer or shorter by up to about 10%, about 5%, about 4%, about 3%, about 2%, or about 1% of the wild-type length.

Thus, in some embodiments, the present invention provides biologically active fragments of the EG1b variant polypeptides described herein are also contemplated and encompassed herein. In some embodiments the biologically active fragments comprise at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the corresponding full-length EG1b variant. In some embodiments, the biologically active fragments exhibit improved properties, relative to wild-type EG1b, such as increased thermostability and/or increased thermoactivity and/or increased pH tolerance. In some embodiments, regions of one or both termini (e.g., from about 1 to about 10, about 1 to about 15, or about 1 to about 20 residues at one or both termini), are removed without significantly deleteriously affecting the activity of the enzyme.

In some embodiments, the EG1b variant exhibits at least about 10%, at least about 20%, at least about 50%, at least about 60%, at least about 70%, at least about 75%, at least about 80%, at least about 85%, at least about 90%, at least about 95%, at least about 100%, or more than 100% improvement in any desired property as compared to a control (e.g., wild-type EG1b or another reference enzyme). In some embodiments, the desired property is improved thermostability, while in some other embodiments, the desired property is improved activity on cellulosic or other substrates. It is not intended that the present invention be limited to any particular desired properties nor specific levels of improvement, as a range of properties and levels find use in the present invention.

In some embodiments, the present invention contemplates that mutations (i.e., substitutions, insertions and/or deletions) are introduced into EG1b enzymes of fungal species other than *M. thermophila*, at positions corresponding to the amino acid positions of wild-type *M. thermophila* EG1b (SEQ ID NO:2), to produce variants, or biologically active fragments thereof, comprising improved properties, such as improved thermostability, relative to the EG 1 b from which the variant is derived (e.g., wild-type EG1b or an EG1b of a fungal species other than *M. thermophila*).

Those of skill in the art know that it is possible to use sequence alignment or other methods to identify amino acid positions in structurally related proteins (i.e., homologs) that correspond to each other. In some embodiments, corresponding positions in homologs are considered "Performance Sensitive Positions" (PSPs) when a substitution in that position is determined to affect a property in a set of multiple homologs. Substitutions at PSPs in other homologs are expected to also have significant effects on activity.

In some embodiments, the EG1b variant of the present invention is derived from a EG1b polypeptide from a fungal strain. In some embodiments, the EG1b variant comprises at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to a EG1b from *M. thermophila* (SEQ ID NO:2). The following organisms produce EG1b homologues that find use in the present invention: *Thielavia terrestris* NRRL 8126, *Chaetomium globosum* CBS 148.51, *Neosartorya fischeri* NRRL 181. *Aspergillus fumigatus* Af293. *Aspergillus fumigatus* A1163, *Aspergillus terreus* NIH2624, *Trichoderma virens* Gv29-8, *Hypocrea pseudokoningii*, *Trichoderma longibrachiatum*, and *Trichoderma* sp. SSL.

In some embodiments, the EG1b variants of the present invention are subjected to further modification to produce new variants that retain the specific substitutions that characterize the variant and exhibit desirable properties. For example, a polynucleotide encoding an EG1 b with an improved property can be subjected to additional rounds of mutagenesis to generate polypeptides with further improvements in the desired enzyme or enzyme properties. In some embodiments, EG1b variants are generated according to the methods described herein and be screened for the presence of improved properties, such as increased thermostability. In some embodiments, libraries of EG1b variant polypeptides (and/or polynucleotides encoding the variant) are generated from a parental sequence (e.g., wild-type *M. thermophila* EG1b, or a wild-type EG1b from another fungal strain, or one of the EG1b variants exemplified herein), and screened using a high throughput screen to determine improved properties such as increased stability at desired conditions, as described herein. Methods for generating variant libraries of polynucleotides encoding modified polypeptides are well known in the art. For example, mutagenesis and directed evolution methods can be readily applied to polynucleotides encoding the EG1b polypeptides to generate variant libraries that can be expressed, screened, and assayed using the methods described herein. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811,238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229: 1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol, 14:315-319 [1996]; Stemmer, Nature, 370:389-391 [1994]; Stemmer. Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

In some embodiments, EG1b variants comprising the amino acid mutations (e.g., substitutions, insertions and/or deletions) described herein are produced by recombinant expression or by chemical synthesis. In some embodiments, chemically synthesized polypeptides are made using the well-known techniques of solid phase, liquid phase, or peptide condensation techniques, and can include any combination of amino acids as desired to produce the variants described herein. In addition, synthetic amino acids can be obtained from Sigma, Cambridge Research Biochemical, or any other chemical company familiar to those skilled in the art. Indeed, it is contemplated that any suitable methods to produce the variants provided herein will find use in the present invention. It is not intended that the present invention be limited to any particular method of production.

EG1b activity and thermostability can be determined by methods described in the Examples, and/or using other suitable assay methods known in the art. For example, EG1b activity may be determined using an assay that measures the conversion of crystalline cellulose to glucose. For example, EG1b activity can be determined using a cellulose assay, in which the ability of the EG1b to hydrolyze a cellulose substrate to cellobiose (e.g., crystalline cellulose under specific temperature and/or pH conditions is measured, then a β-glucosidase is added to convert the cellobiose to glucose). In some embodiments, conversion of cellulose substrate (e.g., crystalline cellulose) to fermentable sugar oligomers (e.g., glucose) is determined by art-known means, including but not limited to coupled enzymatic assay and colorimetric assay. For example, glucose concentrations can be determined using a coupled enzymatic assay based on glucose oxidase and horseradish peroxidase (e.g., GOPOD assay; See e.g., Trinder, Ann. Clin. Biochem., 6:24-27 [1969], which is incorporated herein by reference in its entirety). GOPOD assay kits are known in the art and are readily commercially available (e.g., from Megazyme). In addition, methods for performing GOPOD assays are well-known in the art (See e.g., McCleary et al., J. AOAC Intl., 85(5):1103-11 [2002], the contents of which are incorporated by reference herein). Additional methods of cellobiose quantification include, but are not limited chromatographic methods (e.g., HPLC; See e.g., U.S. Pat. Nos. 6,090,595 and 7,419,809, both of which are incorporated by reference in their entireties).

In some additional embodiments, EG1b variant thermostability is determined by exposing the EG1b variant(s) and the reference (e.g., wild-type) EG1b to stress conditions of elevated temperature for a desired period of time and then determining residual EG1b activity using an assay that measures the conversion of cellulose to glucose, as described herein.

As provided herein, some EG1b variants of the present invention have improved thermostability and/or activity as compared to a reference sequence (e.g., a wild-type EG1b or another EG1b variant). In some embodiments, a EG1b variant has improved thermostability and/or activity at a pH range of about 3.0 to about 7.5, at a pH range of about 3.5 to about 6.5, at a pH range of about 3.5 to about 6.0, at a pH range of about 3.5 to about 5.5, at a pH range of about 3.5 to about 5.0, at a pH range of about 3.6 to about 7.0, at a pH range of about 3.7 to about 7.1, or at a pH range of about 4.0 to about 5.0. In some embodiments, a EG1b variant has improved thermostability and/or activity at a temperature of about 50° C. to about 80° C., at a temperature of about 60° C. to 80° C., at a temperature of about 65° C. to 70° C., at a temperature of about 65° C. to 80° C., or at a temperature of about 65 to 75° C. In some embodiments, a EG1b variant will have improved thermostability and/or activity at a pH of 3.5 to 5.5 and a temperature of 55-70° C. In some embodiments, the EG1b variants have improved activity over a pH range of about 3.7 to about 7.1 and a temperature range of about 50° C. to about 80° C. In some additional embodiments, the EG1b variants have improved thermostability over a temperature range of 65 to 70° C., at pH 4.5.

In some embodiments, the EG1b variants of the invention exhibit EG1b thermostability that is at least about 10%, at least about 15%, at least about 20%, at least about 30%, at least about 40%, at least about 50%, at least about 60%, at least about 70%, at least about 75%, at least about 80%, at least about 85%, at least about 90%, at least about 95%, at least about 100%, or more than 100% improved, as compared to a reference EG1b (e.g., the wild-type EG1b of SEQ ID NO: 1 or another variant) when tested under the same conditions.

The present invention also provides EG1b variant fusion polypeptides, wherein the fusion polypeptide comprises an amino acid sequence encoding a EG1b variant polypeptide of the present invention or fragment thereof, linked either directly or indirectly through the N- or C-terminus of the EG1b variant polypeptide to an amino acid sequence encoding at least a second (additional) polypeptide. In some embodiments, the EG1b variant fusion polypeptide may further include amino acid sequence encoding a third, fourth, fifth, or additional polypeptides. Typically, each additional polypeptide has a biological activity, or alternatively, is a portion of a polypeptide that has a biological activity, where the portion has the effect of improving expression and/or secretion and/or purification and/or detection of the fusion polypeptide from the desired expression host. These sequences may be fused, either directly or indirectly, to the N- or C-terminus of the EG1b variant polypeptide or fragment thereof, or alternatively, to the N- or C-terminus of the additional polypeptides comprising biological activity.

In some embodiments, the additional polypeptide(s) encode an enzyme or active fragment thereof, and/or a polypeptide that improves expression and/or secretion of the fusion polypeptide from the desired expression host cell. For example, in some embodiments, the additional polypeptide encodes a cellulase (for example, a EG1b comprising a different amino acid sequence from the EG1b variant polypeptide in the fusion polypeptide, or a polypeptide exhibiting endoglucanase activity or β-glucosidase activity) and/or a polypeptide that improves expression and secretion from the desired host cell, such as, for example, a polypeptide that is normally expressed and secreted from the desired expression host, such as a secreted polypeptide normally expressed from filamentous fungi. These include glucoamylase, α-amylase and aspartyl proteases from *Aspergillus niger, Aspergillus niger* var. *awamori*, and *Aspergillus oryzae*, EG1b I, EG1b II, endoglucanase I and endoglucanase III from *Trichoderma* and glucoamylase from *Neurospora* and *Humicola* species (See e.g., WO 98/31821, which is incorporated herein by reference).

The polypeptide components of the fusion polypeptide may be linked to each other indirectly via a linker. Linkers suitable for use in the practice of the present invention, include but are not limited to those described in WO 2007/075899, which is incorporated herein by reference. Exemplary linkers include peptide linkers of from about 1 to about 40 amino acid residues in length, including those from about 1 to about 20 amino acid residues in length, and those from about 1 to about 10 amino acid residues in length. In some embodiments, the linkers comprise a single amino acid residue, such as, for example, a Gly, Ser, Ala, or Thr residue or combinations thereof; particularly Gly and Ser. In some embodiments, the linkers are cleavable. In some embodiments, suitable cleavable linkers contain a cleavage site, such as a protease recognition site. Exemplary protease recognition sites are well known in the art and include, but are not limited to Lys-Arg (the KEX2 protease recognition site, which can be cleaved by a native *Aspergillus* KEX2-like protease), and Lys and Arg (the trypsin protease recognition sites).

In some embodiments, the EG1b variants of the present invention further comprise additional sequences which do not alter the encoded activity of the EG b. For example, the EG1b may be linked to an epitope tag or to another sequence useful in purification.

In some embodiments, the variant EG1bs are fusion proteins comprising a polypeptide comprising at least about 70% amino acid sequence identity to SEQ ID NO:1 and comprising one or more substitutions or substitution sets as described herein and further comprising a cellulose binding domain (CBD). In some embodiments, the CBD is heterologous to the polypeptide comprising at least about 70% amino acid sequence identity to SEQ ID NO:1 and one or more substitutions or substitution sets as described herein. For example, in some embodiments the EG1b variants of the present invention comprise polypeptides comprising at least about 70% amino acid sequence identity to SEQ ID NO:1 and one or more substitutions or substitution sets as described herein and fused to a CBD from a cellobiohydrolase protein (e.g., a CBD from CBH2b). In some embodiments, the CBD is joined to the polypeptide by a linker peptide. In some embodiments, a cellobiohydrolase variant of the present invention has multiple CBDs. The multiple CBDs can be in tandem or in different regions of the polypeptide. In some embodiments, the EG1b variants do not comprise a CBD. In some additional embodiments, the fusion proteins comprise one or more EG1b variant and at least one additional amino acid sequence comprising at least one sequence of interest.

The present invention provides endoglucanase 1b (EG1b) variants suitable for use in saccharitication reactions. In some embodiments, the present invention provides methods and compositions suitable for use in the degradation of cellulose. In some additional embodiments, the present invention provides EG1b variant enzymes suitable for use in saccharification reactions to hydrolyze cellulose components in biomass feedstock. In some additional embodiments, the EG1b variants are used in combination with additional enzymes, including but not limited to at least one EG (e.g., wild-type EG1b, EG1a, EG2, EG3, EG4, EG5, and/or EG6), cellobiohydrolase, GH61, and/or beta-glucosidases, etc., in saccharification reactions.

Fungi, bacteria, and other organisms produce a variety of cellulases and other enzymes that act in concert to catalyze decrystallization and hydrolysis of cellulose to yield fermentable sugars. One such fungus is *M. thermophila*, which is described hereinabove. The EG1b variant sequences provided herein are particularly useful for the production of fermentable sugars from cellulosic biomass and other feedstocks. In some additional embodiments, the present invention provides methods for generating fermentable sugars from biomass, involving contacting the biomass with a cellulase composition comprising at least one EG1b variant as described herein, under conditions suitable for the production of fermentable sugars.

In some embodiments, the EG1b variants of the present invention further comprises additional sequences which do not alter the encoded activity of the enzyme. For example, in some embodiments, the EG1b variants are linked to an epitope tag or to another sequence useful in purification.

In some embodiments, the EG1b variant polypeptides of the present invention are secreted from the host cell in which they are expressed (e.g., a yeast or filamentous fungal host cell) and are expressed as a pre-protein including a signal peptide (i.e., an amino acid sequence linked to the amino terminus of a polypeptide and which directs the encoded polypeptide into the cell secretory pathway). In some embodiments, the signal peptide is an endogenous *M. thermophila* EG1b signal peptide. In some other embodiments, signal peptides from other *M. thermophila* secreted proteins are used. In some embodiments, other signal peptides find use, depending on the host cell and other factors. Effective signal peptide coding regions for filamentous fungal host cells include, but are not limited to, the signal peptide coding regions obtained from *Aspergillus oryzae* TAKA amylase, *Aspergillus niger* neutral amylase, *Aspergillus niger* glucoamylase, *Rhizomucor miehei* asparatic proteinase, *Humicola insolens* cellulase, *Humicola lanuginosa* lipase, and *T. reesei* cellobiohydrolase II. Signal peptide coding regions for bacterial host cells include, but are not limited to the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* β-lactamase. *Bacillus stearothermophilus* neutral proteases (nprT, nprS, nprM), and *Bacillus subtilis*prsA. In some additional embodiments, other signal peptides find use in the present invention (See e.g., Simonen and Palva. Microbiol Rev., 57: 109-137 [1993], incorporated herein by reference). Additional useful signal peptides for yeast host cells include those from the genes for *Saccharomyces cerevisiae* alpha-factor, *Saccharomyces cerevisiae* SUC2 invertase (See e.g., Taussig and Carlson. Nucleic Acids Res., 11:1943-54 [1983]; SwissProt Accession No. P00724; and Romanos et al. Yeast 8:423-488 [1992]). In some embodiments, variants of these signal peptides and other signal peptides find use.

In some embodiments, the present invention provides polynucleotides encoding EG1b variant polypeptides, and/or biologically active fragments thereof, as described herein. In some embodiments, the polynucleotide is operably linked to one or more heterologous regulatory or control sequences that control gene expression to create a recombinant polynucleotide capable of expressing the polypeptide. In some embodiments, expression constructs containing a heterologous polynucleotide encoding EG1b variants are introduced into appropriate host cells to express the EG1b variants.

Those of ordinary skill in the art understand that due to the degeneracy of the genetic code, a multitude of nucleotide sequences encoding EG1b variant polypeptides of the present invention exist. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that "U" in an RNA sequence corresponds to "T" in a DNA sequence. The invention contemplates and provides each and every possible variation of nucleic acid sequence encoding a polypeptide of the invention that could be made by selecting combinations based on possible codon choices.

A DNA sequence may also be designed for high codon usage bias codons (codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. A codon whose frequency increases with the level of gene expression is typically an optimal codon for expression. In particular, a DNA sequence can be optimized for expression in a particular host organism. A variety of methods are well-known in the art for determining the codon frequency (e.g., codon usage, relative synonymous codon usage) and codon preference in specific organisms, including multivariate analysis (e.g., using cluster analysis or correspondence analysis,) and the effective number of codons used in a gene. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTs), or predicted coding regions of genomic sequences, as is well-known in the art. Polynucleotides encoding EG1b variants can be prepared using any suitable methods known in the art. Typically, oligonucleotides are individually synthesized, then joined (e.g., by enzymatic or chemical ligation methods, or polymerase-mediated methods) to form essentially any desired continuous sequence. In some embodiments, polynucleotides of the present invention are prepared by chemical synthesis using, any suitable methods known in the art, including but not limited to automated synthetic methods. For example, in the phosphoramidite method, oligonucleotides are synthesized (e.g., in an automatic DNA synthesizer), purified, annealed, ligated and cloned in appropriate vectors. In some embodiments, double stranded DNA fragments are then obtained either by synthesizing the complementary strand and annealing the strands together under appropriate conditions, or by adding the complementary strand using DNA polymerase with an appropriate primer sequence. There are numerous general and standard texts that provide methods useful in the present invention are well known to those skilled in the art.

The present invention also provides recombinant constructs comprising a sequence encoding at least one EG1b variant, as provided herein. In some embodiments, the present invention provides an expression vector comprising an EG1b variant polynucleotide operably linked to a heterologous promoter. In some embodiments, expression vectors of the present invention are used to transform appropriate host cells to permit the host cells to express the EG1b variant protein. Methods for recombinant expression of proteins in fungi and other organisms are well known in the art, and a number expression vectors are available or can be constructed using routine methods. In some embodiments, nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. In some embodiments, polynucleotides of the present invention are incorporated into any one of a variety of expression vectors suitable for expressing EG1b variant polypeptide(s). Suitable vectors include, but are not limited to chromosomal, nonchromosomal and synthetic DNA sequences (e.g., derivatives of SV40), as well as bacterial plasmids, phage DNA, baculovirus, yeast plasmids, vectors derived from combinations of plasmids and phage DNA, viral DNA such as vaccinia, adenovirus, fowl pox virus, pseudorabies, adenovirus, adeno-associated virus, retroviruses, and many others. Any suitable vector that transduces genetic material into a cell, and, if replication is desired, which is replicable and viable in the relevant host finds use in the present invention. In some embodiments, the construct further comprises regulatory sequences, including but not limited to a promoter, operably linked to the protein encoding sequence. Large numbers of suitable vectors and promoters are known to those of skill in the art. Indeed, in some embodiments, in order to obtain high levels of expression in a particular host it is often useful to express the EG1b variants of the present invention under the control of a heterologous promoter. In some embodiments, a promoter sequence is operably linked to the 5' region of the variant EG1b coding sequence using any suitable method known in the art. Examples of useful promoters for expression of EG1b variants include, but are not limited to promoters from fungi. In some embodiments, a promoter sequence that drives expression of a gene other than an EG1b gene in a fungal strain finds use. As a non-limiting example, a fungal promoter from a gene encoding an endoglucanase may be used. In some embodiments, a promoter sequence that drives the expression of an EG1b gene in a fungal strain other than the fungal strain from which the EG1b variants were derived finds use. Examples of other suitable promoters useful for directing the transcription of the nucleotide constructs of the present invention in a filamentous fungal host cell include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA). *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787, incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh 1, cbh2, egl1, egl2, pepA, hjb 1, hjb2, xyn1, amy, and glaA (See e.g., Nunberg et al., Mol. Cell Biol., 4:2306-2315 [1984]; Boel et al., EMBO J. 3:1581-85 [1984]; and European Patent Appln. 137280, all of which are incorporated herein by reference), and mutant, truncated, and hybrid promoters thereof. In a yeast host, useful promoters include, but are not limited to those from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH2/GAP), and *S. cerevisiae* 3-phosphoglycerate kinase. Additional useful promoters useful for yeast host cells are known in the art (See e.g., Romanos et al., Yeast 8:423-488 [1992], incorporated herein by reference). In addition, promoters associated with chitinase production in fungi find use in the present invention (See e.g., Blaiseau and Lafay, Gene 120243-248 [1992]; and Limon et al., Curr. Genet. 28:478-83 [1995], both of which are incorporated herein by reference).

In some embodiments, cloned EG1b variants of the present invention also have a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice finds use in the present invention. Exemplary transcription terminators for filamentous fungal host cells include, but are not limited to those obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease (See also, U.S. Pat. No. 7,399,627, incorporated herein by reference). In some embodiments, exemplary terminators for yeast host cells include those obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are well-known to those skilled in the art (See e.g., Romanos et al., Yeast 8:423-88 [1992]).

In some embodiments, a suitable leader sequence is part of a cloned EG1 b variant sequence, which is a nontranslated region of an mRNA that is important for translation by the host cell. The leader sequence is operably linked to the 5' terminus of the nucleic acid sequence encoding the polypeptide. Any leader sequence that is functional in the host cell of choice finds use in the present invention. Exemplary leaders for filamentous fungal host cells include, but are not limited to those obtained from the genes for *Aspergillus oryzae* TAKA amylase and *Aspergillus nidulans* triose phosphate isomerase. Suitable leaders for yeast host cells include, but are not limited to those obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

In some embodiments, the sequences of the present invention also comprise a polyadenylation sequence, which is a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice finds use in the present invention. Exemplary polyadenylation sequences for filamentous fungal host cells include, but are not limited to those obtained from the genes for *Aspergillus oryzae*TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are known in the art (See e.g., Guo and Sherman, Mol Cell Biol., 15:5983-5990 [1995]).

In some embodiments, the expression vector of the present invention contains one or more selectable markers, which permit easy selection of transformed cells. A "selectable marker" is a gene, the product of which provides for biocide or viral resistance, resistance to antimicrobials or heavy metals, prototrophy to auxotrophs, and the like. Any suitable selectable markers for use in a filamentous fungal host cell find use in the present invention, including, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Additional markers useful in host cells such as *Aspergillus*, include but are not limited to the amdS and pyrG genes of *Aspergillus nidulans* or *Aspergillus oryzae* and the bar gene of *Streptomyces hygroscopicus*. Suitable markers for yeast host cells include, but are not limited to ADE2, HIS3, LEU2, LYS2, MET3, TRP1, and URA3.

In some embodiments, a vector comprising a sequence encoding at least one EG1b variant is transformed into a host cell in order to allow propagation of the vector and expression of the EG1b variant(s). In some embodiments, the EG1b variants are post-translationally modified to remove the signal peptide and in some cases may be cleaved after secretion. In some embodiments, the transformed host cell described above is cultured in a suitable nutrient medium under conditions permitting the expression of the EG1b variant(s). Any suitable medium useful for culturing the host cells finds use in the present invention, including, but not limited to minimal or complex media containing appropriate supplements. In some embodiments, host cells are grown in HTP media. Suitable media are available from various commercial suppliers or may be prepared according to published recipes (e.g., in catalogues of the American Type Culture Collection).

In some embodiments, the host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycota, Zygomycota, Fungi imperfecti. In some embodiments, the fungal host cells are yeast cells and filamentous fungal cells. The filamentous fungal host cells of the present invention include all filamentous forms of the subdivision Eumycotina and Oomycota. Filamentous fungi are characterized by a vegetative mycelium with a cell wall composed of chitin, cellulose and other complex polysaccharides. The filamentous fungal host cells of the present invention are morphologically distinct from yeast.

In some embodiments of the present invention, the filamentous fungal host cells are of any suitable genus and species, including, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium*, and/or *Volvariella*, and/or teleomorphs, or anamorphs, and synonyms, basionyms, or taxonomic equivalents thereof.

In some embodiments of the present invention, the filamentous fungal host cell is of the *Trichoderma* species (e.g., *T. longibrachiatum, T. viride* [e.g., ATCC 32098 and 32086]), *Hypocrea jecorina* or *T. reesei* (NRRL 15709, ATTC 13631, 56764, 56765, 56466, 56767 and RL-P37 and derivatives thereof (See e.g., Sheir-Neiss et al., Appl. Microbiol. Biotechnol., 20:46-53 [1984]), *T. koningii*, and *T. harzianum*. In addition, the term "*Trichoderma*" refers to any fungal strain that was previously and/or currently classified as *Trichoderma*. In some embodiments of the present invention, the filamentous fungal host cell is of the *Aspergillus* species (e.g., *A. awamori. A. funigatus. A. japonicus, A. nidulans, A. niger, A. aculeatus, A. foetidus, A. oryzae, A. sojae*, and *A. kawachi*; See e.g., Kelly and Hynes, EMBO J., 4:475-479 [1985]; NRRL 3112, ATCC 11490, 22342, 44733, and 14331; Yelton et al., Proc. Natl. Acad. Sci. USA, 81, 1470-1474 [1984]; Tilbum et al., Gene 26:205-221 [1982]; and Johnston, et al., EMBO J., 4:1307-1311 [1985]). In some embodiments of the present invention, the filamentous fungal host cell is a *Chrysosporium* species (e.g., *C. lucknowense, C. keratinophilum, C. tropicum, C. merdarium, C. inops, C. pannicola*, and *C. zonatum*). In some embodiments of the present invention, the filamentous fungal host cell is a *Myceliophthora* species (e.g., *M. thermophila*). In some embodiments of the present invention, the filamentous fungal host cell is a *Fusarium* species (e.g., *F. bactridioides, F. cerealis, F. crookwellense, F. culmorum, F. graminearum, F. graminum, F oxysporum, F. roseum*, and *F. venenatum*). In some embodiments of the present invention, the filamentous fungal host cell is a *Neurospora* species (e.g., *N. crassa*; See e.g., Case et al., Proc. Natl. Acad. Sci. USA, 76:5259-5263 [1979]; U.S. Pat. No. 4,486,553; and Kinsey and Rambosek (1984) Mol. Cell. Biol., 4:117-122 [1984], all of which are hereby incorporated by reference).

In some embodiments of the present invention, the filamentous fungal host cell is a *Humicola* species (e.g., *H. insolens, H. grisea*, and *H. lanuginosa*). In some embodiments of the present invention, the filamentous fungal host cell is a *Mucor* species (e.g., *M. miehei* and *M. circinelloides*). In some embodiments of the present invention, the filamentous fungal host cell is a *Rhizopus* species (e.g., *R. oryzae* and *R. niveus.*). In some embodiments of the invention, the filamentous fungal host cell is a *Penicillium* species (e.g., *P. purpurogenum, P. chrysogenum*, and *P. verruculosum*). In some embodiments of the invention, the filamentous fungal host cell is a *Talaromyces* species (e.g., *T. emersonii, T. flavus, T. helicus, T. rotundus*, and *T. stipitatus*). In some embodiments of the invention, the filamentous fungal host cell is a *Thielavia* species (e.g., *T. terrestris* and *T. heterothallica*). In some embodiments of the present invention, the filamentous fungal host cell is a *Tolypocladium* species (e.g., *T. inflatum* and *T. geodes*). In some embodiments of the present invention, the filamentous fungal host cell is a *Trametes* species (e.g., *T. villosa* and *T. versicolor*). In some embodiments of the present invention, the filamentous fungal host cell is a *Sporotrichum* species. In some embodiments of the present invention, the filamentous fungal host cell is a *Corynascus* species.

In some embodiments of the present invention, the host cell is a yeast cell, including but not limited to cells of *Candida, Hansenula, Saccharomyces, Schizosaccharomyces, Pichia, Kluyveromyces*, or *Yarrowia* species. In some embodiments of the present invention, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

In some embodiments of the invention, the host cell is an algal cell such as *Chlamydomonas* (e.g., *C. reinhardtii*) and *Phormidium* (P. sp. ATCC29409).

In some other embodiments, the host cell is a prokaryotic cell. Suitable prokaryotic cells include, but are not limited to Gram-positive. Gram-negative and Gram-variable bacterial cells. Any suitable bacterial organism finds use in the present invention, including but not limited to *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactoacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* and *Zymomonas*. In some embodiments, the host cell is a species of *Agrobacterium, Acinetobacter, Azobacter, Bacillus, Bifidobacterium, Buchnera, Geobacillus, Campylobacter, Clostridium, Corynebacterium,*

*Escherichia, Enterococcus, Erwinia, Flavobacterium, Lactobacillus, Lactococcus, Pantoea, Pseudomonas, Staphylococcus, Salmonella, Streptococcus, Streptomyces,* or *Zymomonas.* In some embodiments, the bacterial host strain is non-pathogenic to humans. In some embodiments the bacterial host strain is an industrial strain. Numerous bacterial industrial strains are known and suitable in the present invention. In some embodiments of the present invention, the bacterial host cell is an *Agrobacterium* species (e.g., *A. radiobacter, A. rhizogenes,* and *A. rubi*). In some embodiments of the present invention, the bacterial host cell is an *Arthrobacter* species (e.g., *A. aurescens, A. citreus, A. globformis, A. hydrocarboglutamicus, A. mysorens, A. nicotianae, A. paraffineus, A. protophonniae, A. roseoparqffinus, A. sulfureus,* and *A. ureafaciens*). In some embodiments of the present invention, the bacterial host cell is a *Bacillus* species (e.g., *B. thuringensis, B. anthracis, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans,* and *B. amyloliquefaciens*). In some embodiments, the host cell is an industrial *Bacillus* strain including but not limited to *B. subtilis, B. pumilus, B. licheniformis, B. megaterium, B. clausii, B. stearothermophilus,* or *B. amyloliquefaciens.* In some embodiments, the *Bacillus* host cells are *B. subtilis, B. licheniformis, B. megaterium, B. stearothermophilus,* and/or *B. amyloliquefaciens.* In some embodiments, the bacterial host cell is a *Clostridium* species (e.g., *C. acetobutylicum, C. tetani* E88. *C. lituseburense, C. saccharobutylicum, C. perfringens,* and *C. beijerinckii*). In some embodiments, the bacterial host cell is a *Corynebacterium* species (e.g., *C. glutamicum* and *C. acetoacidophilum*). In some embodiments the bacterial host cell is a *Escherichia* species (e.g., *E. coli*). In some embodiments, the bacterial host cell is an *Erwinia* species (e.g., *E. uredovora, E. carotovora, E. ananas, E. herbicola, E. punctala,* and *E. terreus*). In some embodiments, the bacterial host cell is a *Pantoea* species (e.g., *P. citrea,* and *P. agglomerans*). In some embodiments the bacterial host cell is a *Pseudomonas* species (e.g., *P. putida, P. aeruginosa, P. mevalonii,* and P. sp. D-01 10). In some embodiments, the bacterial host cell is a *Streptococcus* species (e.g., *S. equisimiles, S. pyrogenes,* and *S. uberis*). In some embodiments, the bacterial host cell is a *Streptomyces* species (e.g., *S. ambofaciens, S. achromogenes, S. avermitilis, S. coelicolor, S. aureofaciens. S. aureus, S. fungicidicus, S. griseus,* and *S. lividans*). In some embodiments, the bacterial host cell is a *Zymomonas* species (e.g., *Z. mobilis,* and *Z. lipolytica*).

Many prokaryotic and eukaryotic strains that find use in the present invention are readily available to the public from a number of culture collections such as American Type Culture Collection (ATCC). Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

In some embodiments, host cells are genetically modified to have characteristics that improve protein secretion, protein stability and/or other properties desirable for expression and/or secretion of a protein. For example, knockout of Alp1 function results in a cell that is protease deficient. Knockout of pyr5 function results in a cell with a pyrimidine deficient phenotype. In some embodiments, the host cells are modified to delete endogenous cellulase protein-encoding sequences or otherwise eliminate expression of one or more endogenous cellulases. In some embodiments, expression of one or more endogenous cellulases is inhibited to increase production of cellulases of interest. Genetic modification can be achieved by genetic engineering techniques and/or classical microbiological techniques (e.g., chemical or UV mutagenesis and subsequent selection). Indeed, in some embodiments, combinations of recombinant modification and classical selection techniques are used to produce the host cells. Using recombinant technology, nucleic acid molecules can be introduced, deleted, inhibited or modified, in a manner that results in increased yields of EG1b variants within the host cell and/or in the culture medium. For example, knockout of Alp1 function results in a cell that is protease deficient, and knockout of pyr5 function results in a cell with a pyrimidine deficient phenotype. In one genetic engineering approach, homologous recombination is used to induce targeted gene modifications by specifically targeting a gene in vivo to suppress expression of the encoded protein. In alternative approaches, siRNA, antisense and/or ribozyme technology find use in inhibiting gene expression.

In some embodiments, host cells (e.g., *Myceliophthora thermophila*) used for expression of EG1b variants have been genetically modified to reduce the amount of endogenous cellobiose dehydrogenase (EC 1.1.3.4) and/or other enzymes activity that is secreted by the cell. A variety of methods are known in the art for reducing expression of protein in cells, including, but not limited to deletion of all or part of the gene encoding the protein and site-specific mutagenesis to disrupt expression or activity of the gene product. (See e.g., Chaveroche et al., Nucl. Acids Res., 28:22 e97 [2000]; Cho et al., MPMI 19: 1:7-15 [2006]; Maruyama and Kitamoto, Biotechnol Lett., 30:1811-1817 [2008]; Takahashi et al., Mol. Gen. Genom., 272: 344-352 [2004]; and You et al., Arch Micriobiol., 191:615-622 [2009], all of which are incorporated by reference herein). Random mutagenesis, followed by screening for desired mutations also finds use (See e.g., Combier et al., FEMS Microbiol Lett 220:141-8 [2003]; and Firon et al., Eukary. Cell 2:247-55 [2003], both of which are incorporated by reference). In some embodiments, the host cell is modified to reduce production of endogenous cellobiose dehydrogenases. In some embodiments, the cell is modified to reduce production of cellobiose dehydrogenase (e.g., CDH1 or CDH2). In some embodiments, the host cell has less than 75%, sometimes less than 50%, sometimes less than 30%, sometimes less than 25%, sometimes less than 20%, sometimes less than 15%, sometimes less than 10%, sometimes less than 5%, and sometimes less than 1% of the cellobiose dehydrogenase (e.g., CDH1 and/or CDH2) activity of the corresponding cell in which the gene is not disrupted. Exemplary *Myceliophthora thermophila* cellobiose dehydrogenases include, but are not limited to CDH 1 and CDH2. The genomic sequence for the Cdh1 encoding CDH1 has accession number AF074951.1. In one approach, gene disruption is achieved using genomic flanking markers (See e.g., Rothstein, Meth. Enzymol., 101:202-11 [1983]). In some embodiments, site-directed mutagenesis is used to target a particular domain of a protein, in some cases, to reduce enzymatic activity (e.g., glucose-methanol-choline oxido-reductase N and C domains of a cellobiose dehydrogenase or heme binding domain of a cellobiose dehydrogenase; See e.g., Rotsaert et al., Arch. Biochem. Biophys., 390:206-14 [2001], which is incorporated by reference herein in its entirety).

Introduction of a vector or DNA construct into a host cell can be accomplished using any suitable method known in the art, including but not limited to calcium phosphate transfection, DEAE-Dextran mediated transfection, PEGmediated transformation, electroporation, *Agrobacterium*-mediated transformation, and/or other common techniques known in the art.

In some embodiments, the engineered host cells (i.e., "recombinant host cells") of the present invention are cultured in conventional nutrient media modified as appropriate for activating promoters, selecting transformants, or amplifying the cellobiohydrolase polynucleotide. Culture conditions, such as temperature, pH and the like, are those previously used with the host cell selected for expression, and are well-known to those skilled in the art. As noted, many standard references and texts are available for the culture and production of many cells, including cells of bacterial, plant, animal (especially mammalian) and archebacterial origin.

In some embodiments, cells expressing the EG1b variant polypeptides of the invention are grown under batch or continuous fermentations conditions. Classical "batch fermentation" is a closed system, wherein the compositions of the medium is set at the beginning of the fermentation and is not subject to artificial alternations during the fermentation. A variation of the batch system is a "fed-batch fermentation" which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. "Continuous fermentation" is an open system where a defined fermentation medium is added continuously to a bioreactor and an amount of conditioned medium is removed simultaneously for processing. In some embodiments, an equal amount of conditioned medium is simultaneously removed. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments of the present invention, cell-free transcription/translation systems find use in producing EG1b. Several systems are commercially available and the methods are well-known to those skilled in the art.

The present invention provides methods of making EG1b variant polypeptides or biologically active fragments thereof. In some embodiments, the method comprises: providing a host cell transformed with a polynucleotide encoding an amino acid sequence that comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprising at least one mutation as provided herein: culturing the transformed host cell in a culture medium under conditions in which the host cell expresses the encoded variant EG1b polypeptide; and optionally recovering or isolating the expressed EG1b variant polypeptide, and/or recovering or isolating the culture medium containing the expressed EG1b variant polypeptide. In some embodiments, the methods further provide optionally lysing the transformed host cells after expressing the encoded EG1b variant polypeptide and optionally recovering and/or isolating the expressed EG1b variant polypeptide from the cell lysate. The present invention further provides methods of making an EG1b variant polypeptide comprising cultivating a host cell transformed with an EG1b variant polypeptide under conditions suitable for the production of the variant EG1b polypeptide and recovering the EG1b polypeptide. Typically, recovery or isolation of the variant EG1b polypeptide is from the host cell culture medium, the host cell or both, using protein recovery techniques that are well known in the art, including those described herein. In some embodiments, host cells are harvested by centrifugation, disrupted by physical or chemical means, and the resulting crude extract retained for further purification. Microbial cells employed in expression of proteins can be disrupted by any convenient method, including, but not limited to freeze-thaw cycling, sonication, mechanical disruption, and/or use of cell lysing agents, as well as many other suitable methods well known to those skilled in the art.

In some embodiments, the resulting polypeptide is recovered/isolated and optionally purified by any of a number of methods known in the art. For example, in some embodiments, the polypeptide is isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. In some embodiments, protein refolding steps are used, as desired, in completing the configuration of the mature protein. In addition, in some embodiments, high performance liquid chromatography (HPLC) is employed in the final purification steps. For example, in some embodiments, methods for purifying BGL1 known in the art, find use in the present invention (See e.g., Parry et al., Biochem. J., 353:117 [2001]; and Hong et al., Appl. Microbiol. Biotechnol., 73:1331 [2007], both incorporated herein by reference). Indeed, any suitable purification methods known in the art find use in the present invention.

In some embodiments, immunological methods are used to purify EG1b variants. In one approach, antibody raised against an EG1b variant polypeptide (e.g., against a polypeptide comprising any of SEQ ID NOS:2, 5, 7, and/or 9, and/or an immunogenic fragment thereof) using conventional methods is immobilized on beads, mixed with cell culture media under conditions in which the EG1b variant is bound, and precipitated. In a related approach, immunochromatography finds use.

In some embodiments, the EG1b variants are expressed as a fusion protein including a non-enzyme portion. In some embodiments, the EG1b variant sequence is fused to a purification facilitating domain. As used herein, the term "purification facilitating domain" refers to a domain that mediates purification of the polypeptide to which it is fused. Suitable purification domains include, but are not limited to metal chelating peptides, histidine-tryptophan modules that allow purification on immobilized metals, a sequence which binds glutathione (e.g., GST), a hemagglutinin (HA) tag (corresponding to an epitope derived from the influenza hemagglutinin protein; See e.g., Wilson et al., Cell 37:767 [1984]), maltose binding protein sequences, the FLAG epitope utilized in the FLAGS extension/affinity purification system (e.g., the system available from Inmunex Corp, Seattle, Wash.), and the like. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography; See e.g., Porath et al., Prot. Exp. Purif., 3:263-281 [1992]) while the enterokinase cleavage site provides a means for separating the EG1b variant polypeptide from the fusion protein. pGEX vectors (Promega; Madison, Wis.) may also be used to express foreign poxlypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

The EG1b variants and biologically active fragments thereof as described herein have multiple industrial applications, including but not limited to, sugar production (e.g., glucose syrups), biofuels production, textile treatment, pulp or paper treatment, bio-based chemical production, and applications in detergents and/or animal feed. A host cell containing at least one EG1b variant of the present invention finds use without recovery and purification of the recombinant EG1 b variant(s) (e.g., for use in a large scale biofermentor). Alternatively, recombinant EG1b variants are produced and purified from the host cell.

The EG1b variants provided herein are particularly useful in methods used to break down cellulose to smaller oligosaccharides, disaccharides and monosaccharides. In some embodiments, the EG1b variants are used in saccharification methods. In some embodiments, the EG1b variants are used in combination with other cellulase enzymes in conventional enzymatic saccharification methods, to produce fermentable sugars. In some embodiments, the present invention provides methods for producing at least one end-product from a cellulosic substrate, the methods comprising contacting the cellulosic substrate with at least one EG1b variant as described herein (and optionally other cellulases) under conditions in which fermentable sugars are produced. The fermentable sugars are then used in a fermentation reaction comprising a microorganism (e.g., a yeast) to produce at least one end-product. In some embodiments, the methods further comprise pretreating the cellulosic substrate to increase its susceptibility to hydrolysis prior to contacting the cellulosic substrate with at least one EG1b variant (and optionally other cellulases).

In some embodiments, enzyme compositions comprising at least one EG1b variant of the present invention are reacted with a biomass substrate in the range of about 25° C. to about 100° C. about 30° C. to about 90° C., about 30° C. to about 80° C., or about 30° C. to about 70° C. Also the biomass may be reacted with the enzyme compositions at about 25° C., at about 30° C. at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C., and at about 100° C. Generally the pH range will be from about pH 3.0 to about 8.5, about pH 3.5 to about 8.5, about pH 4.0 to about 7.5, about pH 4.0 to about 7.0 and about pH 4.0 to about 6.5. In some embodiments, the incubation time varies (e.g., from about 1.0 to about 240 hours, from about 5.0 to about 180 hrs and from about 10.0 to about 150 hrs). In some embodiments, the incubation time is at least about 1 hr, at least about 5 hrs, at least about 10 hrs, at least about 15 hrs, at least about 25 hrs, at least about 50 hr, at least about 100 hrs, at least about 180 hrs. etc. In some embodiments, incubation of the cellulase under these conditions and subsequent contact with the substrate results in the release of substantial amounts of fermentable sugars from the substrate (e.g., glucose when the cellulase is combined with β-glucosidase). For example, in some embodiments, at least about 20%, at least about 30%, at least about 40%, at least about 50%, at least about 60%, at least about 70%, at least about 80%, at least about 90% or more fermentable sugar is available as compared to the release of sugar by a reference enzyme.

In some embodiments, an "end-product of fermentation" is any product produced by a process including a fermentation step using a fermenting organism. Examples of end-products of a fermentation include, but are not limited to, alcohols (e.g., fuel alcohols such as ethanol and butanol), organic acids (e.g., citric acid, acetic acid, acrylic acid, lactic acid, gluconic acid, and succinic acid), glycerol, ketones, diols, amino acids (e.g., glutamic acid), antibiotics (e.g. penicillin and tetracycline), vitamins (e.g., beta-carotene and B12), hormones, and fuel molecules other than alcohols (e.g., hydrocarbons).

In some embodiments, the fermentable sugars produced by the methods of the present invention are used to produce at least one alcohol (e.g., ethanol, butanol, etc.). The EG1b variants of the present invention find use in any method suitable for the generation of alcohols or other biofuels from cellulose. It is not intended that the present invention be limited to the specific methods provided herein. Two methods commonly employed are separate saccharification and fermentation (SHF) methods (See e.g., Wilke et al., Biotechnol. Bioengin., 6:155-75 [1976]) and simultaneous saccharification and fermentation (SSF) methods (See e.g. U.S. Pat. Nos. 3,990,944 and 3,990,945). In some embodiments, the SHF saccharification method comprises the steps of contacting a cellulase with a cellulose containing substrate to enzymatically break down cellulose into fermentable sugars (e.g., monosaccharides such as glucose), contacting the fermentable sugars with an alcohol-producing microorganism to produce alcohol (e.g., ethanol or butanol) and recovering the alcohol. In some embodiments, the method of consolidated bioprocessing (CBP) finds use, in which the cellulase production from the host is simultaneous with saccharification and fermentation either from one host or from a mixed cultivation. In addition, SSF methods find use in the present invention. In some embodiments, SSF methods provide a higher efficiency of alcohol production than that provided by SHF methods (See e.g., Drissen et al., Biocat. Biotrans., 27:27-35 [2009]).

In some embodiments, for cellulosic substances to be effectively used as substrates for the saccharification reaction in the presence of a cellulase of the present invention, it is desirable to pretreat the substrate. Means of pretreating a cellulosic substrate are well-known in the art, including but not limited to chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms), and the present invention is not limited by such methods.

In some embodiments, any suitable alcohol-producing microorganism known in the art (e.g., *Saccharomyces cerevisiae*), finds use in the present invention for the fermentation of fermentable sugars to alcohols and other end-products. The fermentable sugars produced from the use of the EG1b variants provided by the present invention find use in the production of other end-products besides alcohols, including, but not limited to biofuels and/or biofuels compounds, acetone, amino acids (e.g., glycine, lysine, etc.), organic acids (e.g., lactic acids, etc.), glycerol, ascorbic acid, diols (e.g., 1,3-propanediol, butanediol, etc.), vitamins, hormones, antibiotics, other chemicals, and animal feeds. In addition, the EG1b variants provided herein further find use in the pulp and paper industry. Indeed, it is not intended that the present invention be limited to any particular end-products.

In some embodiments, the present invention provides an enzyme mixture that comprises at least one EG1b variant polypeptide as provided herein. The enzyme mixture may be cell-free, or in alternative embodiments, may not be separated from host cells that secrete an enzyme mixture component. A cell-free enzyme mixture typically comprises enzymes that have been separated from cells. Cell-free enzyme mixtures can be prepared by any of a variety of methodologies that are known in the art, such as filtration or centrifugation methodologies. In some embodiments, the enzyme mixtures are partially cell-free, substantially cell-free, or entirely cell-free.

In some embodiments, at least one EG1b variant and any additional enzymes present in the enzyme mixture are secreted from a single genetically modified fungal cell or by different microbes in combined or separate fermentations. Similarly, in additional embodiments, the EG1b variant(s) and any additional enzymes present in the enzyme mixture are expressed individually or in sub-groups from different strains of different organisms and the enzymes are combined in it, to make the enzyme mixture. It is also contemplated that the EG1b variant(s) and any additional enzymes in the enzyme mixture will be expressed individually or in sub-groups from different strains of a single organism, and the enzymes combined to make the enzyme mixture. In some embodiments, all of the enzymes are expressed from a single host organism, such as a genetically modified fungal cell.

In some embodiments, the enzyme mixture comprises at least one cellulase, selected from cellobiohydrolase (CBH), endoglucanase (EG), glycoside hydrolase 61 (GH61) and/or beta-glucosidase (BGL). In some embodiments, the cellobiohydrolase is *T. reesei* cellobiohydrolase II. In some embodiments, the endoglucanase comprises a catalytic domain derived from the catalytic domain of a *Streptomyces avermitilis* endoglucanase. In some embodiments, at least one cellulase is *Acidothermus cellulolyticus, Thermobifida fusca, Humicola grisea*, and/or a *Chrysosporium* sp. cellulase. Cellulase enzymes of the cellulase mixture work together in decrystallizing and hydrolyzing the cellulose from a biomass substrate to yield fermentable sugars, such as but not limited to glucose (See e.g., Brigham et al. in Wyman ([ed.], Handbook on Bioethanol, Taylor and Francis, Washington D.C. [1995], pp 119-141, incorporated herein by reference). Indeed, it is not intended that the present invention be limited to any enzyme compositions comprising any particular cellulase component(s), as various combinations of cellulases find use in the enzyme compositions of the present invention.

Cellulase mixtures for efficient enzymatic hydrolysis of cellulose are known (See e.g., Viikari et al., Adv. Biochem. Eng. Biotechnol., 108:121-45 [2007]; and US Pat. Publns. 2009/0061484; US 2008/0057541; and US 2009/0209009, each of which is incorporated herein by reference). In some embodiments, mixtures of purified naturally occurring or recombinant enzymes are combined with cellulosic feedstock or a product of cellulose hydrolysis. In some embodiments, one or more cell populations, each producing one or more naturally occurring or recombinant cellulases, are combined with cellulosic feedstock or a product of cellulose hydrolysis.

In some embodiments, at least one EG1b variant polypeptide of the present invention is present in mixtures comprising enzymes other than cellulases that degrade cellulose, hemicellulose, pectin, and/or lignocellulose.

Cellulase mixtures for efficient enzymatic hydrolysis of cellulose are known (See e.g., Viikari et al., Adv. Biochem. Eng. Biotechnol., 108:121-45 [2007]; and US Pat. Publns. 2009/0061484; US 2008/0057541; and US 2009/0209009, each of which is incorporated herein by reference). In some embodiments, mixtures of purified naturally occurring or recombinant enzymes are combined with cellulosic feedstock or a product of cellulose hydrolysis. In some embodiments, one or more cell populations, each producing one or more naturally occurring or recombinant cellulases, are combined with cellulosic feedstock or a product of cellulose hydrolysis.

In some additional embodiments, the present invention provides at least one EG1b variant and at least one endoxylanase. Endoxylanases (EC 3.2.1.8) catalyze the endohydrolysis of 1,4-β-D-xylosidic linkages in xylans. This enzyme may also be referred to as endo-1,4-β-xylanase or 1,4-β-D-xylan xylanohydrolase. In some embodiments, an alternative is EC 3.2.1.136, a glucuronoarabinoxylan endoxylanase, an enzyme that is able to hydrolyze 1,4 xylosidic linkages in glucuronoarabinoxylans.

In some additional embodiments, the present invention provides at least one EG1b variant and at least one beta-xylosidase. Beta-xylosidases (EC 3.2.1.37) catalyze the hydrolysis of 1,4-beta-D-xylans, to remove successive D-xylose residues from the non-reducing termini. This enzyme may also be referred to as xylan 1, beta-β-xylosidase, 1,4-beta-D-xylan xylohydrolase, exo-1,4-beta-xylosidase or xylobiase.

In some additional embodiments, the present invention provides at least one EG1b variant and at least one alpha-L-arabinofuranosidase. Alpha-L-arabinofuranosidases (EC 3.2.1.55) catalyze the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinotiranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

In some additional embodiments, the present invention provides at least one EG1b variant and at least one alpha-glucuronidase. Alpha-glucuronidases (EC 3.2.1.139) catalyze the hydrolysis of an alpha-D-glucuronoside to D-glucuronate and an alcohol.

In some additional embodiments, the present invention provides at least one EG1b variant and at least one acetylxylanesterase. Acetylxylanesterases (EC 3.1.1.72) catalyze the hydrolysis of acetyl groups from polymeric xylan, acetylated xylose, acetylated glucose, alpha-napthyl acetate, and p-nitrophenyl acetate.

In some additional embodiments, the present invention provides at least one EG1b variant and at least one feruloyl esterase. Feruloyl esterases (EC 3.1.1.73) have 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

In some additional embodiments, the present invention provides at least one EG1b variant and at least one coumaroyl esterase. Coumaroyl esterases (EC 3.1.1.73) catalyze a reaction of the form: coumaroyl-saccharide+ $H_2O$=coumarate+saccharide. In some embodiments, the saccharide is an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73 so may also be referred to as a feruloyl esterase.

In some additional embodiments, the present invention provides at least one EG1b variant and at least one alpha-galactosidase. Alpha-galactosidases (EC 3.2.1.22) catalyze the hydrolysis of terminal, non-reducing α-D-galactose residues in α-D-galactosides, including galactose oligosaccharides, galactomannans, galactans and arabinogalactans. This enzyme may also be referred to as melibiase.

In some additional embodiments, the present invention provides at least one EG1b variant and at least one beta-galactosidase. Beta-galactosidases (EC 3.2.1.23) catalyze the hydrolysis of terminal non-reducing β-D-galactose residues in beta-D-galactosides. In some embodiments, the polypeptide is also capable of hydrolyzing alpha-L-arabinosides. This enzyme may also be referred to as exo-(1->4)-β-D-galactanase or lactase.

In some additional embodiments, the present invention provides at least one EG1b variant and at least one beta-mannanase. Beta-mannanases (EC 3.2.1.78) catalyze the random hydrolysis of 1, 4-beta-D-mannosidic linkages in mannans, galactomannans and glucomannans. This enzyme may also be referred to as mannan endo-1,4-beta-mannosidase or endo-1,4-mannanase.

In some additional embodiments, the present invention provides at least one EG1b variant and at least one beta-mannosidase. Beta-mannosidases (EC 3.2.1.25) catalyze the hydrolysis of terminal, non-reducing beta-D-mannose residues in beta-D-mannosides. This enzyme may also be referred to as mannanase or mannase.

In some additional embodiments, the present invention provides at least one EG1b variant and at least one glucoamylase. Glucoamylases (EC 3.2.1.3) catalyzes the release of D-glucose from non-reducing ends of oligo- and polysaccharide molecules. Glucoamylase is also generally considered a type of amylase known as amylo-glucosidase.

In some additional embodiments, the present invention provides at least one EG1b variant and at least one amylase. Amylases (EC 3.2.1.1) are starch cleaving enzymes that degrade starch and related compounds by hydrolyzing the alpha-1.4 and/or alpha-1,6 glucosidic linkages in an endo- or an exo-acting fashion. Amylases include alpha-amylases (EC 3.2.1.1); beta-amylases (3.2.1.2), amylo-amylases (EC 3.2.1.3), alpha-glucosidases (EC 3.2.1.20), pullulanases (EC 3.2.1.41), and isoamylases (EC 3.2.1.68). In some embodiments, the amylase is an alpha-amylase.

In some embodiments one or more enzymes that degrade pectin are included in enzyme mixtures that comprise at least one EG1b variant of the present invention. A pectinase catalyzes the hydrolysis of pectin into smaller units such as oligosaccharide or monomeric saccharides. In some embodiments, the enzyme mixtures comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase and/or a xylogalacturonase.

In some additional embodiments, the present invention provides at least one EG1b variant and at least one endo-polygalacturonase. Endo-polygalacturonases (EC 3.2.1.15) catalyze the random hydrolysis of 1,4-alpha-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-alpha-1,4-galacturonide glycanohydrolase, endogalacturonase; endo-D-galacturonase or poly(1,4-alpha-D-galacturonide) glycanohydrolase.

In some additional embodiments, the present invention provides at least one EG1b variant and at least one pectin methyl esterase. Pectin methyl esterases (EC 3.1.1.11) catalyze the reaction: pectin+n $H_2O$=n methanol+pectate. The enzyme may also been known as pectinesterase, pectin demethoxylase, pectin methoxylase, pectin methylesterase, pectase, pectinoesterase or pectin pectylhydrolase.

In some additional embodiments, the present invention provides at least one EG1b variant and at least one endo-galactanase. Endo-galactanases (EC 3.2.1.89) catalyze the endohydrolysis of 1, 4-beta-D-galactosidic linkages in arabinogalactans. The enzyme may also be known as arabinogalactan endo-1,4-beta-galactosidase, endo-1,4-beta-galactanase, galactanase, arabinogalactanase or arabinogalactan 4-beta-D-galactanohydrolase.

In some additional embodiments, the present invention provides at least one EG1b variant and at least one pectin acetyl esterase. Pectin acetyl esterases catalyze the deacetylation of the acetyl groups at the hydroxyl groups of GalUA residues of pectin.

In some additional embodiments, the present invention provides at least one EG1b variant and at least one endo-pectin lyase. Endo-pectin lyases (EC 4.2.2.10) catalyze the eliminative cleavage of (1→4)-alpha-D-galacturonan methyl ester to give oligosaccharides with 4-deoxy-6-O-methyl-alpha-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-alpha-D-galacturonan lyase.

In some additional embodiments, the present invention provides at least one EG1b variant and at least one pectate lyase. Pectate lyases (EC 4.2.2.2) catalyze the eliminative cleavage of (1 →4)-alpha-D-galacturonan to give oligosaccharides with 4-deoxy-alpha-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, alpha-1,4-D-endopolygalacturonic acid lyase, PGA lyase, PPase-N, endo-alpha-1,4-polygalacturonic acid lyase, polygalacturonic acid lyase, pectin trans-eliminase, polygalacturonic acid trans-eliminase or (1→4)-alpha-D-galacturonan lyase.

In some additional embodiments, the present invention provides at least one EG1b variant and at least one alpha-rhamnosidase. Alpha-rhamnosidases (EC 3.2.1.40) catalyze the hydrolysis of terminal non-reducing alpha-L-rhamnose residues in alpha-L-rhamnosides or alternatively in rhamnogalacturonan. This enzyme may also be known as alpha-L-rhamnosidase T, alpha-L-rhamnosidase N or alpha-L-rhamnoside rhamnohydrolase.

In some additional embodiments, the present invention provides at least one EG1b variant and at least one exo-galacturonase. Exo-galacturonases (EC 3.2.1.82) hydrolyze pectic acid from the non-reducing end, releasing digalacturonate. The enzyme may also be known as exo-poly-α-galacturonosidase, exopolygalacturonosidase or exopolygalacturanosidase.

In some additional embodiments, the present invention provides at least one EG1b variant and at least one exo-galacturan 1,4-alpha galacturonidase. Exo-galacturonases (EC 3.2.1.67) catalyze a reaction of the following type: (1,4-alpha-D-galacturonide)n+$H_2O$=(1,4-alpha-D-galacturonide)n-i+D-galacturonate. The enzyme may also be known as poly[1->4) alpha-D-galacturonide]galacturonohydrolase, exopolygalacturonase, poly(galacturonate) hydrolase, exo-D-galacturonase, exo-D-galacturonanase, exopoly-D-galacturonase or poly(1,4-alpha-D-galacturonide) galacturonohydrolase.

In some additional embodiments, the present invention provides at least one EG1b variant and at least one exopolygalacturonate lyase. Exopolygalacturonate lyases (EC 4.2.2.9) catalyze eliminative cleavage of 4-(4-deoxy-alpha-D-galact-4-enuronosyl)-D-galacturonate from the reducing end of pectate (i.e., de-esterified pectin). This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-alpha-D-galacturonan reducing-end-disaccharide-lyase.

In some additional embodiments, the present invention provides at least one EG1b variant and at least one rhamnogalacturonanase. Rhamnogalacturonanases hydrolyze the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

In some additional embodiments, the present invention provides at least one EG1b variant and at least one rhamnogalacturonan lyase. Rhamnogalacturonan lyases cleave alpha-L-Rhap-(1 →4)-alpha-D-GalpA linkages in an endo-fashion in rhamnogalacturonan by beta-elimination.

In some additional embodiments, the present invention provides at least one EG1b variant and at least one rhamnogalacturonan acetyl esterase. Rhamnogalacturonan acetyl esterases catalyze the deacetylation of the backbone of alternating rhanmnose and galacturonic acid residues in rhamnogalacturonan.

In some additional embodiments, the present invention provides at least one EG1b variant and at least one rhamnogalacturonan galacturonohydrolase. Rhamnogalacturonan galacturonohydrolases hydrolyze galacturonic acid from the non-reducing end of strictly alternating rhamnogalacturonan structures in an exo-fashion. This enzyme may also be known as xylogalacturonan hydrolase.

In some additional embodiments, the present invention provides at least one EG1 b variant and at least one endo-arabinanase. Endo-arabinanases (EC 3.2.1.99) catalyze endohydrolysis of 1,5-alpha-arabinofuranosidic linkages in 1,5-arabinans. The enzyme may also be known as endo-arabinase, arabinan endo-1,5-alpha-L-arabinosidase, endo-1,5-alpha-L-arabinanase, endo-alpha-1,5-arabanase; endo-arabanase or 1,5-alpha-L-arabinan 1,5-alpha-L-arabinanohydrolase.

In some additional embodiments, the present invention provides at least one EG1b variant and at least one enzyme that participate in lignin degradation in an enzyme mixture. Enzymatic lignin depolymerization can be accomplished by lignin peroxidases, manganese peroxidases, laccases and cellobiose dehydrogenases (CDH), often working in synergy. These extracellular enzymes are often referred to as "lignin-modifying enzymes" or "LMEs." Three of these enzymes comprise two glycosylated heme-containing peroxidases: lignin peroxidase (LIP); Mn-dependent peroxidase (MNP); and, a copper-containing phenoloxidase laccase (LCC).

In some additional embodiments, the present invention provides at least one EG1b variant and at least one laccase. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

In some additional embodiments, the present invention provides at least one EG1b variant and at least one Mn-dependent peroxidase. The enzymatic activity of Mn-dependent peroxidase (MnP) in is dependent on Mn2+. Without being bound by theory, it has been suggested that the main role of this enzyme is to oxidize Mn2+ to Mn3+(See e.g., Glenn et al., Arch. Biochem. Biophys., 251:688-696 [1986]). Subsequently, phenolic substrates are oxidized by the Mn3+ generated.

In some additional embodiments, the present invention provides at least one EG1b variant and at least one lignin peroxidase. Lignin peroxidase is an extracellular heme that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being hound by theory, has been proposed to function as a physiological redox mediator in the LiP-catalyzed oxidation of lignin in vivo (See e.g., Harvey, et al., FEBS Lett., 195:242-246 [1986]).

In some additional embodiments, the present invention provides at least one EG1b variant and at least one protease, amylase, glucoamylase, and/or a lipase that participates in cellulose degradation.

As used herein, the term "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the present invention. Some suitable proteases include, but are not limited to cysteine proteases including pepsin, papain and serine proteases including chymotrypsins, carboxypeptidases and metalloendopeptidases.

As used herein, the term "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

In some additional embodiments, the present invention provides at least one EG1b variant and at least one expansin or expansin-like protein, such as a swollenin (See e.g., Salheimo el al., Eur. J. Biochem., 269:4202-4211 [2002]) or a swollenin-like protein. Expansins are implicated in loosening of the cell wall structure during plant cell growth. Expansins have been proposed to disrupt hydrogen bonding between cellulose and other cell wall polysaccharides without comprising hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. In some embodiments, an expansin-like protein or swollenin-like protein comprises one or both of such domains and/or disrupts the structure of cell walls (such as disrupting cellulose structure), optionally without producing detectable amounts of reducing sugars.

In some additional embodiments, the present invention provides at least one EG1b variant and at least one polypeptide product of a cellulose integrating protein, scaffoldin or a scaffoldin-like protein, for example CipA or CipC from *Clostridium thermocellum* or *Clostridium cellulolyticum*respectively. Scaffoldins and cellulose integrating proteins are multi-functional integrating subunits which may organize cellulolytic subunits into a multi-enzyme complex. This is accomplished by the interaction of two complementary classes of domain (i.e. a cohesion domain on scaffoldin and a dockerin domain on each enzymatic unit). The scaffoldin subunit also bears a cellulose-binding module that mediates attachment of the cellulosome to its substrate. A scaffoldin or cellulose integrating protein for the purposes of this invention may comprise one or both of such domains.

In some additional embodiments, the present invention provides at least one EG1b variant and at least one cellulose induced protein or modulating protein, for example as encoded by cip1 or cip2 gene or similar genes from *Trichoderma reesei* (See e.g., Foreman et al., J. Biol. Chem., 278:31988-31997 [2003]).

In some additional embodiments, the present invention provides at least one EG1b variant and at least one member of each of the classes of the polypeptides described above, several members of one polypeptide class, or any combination of these polypeptide classes to provide enzyme mixtures suitable for various uses.

In some embodiments, the enzyme mixture comprises other types of cellulases, selected from but not limited to cellobiohydrolase, endoglucanase, beta-glucosidase, and glycoside hydrolase 61 protein (GH61) cellulases. These enzymes may be wild-type or recombinant enzymes. In some embodiments, the cellobiohydrolase is a type 1 cellobiohydrolase (e.g., a *T. reesei* cellobiohydrolase 1). In some embodiments, the endoglucanase comprises a catalytic domain derived from the catalytic domain of a *Streptomyces avermitilis* endoglucanase (See e.g., US Pat. Appln. Pub. No. 2010/0267089, incorporated herein by reference). In some embodiments, the at least one cellulase is derived from *Acidothermus cellulolyticus, Thermobifida fusca, Humicola grisea, Myceliophthora thermophila, Chaetomium thermophilum, Acremonium* sp., *Thielavia* sp, *Trichoderma reesei. Aspergillus* sp., or a *Chrysosporium* sp. Cellulase enzymes in the cellulase mixtures work together resulting in decrystallization and hydrolysis of the cellulose from a biomass substrate to yield fermentable sugars, such as but not limited to glucose.

Some cellulase mixtures for efficient enzymatic hydrolysis of cellulose are known (See e.g., Viikari et al., Adv. Biochem. Eng. Biotechnol., 108:121-45 [2007]; and US Pat. Appln. Publn. Nos. US 2009/0061484, US 2008/0057541, and US 2009/0209009, each of which is incorporated herein by reference in their entireties). In some embodiments, mixtures of purified naturally occurring or recombinant enzymes are combined with cellulosic feedstock or a product of cellulose hydrolysis. Alternatively or in addition, one or more cell populations, each producing one or more naturally occurring or recombinant cellulases, are combined with cellulosic feedstock or a product of cellulose hydrolysis.

In some embodiments, the enzyme mixture comprises commercially available purified cellulases. Commercial cellulases are known and available (e.g., C2730 cellulase from *Trichoderma reesei* ATCC No. 25921 available from Sigma-Aldrich, Inc.).

In some embodiments, the enzyme mixture comprises at least one EG1b variant as provided herein and at least one or more cellobiohydrolase type 1a such as a CBH1a, CBH2b, endoglucanase (EG) such as a type 2 endoglucanase (EG2), wild-type EG1b, β-glucosidase (Bgl), and/or a glycoside hydrolase 61 protein (GH61). In some embodiments, at least about 2.5%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 35%, at least about 40%, at least about 45%, or at least about 50% of the enzyme mixture comprises at least one EG1b variant. In some embodiments, the enzyme mixture comprises at least one cellobiohydromlase type 1(e.g., CBH1a), cellobiohydrolase type 2 (e.g., CBH2b), and at least one EG1b variant, wherein the enzymes together comprise at least about 25%, at least about 30%, at least about 35%, at least about 40%, at least about 45%, at least about 50%, at least about 55%, at least about 60%, at least about 65%, at least about 70%, at least about 75%, or at least about 80% of the enzyme mixture. In some embodiments, the enzyme mixture further comprises at least one β-glucosidase (Bgl), in addition to at least one EG1b variant, CBH 1a, and CBH2b, wherein the four enzymes together comprise at least about 30%, at least about 35%, at least about 40%, at least about 45%, at least about 50%, at least about 55%, at least about 60%, at least about 65%, at least about 70%, at least about 75%, at least about 80%, or at least about 85% of the enzyme mixture. In some embodiments, the enzyme mixture further comprises at least one additional endoglucanase (e.g., EG2), in addition to at least one EG1b variant. CBH2b, CBH1a, and/or Bgl, wherein the five enzymes together comprise at least about 35%, at least about 40%, at least about 45%, at least about 50%, at least about 55%, at least about 60%, at least about 65%, at least about 70%, at least about 75%, at least about 80%, at least about 85%, or at least about 90% of the enzyme mixture.

In some embodiments, the enzyme mixture comprises at least one or a combination of at least one EG1b variant, wild-type EG1b, CBH2b, CBH1a, Bgl, EG2, and glycoside hydrolase 61protein (GH61), in any suitable proportion for the desired reaction. In some embodiments, the enzyme mixture composition comprises isolated cellulases in the following proportions by weight (wherein the total weight of the cellulases is 100%): about 20% to about 10% of EG1b (variant and/or wild-type), about 20% to about 10% of Bgl, about 30% to about 25% of CBH1a, about 10% to about 0% of GH61, and about 20% to about 25% of CBH2b. In some embodiments, the enzyme mixture composition comprises isolated cellulases in the following proportions by weight: about 20% to about 10% of EG1b (wild-type and/or variant), about 25% to about 15% of Bgl, about 20% to about 30% of CBH1a, about 10% to about 15% of GH61, and about 25% to about 30% of CBH2b. In some embodiments, the enzyme mixture composition comprises isolated cellulases in the following proportions by weight: about 10% to about 15% of EG1b (wild-type and/or variant), about 20% to about 25% of Bgl, about 30% to about 20% of CBH1a, about 15% to about 5% of GH61, and about 25% to about 35% of CBH2b. In some embodiments, the enzyme mixture composition comprises isolated cellulases in the following proportions by weight: about 15% to about 5% of EG1b (wild-type and/or variant), about 15% to about 10% of Bgl, about 45% to about 30% of CBH1a, about 25% to about 5% of GH61, and about 40% to about 10% of CBH2b. In some embodiments, the enzyme mixture composition comprises isolated cellulases in the following proportions by weight: about 10% of EG1b (wild-type and/or variant), about 15% of Bgl, about 40% of CBH1a, about 25% of GH61, and about 10% of CBH2b.

In some embodiments, the enzyme mixture composition comprises isolated cellulases in the following proportions by weight: about 5% to about 25% of EG1b, about 5% to about 15% of Bgl about 15% to about 45% of CBH1a, about 2.5% to about 50% of GH61, and about 10% to about 40% of CBH2b. In some embodiments, the enzyme mixture composition comprises isolated cellulases in the following proportions by weight: about 10% of EG1b, about 15% of Bgl, about 40% of CBH1a, about 25% of GH61, and about 10% of CBH2b. In some further embodiments, the enzyme mixture composition comprises isolated cellulases in the following proportions by weight: about 10% of EG1b, about 10% of BgL about 20% of CBH1a, about 45% of GH61, and about 15% of CBH2b. In some embodiments, the enzyme mixture comprises isolated cellulases in the following proportions by weight: about 12% EG1b, about 33% GH61, about 10% Bgl, about 22% CBH1a, and about 23% CBH2b/EG2. In some other embodiments, the enzyme mixture comprises cellulases in the following proportions by weight: about 9% EG1b, about 9% EG2, about 28% GH61, about 10% about BGL1, about 30% CBH1a and about 14% CBH2b. In some additional embodiments, the enzyme mixtures comprise at least one additional enzyme, including but not limited to xylanase, xylosidase, acetyl xylan esterase, ferulic acid esterase, galactosidase, pectinase, etc. It is not intended that the present invention be limited to any particular combination and/or concentration of enzymes. Indeed, any suitable combinations of cellulases and/or proportions of cellulases find use in various embodiments of the invention. In addition to the use of a single EG1b variant, any combination of EG1b variants provided herein find use in these embodiments, as well as combinations comprising wild-type EG1b.

In some embodiments, the enzyme component comprises more than one CBH2b, CBH1a, EG, Bgl, and/or GH61 enzyme (e.g., 2, 3 or 4 different variants) in addition to at least one EG1b variant, in any suitable combination. In some embodiments, an enzyme mixture composition of the invention further comprises at least one additional protein and/or enzyme. In some embodiments, enzyme mixture compositions of the present invention further comprise at least one additional enzyme other than Bgl, CBH1a, GH61, and/or CBH2b. In some embodiments, the enzyme mixture compositions of the invention further comprise at least one additional cellulase, other than the EG1b variants, EG2, Bgl, CBH a, GH61, and/or CBH2b variant recited herein. In some embodiments, the EG1b variant polypeptide of the invention is also present in mixtures with non-cellulase enzymes that degrade cellulose, hemicellulose, pectin, and/or lignocellulose.

In some embodiments, EG1b variant polypeptide of the present invention is used in combination with other optional ingredients such as at least one buffer, surfactant, and/or scouring agent. In some embodiments, at least one buffer is used with the EG1b variant polypeptide of the present invention (optionally combined with other enzymes) to maintain a desired pH within the solution in which the EG1b variant is employed. The exact concentration of buffer employed depends on several factors which the skilled artisan can determine. Suitable buffers are well known in the art. In some embodiments, at least one surfactant is used in with the EG1b variants(s) of the present invention. Suitable surfactants include any surfactant compatible with the EG1b variant(s) and, optionally, with any other enzymes being used in the mixture. Exemplary surfactants include anionic, non-ionic, and ampholytic surfactants. Indeed, it indeed that any suitable surfactant will find use in the present invention. Suitable anionic surfactants include, but are not limited to, linear or branched alkylbenzenesulfonates; alkyl or alkenyl ether sulfates comprising linear or branched alkyl groups or alkenyl groups; alkyl or alkenyl sulfates; olefinsulfonates; alkanesulfonates, and the like. Suitable counter ions for anionic surfactants include, for example, alkali metal ions, such as sodium and potassium; alkaline earth metal ions, such as calcium and magnesium; ammonium ion; and alkanolamines comprising from 1 to 3 alkanol groups of carbon number 2 or 3. Ampholytic surfactants suitable for use in the practice of the present invention include, for example, quaternary ammonium salt sulfonates, betaine-type ampholytic surfactants, and the like. Suitable nonionic surfactants generally include polyoxalkylene ethers, as well as higher fatty acid alkanolamides or alkylene oxide adduct thereof, fatty acid glycerine monoesters, and the like. Mixtures of surfactants also find use in the present invention, as is known in the art.

The foregoing and other aspects of the invention may be better understood in connection with the following non-limiting examples.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); ° C. (degrees Centigrade); DNA (deoxyribonucleic acid); RNA (ribonucleic acid); HPLC (high pressure liquid chromatography); MES (2-N-morpholino ethanesulfonic acid); FIOPC (fold improvements over positive control); YPD (10 g/L yeast extract, 20 g/L peptone, and 20 g/L dextrose); SOE-PCR (splicing by overlapping extension PCR); ARS (ARS Culture Collection or NRRL Culture Collection. Peoria, Ill.); Axygen (Axygen, Inc., Union City, Calif.); Lallemand (Lallemand Ethanol Technology, Milwaukee, Wis.); Dual Biosystems (Dual Biosystems AG, Schlieven, Switzerland); NEB (New England Biolabs, Ipswich, Mass.); Megazyme (Megazyme International Ireland. Ltd., Wicklow, Ireland); Sigma-Aldrich (Sigma-Aldrich, St. Louis. Mo.); Dasgip (Dasgip Biotools, LLC. Shrewsbury. Mass.); Difco (Difco Laboratories, BD Diagnostic Systems. Detroit, Mich.); PCRdiagnostics (PCRdiagnostics, by E coli SRO, Slovak Republic); Stratagene (Stratagene, now an Agilent Technologies company); Agilent (Agilent Technologies. Inc., Santa Clara, Calif.); Molecular Devices (Molecular Devices, Sunnyvale. Calif.); Symbio (Symbio. Inc., Menlo Park. Calif.); USBio (US Biological, Swampscott. Mass.); Qiagen (Qiagen Inc., Germantown. Md.); and Bio-Rad (Bio-Rad Laboratories, Hercules, Calif.).

The wild-type EG1b cDNA (SEQ ID NO:1) and amino acid (SEQ ID NO:2) sequences are provided below. The signal sequence is shown in bold in SEQ ID NO:2. SEQ ID NO:3 provides the sequence of EG1b, without the signal sequence. In addition, the backbone sequences used for rounds 2 through 4 of evolution are provided. The round 2 (Rd2) backbone polynucleotide sequence is provided as SEQ ID NO:4, while the polypeptide sequence is provided as SEQ ID NO:5. The round 3 (Rd3) backbone polynucleotide sequence is provided as SEQ ID NO:6, while the polypeptide sequence is provided as SEQ ID NO:7. The round 4 (Rd4) backbone polynucleotide sequence is provided as SEQ ID NO:8, while the polypeptide sequence is provided as SEQ ID NO:9.

(SEQ ID NO: 1)
```
ATGGGGCAGAAGACTCTCCAGGGGCTGGTGGCGGCGGCGGCACTGGCAGCCTCGGTGGCGAACGCGCA
GCAACCGGGCACCTTCACGCCCGAGGTGCATCCGACGCTGCCGACGTGGAAGTGCACGACGAGCGGCG
GGTGCGTCCAGCAGGACACGTCGGTGGTGCTCGACTGGAACTACCGCTGGTTCCACACCGAGGACGGT
AGCAAGTCGTGCATCACCTCTAGCGGCGTCGACCGGACCCTGTGCCCGGACGAGGCGACGTGCGCCAA
GAACTGCTTCGTCGAGGGCGTCAACTACACGAGCAGCGGGGTCGAGACGTCCGGCAGCTCCCTCACCC
TCCGCCAGTTCTTCAAGGGCTCCGACGGCGCCATCAACAGCGTCTCCCCGCGCGTCTACCTGCTCGGG
GGAGACGGCAACTATGTCGTGCTCAAGCTCCTCGGCCAGGAGCTGAGCTTCGACGTGGACGTATCGTC
GCTCCCGTGCGGCGAGAACGCGGCCCTGTACCTGTCCGAGATGGACGCGACGGGAGGACGGAACGAGT
ACAACACGGGCGGGGCCGAGTACGGGTCGGGCTACTGTGACGCCCAGTGCCCCGTGCAGAACTGGAAC
AACGGGACGCTCAACACGGGCCGGGTGGGCTCGTGCTGCAACGAGATGGACATCCTCGAGGCCAACTC
CAAGGCCGAGGCCTTCACGCCGCACCCCTGCATCGGCAACTCGTGCGACAAGAGCGGGTGCGGCTTCA
ACGCGTACGCGCGCGGTTACCACAACTACTGGGCCCCCGGCGGCACGCTCGACACGTCCCGGCCTTTC
ACCATGATCACCCGCTTCGTCACCGACGACGGCACCACCTCGGGCAAGCTCGCCCGCATCGAGCGCGT
CTACGTCCAGGACGGCAAGAAGGTGCCCAGCGCGGCGCCCGGGGGGACGTCATCACGGCCGACGGGT
GCACCTCCGCGCAGCCCTACGGCGCCTTTCCGGCATGGGCGACGCCCTCGGCCGCGGCATGGTCCTG
GCCCTGAGCATCTGGAACGACGCGTCCGGGTACATGAACTGGCTCGACGCCGGCAGCAACGGCCCTG
CAGCGACACCGAGGGTAACCCGTCCAACATCCTGGCCAACCACCCGGACGCCCACGTCGTGCTCTCCA
ACATCCGCTGGGGCGACATCGGCTCCACCGTCGACACCGGCGATGGCGACAACAACGGCGGCGGCCCC
CAACCCGTCATCCACCACCACCGCTACCGCTACCACCACCTCCTCCGGCCCGGCCGAGCCTACCCAGA
CCCACTACGGCCAGTGTGGAGGGAAAGGATGGACGGGCCCTACCCGCTGCGAGACGCCCTACACCTGC
AAGTACCAGAACGACTGGTACTCGCAGTGCCTGTAG
```

(SEQ ID NO: 2)
```
MGQKTLQGLVAAAALAASVANAQQPGTFTPEVHPTLPTWKCTTSGGCVQQDTSVVLDWNYRWFHTEDG
SKSCITSSGVDRTLCPDEATCAKNCFVEGVNYTSSGVETSGSSLTLRQFFKGSDGAINSVSPRVYLLG
GDGNYVVLKLLGQELSFDVDVSSLPCGENAALYLSEMDATGGRNEYNTGGAEYGSGYCDAQCPVQNWN
NGTLNTGRVGSCCNEMDILEANSKAEAFTPHPCIGNSCDKSGCGFNAYARGYHNYWAPGGTLDTSRPF
TMITRFVTDDGTTSGKLARIERVYVQDGKKVPSAAPGGDVITADGCTSAQPYGGLSGMGDALGRGMVL
ALSIWNDASGYMNWLDAGSNGPCSDTEGNPSNILANHPDAHVVLSNIRWGDIGSTVDTGDGDNNGGGP
NPSSTTTATATTTSSGPAEPTQTHYGQCGGKGWTGPTRCETPYTCKYQNDWYSQCL
```

(SEQ ID NO: 3)
```
QPGTFTPEVHPTLPTWKCTTSGGCVQQDTSVVLDWNYRWFHTEDGSKSCITSSGVDRTLCPDEATCAK
NCFVEGVNYTSSGVETSGSSLTLRQFFKGSDGAINSVSPRVYLLGGDGNYVVLKLLGQELSFDVDVSS
LPCGENAALYLSEMDATGGRNEYNTGGAEYGSGYCDAQCPVQNWNNGTLNTGRVGSCCNEMDILEANS
KAEFTPHPCIGNSCDKSGCGFNAYARGYHNYWAPGGTLDTSRPFTMITRFVTDDGTTSGKLARIERVY
VQDGKKVPSAAPGGDVITADGCTSAQPYGGLSGMGDALGRGMVLALSIWNDASGYMNWLDAGSNGPCS
DTEGNPSNILANHPDAHVVLSNIRWGDIGSTVDTGDGDNNGGGPNPSSTTTATATTTSSGPAEPTQTH
YGQCGGKGWTGPTRCETPYTCKYQNDWYSQCL
```

Round 2 Backbone:
(SEQ ID NO: 4)
```
ATGGGGCAGAAGACTCTCCAGGGGCTGGTGGCGGCGGCGGCACTGGCAGCCTCGGTGGCGAACGCGCA
GCAACCGGGCACCTTCACGCCCGAGGTGCATCCGACGCTGCCGACGTGGAAGTGCACGACGAGCGGCG
GGTGCGTCCAGCAGGACACGTCGGTGGTGCTCGACTGGAACTACCGCTGGATTCACACCGAGGACGGT
AGCAAGTCGTGCATCACCTCTAGCGGCGTCGACCGGACCCTGTGCCCGGACGAGGCGACGTGCGCCAA
GAACTGCTTCGTCGAGGGCGTCAACTACACGAGCAGCGGGGTCGAGACGTCCGGCAGCTCCCTCACCC
TCCGCCAGTTCTTCAAGGGCTCCGACGGCGCCATCAACAGCGTCTCCCCGCGCGTCTACCTGCTCGGG
GGAGACGGCAACTATGTCGTGCTCAAGCTCCTCGGCCAGGAGCTGAGCTTCGACGTGGACGTATCGTC
GCTCCCGTGCGGCGAGAACGCGGCCCTGTACCTGTCCGAGATGGACGCGACGGGAGGACGGAACGAGT
ACAACACGGGCGGGGCCGAGTACGGGTCGGGCTACTGTGACGCCCAGTGCCCCGTGCAGAACTGGAAC
AACGGGACGCTCAACACGGGCCGGGTGGGCTCGTGCTGCAACGAGATGGACATCCTCGAGGCCAACTC
CAAGGCCGAGGCCTTCACGCCGCACCCCTGCATCGGCAACTCGTGCGACAAGAGCGGGTGCGGCTTCA
ACGCGTACGCGCGCGGTTACCACAACTACTGGGCCCCCGGCGGCACGCTCGACACGTCCCGGCCTTTC
ACCATGATCACCCGCTTCGTCACCGACGACGGCACCACCTCGGGCAAGCTCGCCCGCATCGAGCGCGT
CTACGTCCAGGACGGCAAGAAGGTGCCCAGCGCGGCGCCCGGGGGGACGTCATCACGGCCGACGGGT
GCACCTCCGCGCAGCCCTACGGCGGCCTTTCCGGCATGGGCGACGCCCTCGGCCGCGGCATGGTCCTG
GCCCTGAGCATCTGGAACGACGCGTCCGGGTACATGAACTGGCTCGACGCCGGCAGCAACGGCCCTG
CAGCGACACCGAGGGTAACCCGTCCAACATCCTGGCCAACCACCCGGACGCCCACGTCGTGCTCTCCA
ACATCCGCTGGGGCGACATCGGCTCCACCGTCGACACCGGCGATGGCGACAACAACGGCGGCGGCCCC
AACCCGTCATCCACCACCACCGCTACCGCTACCACCACCTCCTCCGGCCCGGCCGAGCCTACCCAGAC
CCACTACGGCCAGTGTGGAGGGAAAGGATGGACGGGCCCTACCCGCTGCGAGACGCCCTACACCTGCA
AGTACCAGAACGACTGGTACTCGCAGTGCCTGTAG
```

(SEQ ID NO: 5)
```
MGQKTLQGLVAAAALAASVANAQQPGTFTPEVHPTLPTWKCTTSGGCVQQDTSVVLDWNYRWIHTEDG
SKSCITSSGVDRTLCPDEATCAKNCFVEGVNYTSSGVETSGSSLTLRQFFKGSDGAINSVSPRVYLLG
GDGNYVVLKLLGQELSFDVDVSSLPCGENAALYLSEMDATGGRNEYNTGGAEYGSGYCDAQCPVQNWN
NGTLNTGRVGSCCNEMDILEANSKAEAFTPHPCIGNSCDKSGCGFNAYARGYHNYWAPGGTLDTSRPF
TMITRFVTDDGTTSGKLARIERVYVQDGKKVPSAAPGGDVITADGCTSAQPYGGLSGMGDALGRGMVL
ALSIWNDASGYMNWLDAGSNGPCSDTEGNPSNILANHPDAHVVLSNIRWGDIGSTVDTGDGDNNGGGP
NPSSTTTATATTTSSGPAEPTQTHYGQCGGKGWTGPTRCETPYTCKYQNDWYSQCL
```

-continued

Round 3 Backbone:

(SEQ ID NO: 6)
ATGGGGCAGAAGACTCTCCAGGGGCTGGTGGCGGCGGCGGCACTGGCAGCCTCGGTGGCGAACGCGCA
GCAACCGGGCACCTTCACGCCCGAGGTGCATCCGACGCTGCCGACGTGGAAGTGCACGACGAGCGGCG
GGTGCGTCCAGCAGGACACGTCGGTGGTGCTCGACTGGAACTACCGCTGGATTCACACCCGTGACGGT
AGCAAGTCGTGCATCACCTCTAGCGGCGTCGACCGGACCCTGTGCCCGGACGAGGCGACGTGCGCCAA
GAACTGCTTCGTCGAGGGCGTCAACTACACGAGCAGCGGGGTCGAGACGTCCGGCAGCTCCCTCACCC
TCCGCCAGTTCTTCAAGGGCTCCGACGGCGCCATCAACAGCGTCTCCCCGCGCGTCTACCTGCTCGGG
GGAGACGGCAACTATGTCGTGCTCAAGCTCCTCGGCCAGGAGCTGAGCTTCGACGTGGACGTATCGTC
GCTCCCCGTGCGGCGAGAACGCGGCCCTGTACCTGTCCGAGATGGACGCGACGGGAGGACGGAACGAGT
ACAACACGGGCGGGGCCGAGTACGGGTCGGGCTACTGTGACGCCCAGTGCCCCGTGATGAACTGGAAC
AACGGGACGCTCAACACGGGCCGGGTGGGCTCGTGCTGCAGCGAGATGGACATCCTCGAGGCCAACTC
CTTTGCCGAGGCCTTCACGCCGCACCCCTGCATCGGCAACTCTGTGCGACAAGAGCGGGTGCGGCTTCA
ACGCGTACGCGCGCGGTTACCACAACTACTGGGCCCCCGGCGGCACGCTCGACACGTCCCGGCCTTTC
ACCGTGATCACCCGCTTCGTCACCGACGACGGCACCCACCTCGGGCAAGCTCGCCCGCATCGAGCGCGT
CTACGTCCAGGACGGCAAGAAGGTGCCCAGCGCGGCGCCCGGGGGGACGTCATCACGGCCGACGGGT
GCACCTCCGCGCAGCCCTACGGCGGCCTTTCCGGCATGGGCGACGCCCTCGGCCGCGGGCATGGTCCTG
GCCCTGAGCATCTGGAACGACGCGTCCACCTACATGAACTGGCTCGACGCCGGCAGCAACGGCCCCTG
CAGCGACACCGAGGGTAACCCGTCCAACATCCTGGCCAACCACCCGGACGCCCACGTCGTGCTCTCCA
ACATCCGCTGGGGCGACATCGGCTCCACCGTCGACACCGGCGATGGCGACAACAACGGCGGCGGCCCC
AACCCGTCATCCACCACCACCGCTACCGCTACCACCACCTCCTCCGGCCCGGCCGAGCCTACCCAGAC
CCACTACGGCCAGTGTGGAGGGAAAGGATGGACGGGCCCTACCCGCTGCGAGACGCCCTACACCTGCA
AGTACCAGAACGACTGGTACTCGCAGTGCCTGTAG (SEQ ID NO: 7)
MGQKTLQGLVAAAALAASVANAQQPGTFTPEVHPTLPTWKCTTSGGCVQQDTSVVLDWNYRWIHTRDG
SKSCITSSGVDRTLCPDEATCAKNCFVEGVNYTSSGVETSGSSLTLRQFFKGSDGAINSVSPRVYLLG
GDGNYVVLKLLGQELSFDVDVSSLPCGENAALYLSEMDATGGRNEYNTGGAEYGSGYCDAQCPVMNWN
NGTLNTGRVGSCCSEMDILEANSFAEAFTPHPCIGNSCDKSGCGFNAYARGYHNYWAPGGTLDTSRPF
TVITRFVTDDGTTSGKLARIERVYVQDGKKVPSAAPGGDVITADGCTSAQPYGGLSGMGDALGRGMVL
ALSIWNDASTYMNWLDAGSNGPCSDTEGNPSNILANHPDAHVVLSNIRWGDIGSTVDTGDGDNNGGGP
NPSSTTTATATTTSSGPAEPTQTHYGQCGGKGWTGPTRCETPYTCKYQNDWYSQCL

Round 4 Backbone:

(SEQ ID NO: 8)
ATGGGGCAGAAGACTCTCCAGGGGCTGGTGGCGGCGGCGCAACTGGCAGCCTCGGTGGCGAACGCGCA
GCAACCGGGCACCTTCACGCCCGAGGTGCATCCGACGCTGCCGACGTGGAAGTGCACGACGAGCGGCG
GGTGCGTCCAGCAGGACACGTCGGTGGTGCTCGACTGGAACTACCGCTGGATTCACACCCGTGACGGT
AGCAAGTCGTGCATCACCTCTAGCGGCGTCGACCGGACCCTGTGCCCGGACGAGGCGACGTGCGCCAA
GAACTGCTTCGTCGAGGGCGTCAACTACACGAGCAGCGGGGTCGAGACGTCCGGCAGCTCCCTCACCC
TCCGCCAGTTCTTCAAGGGCTCCGACGGCGCCATCAACAGCGTCTCCCCGCGCGTCTACCTGCTCGGG
GGAGACGGCAACTATGTCGTGCTCAAGCTCCTCGGCCAGGAGCTGAGCTTCGACGTGGACGTATCGTC
GCTCCCCGTGCGGCGAGAACGCGGCCCTGTACCTGTCCGAGATGGACGCGACGGGAGGACGGAACGAGT
ACAACACGGGCGGGGCCGAGTACGGGTCGGGCTACTGTGACGCCCAGTGCCCCGTGATGAACTGGAAC
AACGGGACGCTCAACACGGGCCGGGTGGGCTCGTGCTGCAGCGAGATGGACATCCTCGAGGCCAACTC
CTTTGCCGAGGCCTTCACGCCGCACCCCTGCATCGGCAACTCTGTGCGACAAGAGCGGGTGCGGCTTCA
ACGCGTACGCGCGCGGTTACCACAACTACTGGGCCCCCGGCGGCACGCTCGACACGTCCCGGCCTTTC
ACCGTGATCACCCGCTTCGTCACCGACGACGGCACCCACCTCGGGCAAGCTCGCCCGCATCGAGCGCGT
CTACGTCCAGGACGGCAAGAAGGTGCCCAGCGCGGCGCCCGGGGGGACGTCATCACGGCCGACGGGT
GCACCTCCGCGCAGCCCTACGGCGGCCTTTCCGGCATGGGCGACGCCCTCGGCCGCGGGCATGGTCCT
GGCCCTGAGCATCTGGAACGACGCGTCCACCTACATGAACTGGCTCGACGCCGGCAGCAACGGCCCCT
GCAGCGACACCGAGGGTAACCCGTCCAACATCCTGGCCAACCACCCGGACGCCCACGTCGTGCTCTCC
AACATCCGCTGGGGCGACATCGGCTCCACCGTCGACACCGGCGATGGCGACAACAACGGCGGCGGCCCC
CAACCCGTCATCCACCACCACCGCTACCGCTACCACCACCTCCTCCGGCCCGGCCGAGCCTACCCAGA
CCCACTACGGCCAGTGTGGAGGGAAAGGATGGACGGGCCCTACCCGCTGCGAGACGCCCTACACCTGC
AAGTACCAGAACGACTGGTACTCGCAGTGCCTGTAG (SEQ ID NO: 9)
MGQKTLQGLVAAAQLAASVANAQQPGTFTPEVHPTLPTWKCTTSGGCVQQDTSVVLDWNYRWIHTRDG
SKSCITSSGVDRTLCPDEATCAKNCFVEGVNYTSSGVETSGSSLTLRQFFKGSDGAINSVSPRVYLLG
GDGNYVVLKLLGQELSFDVDVSSLPCGENAALYLSEMDATGGRNEYNTGGAEYGSGYCDAQCPVMNWN
NGTLNTGRVGSCCSEMDILEANSFAEAFTPHPCIGNSCDKSGCGFNAYARGYHNYWAPGGTLDTSRPF
TVITRFVTDDGTTSGKLARIERVYVQDGKKVPSAAPGGDVITADGCTSAQPYGGLSGMGDALGRGMVL
ALSIWNDASTYMNWLDAGSNGPCSDTEGNPSNILANHPDAHVVLSNIRWGDIGSTVDTGDGDNNGGGP
NPSSTTTATATTTSSGPAEPTQTHYGQCGGKGWTGPTRCETPYTCKYQNDWYSQCL

EXAMPLE 1

Wild-Type *M. thermophila* EG1b Gene Acquisition and Expression Vector Construction In this Example, production of an expression vector encoding the *M. thermophila* EG1b protein is described. cDNA coding the *M. thermophila* EG1b protein ("EG1b WT"; SEQ ID NO: 1) was amplified from a cDNA library prepared using methods known in the art. In some experiments, expression constructs were prepared in which the EG1b WT sequence was linked to its native signal peptide for secretion in *M. thermophila*. In additional experiments, an EG1b cDNA construct was cloned into an expression vector (including EG1b and the native signal peptide of EG1b), using standard methods known in the art.

Using standard methods known in the art, *S. cerevisiae* cells were transformed with the expression vector comprising EG1b and its native signal peptide. Clones with correct EG1b sequences were identified and activity was confirmed using pNPL assay (4-Nitrophenyl β-D-lactopyranoside; See, Example 3, infra).

In addition, mutagenized EG1b libraries were produced using methods known in the art. These libraries were used to select EG1b variants with improved characteristics, as described in the following Examples.

EXAMPLE 2

High Throughput Cultures for EG1b Variants

Mutagenized libraries of C1 EG1b cDNA, together with the Pm/I (NEB R0532) linearized pYTsec72 expression vector, were transformed into competent *S. cerevisiae* cells and plated on agar plates containing 20 g/L glucose, 6.7 g/L yeast nitrogen base, and 2 g/L amino acid drop-out mix minus uracil (USBio D9535). For each round of mutagenesis, an improved variant from the previous round was used as the backbone, making the process of improving the variants iterative. The Round 2 (Rd2) backbone (SEQ ID NOS:4 and 5) was a variant developed from the wt EG1b, while the Round 3 (Rd3) backbone (SEQ ID NOS:6 and 7) was a variant developed from the Rd2 backbone, and the Round 4 (Rd4) backbone (SEQ ID NOS:8 and 9) was a variant developed from the Rd3 backbone.

Single colonies of *S. cerevisiae* containing a plasmid with an EG1b variant were inoculated into 200 µl of synthetic defined media (pH6.0) containing 60 g/L glucose, 6.7 g/L yeast nitrogen base without amino acids (Sigma Y0626), 3.06 g/L sodium phosphate (monobasic), 0.80 g/L sodium phosphate (dibasic), and 2 g/L amino acid drop-out mix minus uracil (USBio D9535). Cells were grown overnight (at least 16 hours) in an incubator at 30° C. with shaking at 250 rpm. Then, 20µl of the overnight culture was diluted into 400 µl of synthetic defined expression media (pH6.0) containing 20 g/L glucose, 6.7 g/L yeast nitrogen base without amino acids (Sigma Y0626), 3.06 g/L sodium phosphate (monobasic), 0.80 g/L sodium phosphate (dibasic), and 2 g/L amino acid drop-out mix minus uracil (USBio D9535). This was incubated for 72 hours and allowed to grow at 37° C. while shaking at 250 rpm. Cultures were harvested by centrifugation (4000 rpm, 4° C., 15 minutes).

EXAMPLE 3

Assays

In this Example, assays used to determine EG1b activity and thermostability are described. While certain pH and temperature conditions are exemplified, additional pH and temperature conditions find use in other assays (e.g., pH 5 and/or 55° C.).

A. 4-Nitrophenyl β-D-Lactonvranoside (nNPL) Assay

In a total volume of 300 µl, 40 µl of *S. cerevisiae* supernatant containing secreted protein of an EG1b variant from Example 2 were added to 260 µl of 1.85 mM 4-nitrophenyl β-D-lactopyranoside (pNPL) in 100 mM sodium acetate (pH 4.5). The reaction was incubated for 20 hrs at 65° C. After 20 hrs, the reaction mixture was centrifuged for ~5 min at 4000 rpm, 4° C. and 25 µl was transferred to 175 µl of 1 M Na$_2$CO$_3$ in a flat-bottom clear plate to terminate the reaction. The plate was mixed gently, then centrifuged for 1 min, and absorbance was measured at λ=405 nm with a Spectramax M2 (Molecular Devices). When a wild type EG1b produced as described in Example 1was reacted with pNPL, the resulting mixture produced an absorbance of 0.40, while the negative control consisting of supernatant of *S. cerevisiae* containing empty vector produced an absorbance of 0.05 under the same reaction conditions. When the Rd2 and Rd3 backbones produced as described in Example 2 were reacted with pNPL, the resulting mixtures produced absorbances of 0.40 and 0.60respectively, while the negative control consisting of supernatant of *S. cerevisiae* containing empty vector produced an absorbance of 0.05 under the same reaction conditions. Active variants, with greater than or equal to 0.8-fold improvement over WT EG1b for pNPL, were selected for testing in AVICEL® cellolose (Sigma-Aldrich) and thermostability assays, as described below. In addition, the active variants obtained in Rd3 were tested for biomass activity. The Rd4 variants were directly assayed for AVICEL® and biomass activities without being tested in this pNPL assay first.

B. AVICEL® Cellulose Assay for Testing EG1b Variants

Activity on AVICEL® cellulose substrate (Sigma-Aldrich) was measured using a reaction mixture of 300 µl volume containing 30 mg of AVICEL® cellulose, 10 µl of supernatant produced as described in Example 2, a glass bead, and 230 µl of 196 mM sodium acetate, pH 4.5, Beta-glucosidase, which converts cellobiose to glucose was subsequently added and conversion of AVICEL® cellulose to glucose was measured using a GOPOD glucose assay (Megazyme). The reactions were incubated at 65° C. for 24 hours while shaking at 900 rpm, and then centrifuged. Then, 160 µl of the supernatant was filtered using the Millipore filter plate (Millipore MSRL N4050). Then, 10 µl of the filtrate was added to 190 µl of the GOPOD mixture (Megazyme, containing glucose oxidase, peroxidase and 4-amino-antipyrine) and incubated at room temperature for 30 minutes. The amount of glucose was measured spectrophotometrically at 510 nm with a Spectramax M2 (Molecular Devices). The amount of glucose generated was calculated based on the measured absorbance at 510 nm and using the standard curve when the standards were measured on the same plate. When wild type EG1b produced as described in Example 1 was used in the described reaction, approximately 0.4 g/l of glucose is produced. The range of operable pH for *S. cerevisiae*-produced EG1b was found to be between 3.5 and 7.0 with the range of operable temperature between 50 and 70° C., with optimal conditions at pH 5.0 and 60° C.

For Rd3 variants, the same assay was used, but 5 ul of the supernatant produced as described in Example 2 was added to the reaction mixture (i.e., instead of 10 ul), and 245 ul of 183mM sodium acetate, pH 4.5 was used (i.e., instead of 240 ul of 188 mM sodium acetate, pH 4.5), and the reactions were incubated at 65° C. for 72 hrs (i.e., instead of 30 hours).

For Rd4 variants, the same assay was used, but the reactions were incubated at 65° C. for 72 hrs, (i.e., instead of 30 hrs) and 5 ul of the filtrate was added to 195 ul of the GOPOD mixture (i.e., instead of 10 ul of the filtrate being added to 190 ul of the GOPOD mixture).

The results indicated that approximately 0.5 g/l glucose was produced by the Rd2 and Rd3 backbones and 1.2 g/l glucose was produced by the Rd4 backbone.

C. Thermostability Assay

To evaluate thermostability improvement of EG1b variants, 200 µl of the supernatant from Example 2 was added to 50 µl of 500 mM sodium acetate buffer (pH 4.5) in a 96-well plate and incubated at 70° C. for 2 hours. The reactions were cooled, centrifuged and tested for activity using pNPL assay of provided in this Example with the following exceptions: 150 µl of the supernatant-buffer mixture was added to 150 µl of 3.2 mM pNPL in 100 mM sodium acetate buffer (pH 4.5) and the reactions were incubated at 65° C. for 2 hours. Duplicate plates were created to calculate residual activity after the 2 hour thermal challenge where one copy of the plate was assayed without preincubation while the other copy was incubated at 70° C.

before assaying. Both copies were assayed using the same pNPL assay as described in this Example. Residual activity (in percentage) was calculated as a ratio of fluorescence after and before the thermal challenge multiplied by 100.

The beneficial mutations for activity and/or stability found in a set of variants are listed in Table 3-1. Variants with the most improved activity and thermostability were grown in shakeflask cultures and further tested for activity and thermostability.

TABLE 3-1

Beneficial EG1b Mutations for Cellulose Activity and/or Thermostability

| | Fold Improvement Over WT EG1b | |
|---|---|---|
| Mutation | Activity on AVICEL ® Cellulose | Thermostability |
| T43C | +++ | +++ |
| Q49R | +++ | + |
| F63I | ++++ | + |
| E66R | +++ | +++ |
| N126K | +++ | − |
| G137T | +++ | +++ |
| V143M | +++ | +++ |
| Q201L | ++++ | + |
| Q201M | +++ | + |
| N218S | +++ | ++ |
| K228F | +++ | − |
| S241K | +++ | +++ |
| S269L | +++ | ++ |
| M274V | +++ | + |
| S328Q | +++ | +++ |
| L342F | +++ | +++ |
| L342A | +++ | +++ |
| G350S | +++ | ++ |
| G434D | − | +++ |

− = less than or equal to control
+ = improvement up to 20% compared to control
++ = improvement of 20% to 49% greater compared to control
+++ = improvement of 50% to 100% greater compared to control
++++ = improvement over 100% compared to control

EXAMPLE 4

Additional Thermostability and Activity Testing

A single colony of *S. cerevisiae* containing a plasmid with an improved C1 EG1b variant described in Example 2 was inoculated into 3 ml of synthetic defined media (pH6.0) containing 60 g/L glucose, 6.7 g/L yeast nitrogen base without amino acids (Sigma Y0626), 3.06 g/L sodium phosphate (monobasic), 0.80 g/L sodium phosphate (dibasic), and 2 g/L amino acid drop-out mix minus uracil (USBio D9535). Cells were grown overnight (at least 16 hours) in an incubator at 30° C. with shaking at 250 rpm. Then, 0.5 ml of this culture was diluted into 50 ml of synthetic defined expression media (pH6.0) containing 20 g/L glucose, 6.7 g/L yeast nitrogen base without amino acids (Sigma Y0626), 3.06 g/L sodium phosphate (monobasic), 0.80 g/L sodium phosphate (dibasic), and 2 g/L amino acid drop-out mix minus uracil (USBio D9535). This was incubated for 72 hours and allowed to grow at 37° C., with shaking at 250 rpm. Cells were harvested by centrifugation (4000 rpm, 4° C., 15 minutes). The supernatant was decanted into a new tube and the activity of the WT EG1b was confirmed using the AVICEL® cellulose activity and thermostability assays, as described in Example 3, with the following exception—the *S. cerevisiae* supernatant containing secreted protein of a EG1b variant was from the shakeflask culture of Example 2, instead of Example 1.

The best variant was determined to have a single F63I mutation. This variant was used as the backbone for Rd2. The supernatant from the shakeflask culture of this Rd2 backbone exhibited 1,5-fold higher activity in the AVICEL® cellulose assay than that of wild type EG1b at 65° C., and pH 4.5. The thermostability of this variant was also improved significantly. After 24 hr incubation at 65° C. and p 4.5, this variant showed 53% residual activity while WT EG1b only had 9% residual activity.

TABLE 4-1

Rd3 Variants with Improved Activity and/or Thermostability

| | Fold Improvement Over Rd2 Backbone | |
|---|---|---|
| Substitution | Activity on AVICEL ® Cellulose | Thermostability |
| P34R | ++ | − |
| W39R | ++ | − |
| D85V | ++ | − |
| D397Y | +++ | +++ |
| T398M | ++ | − |
| G399C | ++ | +++ |
| D400R | ++ | + |
| G401D | ++ | − |
| N403D | ++ | +++ |
| N403M | ++ | +++ |
| N404L | ++ | +++ |
| G405C | ++ | − |
| G405Y | ++ | +++ |
| G405W | ++ | ++++ |
| G407R | ++ | +++ |
| P408E | ++ | − |
| P408G | ++ | − |
| N409W | ++ | ++ |
| S411A | ++ | ++ |
| S412Q | ++ | +++ |
| T413E | ++ | − |
| T413P | − | +++ |
| T414L | ++ | + |
| T415G | ++ | − |
| T417G | ++ | − |
| T417H | − | +++ |
| A418S | ++ | − |
| A418C | − | +++ |
| T419G | ++ | − |
| T420G | +++ | − |
| T420I | ++ | − |
| T420L | ++ | − |
| T420K | − | +++ |
| P425S | − | +++ |
| P425L | − | +++ |
| P428C | ++ | − |
| P428V | ++ | − |
| Y433F | +++ | +++ |
| Y433V | ++ | +++ |
| G434P | − | +++ |
| Q435R | ++ | + |
| Q435K | ++ | − |
| Q435G | − | +++ |
| G438A | ++ | +++ |
| K439P | − | +++ |
| G440D | ++ | +++ |
| G440R | ++ | + |
| G440T | ++ | ++ |
| G443E | ++ | − |
| G443S | − | +++ |
| P444Q | ++ | − |
| R446G | ++ | − |
| N457H | − | ++++ |
| L464Q | ++ | − |

− = less than or equal to control
+ = improvement up to 20% compared to control
++ = improvement of 20% to 49% greater compared to control
+++ = improvement of 50% to 100% greater compared to control
++++ = improvement over 100% compared to control

EXAMPLE 5

Biomass Assay

In this Example, a biomass activity assay used to assess Rd3 and Rd4 variants is described. In this assay, a reaction mixture volume of 300 ul was used, comprising 20 mg biomass (pre-treated wheat straw biomass substrate with 5% moisture), 50 ul of supernatant produced as described in Example 2, 100 ul of filtrate obtained from direct centrifugation of pre-treated wheat straw biomass, 50 ul of 900 mM sodium acetate, pH 4.5, and 90 ul sterilized water. In addition, beta-glucosidase, which converts cellobiose to glucose was subsequently added and conversion of AVICEL® to glucose was measured using a GOPOD assay. The reactions were incubated at 65° C. for 30 hours with shaking at 900 rpm and centrifuged at 400 rpm for 5 minutes. Then, 20 ul of filtrate was added to 180 ul of the GOPOD mixture (Megazyme, containing glucose oxidase, peroxidase, and 4-aminoantipyrine) and incubated at room temperature for 30 minutes. The amount of glucose was measured spectrophotometrically at 510 nm. The amount of glucose generated was calculated based on the measured absorbance at 510 nm and using the standard curve generated using standards measured on the same plate. When the Rd3 backbone produced as described in Example 2 was used, approximately 0.2 g/l glucose was produced.

For testing of Rd4 variants, the same method was used, but with the following exceptions. First, 10 ul of the supernatant produced as described in Example 2 was added to the reaction mixture, instead of 50 ul and the reactions were incubated at 65° C. for 72 hrs (i.e., instead of 30 hrs). When the Rd4 backbone was tested, approximately 0.15 g/l glucose was produced.

The beneficial substitutions for activity obtained in Rd3 are provided in the Table below. Variants with the most improved activity on AVICEL® cellulose, biomass, and/or thermostability were grown and further tested.

In addition, it was determined that all of the improved variants obtained in Rd4 had an 1867 deletion in the vector, which resulted in higher expression of EG1b.

TABLE 5-1

Fold Improvement Over Rd3 Backbone

| Substitution | Activity on AVICEL ® Cellulose | Activity on Biomass |
|---|---|---|
| T5L | +++ | + |
| T5N | ++ | + |
| L6I | ++ | + |
| L6K | ++ | + |
| L6M | ++ | + |
| L6S | ++ | + |
| L6T | ++ | + |
| Q7C | ++ | + |
| Q7S | ++ | + |
| Q7T | ++ | + |
| Q7V | ++ | ++ |
| Q7Y | ++ | + |
| G8D | +++ | ++ |
| G8H | +++ | + |
| G8I | +++ | ++ |
| G8L | +++ | ++ |
| G8N | +++ | ++ |
| G8Q | +++ | + |
| G8R | ++ | + |
| G8S | +++ | − |
| G8T | +++ | + |
| G8V | ++ | ++ |
| G8Y | +++ | ++ |
| L9F | ++ | + |
| V10M | +++ | + |
| A11C | ++ | ++ |
| A11G | ++ | ++ |
| A11I | +++ | ++ |
| A11L | ++ | + |
| A11S | ++ | ++ |
| A11T | +++ | ++ |
| A11V | ++ | ++ |
| A11Y | ++ | ++ |
| A12L | ++ | + |
| A12V | ++ | ++ |
| A13C | ++ | ++ |
| A13I | +++ | ++ |
| A13L | ++ | + |
| A13M | ++ | + |
| A13T | ++ | + |
| A13W | ++ | + |
| A14I | +++ | ++ |
| A14L | ++ | ++ |
| A14M | ++ | ++ |
| A14Q | +++ | ++ |
| A14T | ++ | + |
| A14V | ++ | + |
| L15F | +++ | + |
| A16H | ++ | ++ |
| A16I | +++ | ++ |
| A16N | ++ | ++ |
| A16T | ++ | ++ |
| A17C | ++ | ++ |
| A17F | +++ | ++ |
| A17H | ++ | ++ |
| A17N | +++ | ++ |
| A17S | ++ | + |
| A17V | ++ | ++ |
| A17W | ++ | ++ |
| A17Y | +++ | ++ |
| S18C | ++ | + |
| S18E | ++ | ++ |
| S18G | ++ | ++ |
| S18I | ++ | + |
| S18M | ++ | + |
| S18P | ++ | ++ |
| S18Q | ++ | ++ |
| S18Y | ++ | + |
| V19I | ++ | ++ |
| V19L | ++ | − |
| V19T | +++ | ++ |
| A20I | ++ | ++ |
| N21H | ++ | ++ |
| N21K | +++ | ++ |
| A22S | +++ | ++ |
| T38A | +++ | ++ |
| S75P | ++ | − |
| D282G | +++ | ++ |
| G434D | ++ | − |

− = less than or equal to control
+ = improvement up to 20% compared to control
++ = improvement of 20% to 49% greater compared to control
+++ = improvement of 50% to 100% greater compared to control
++++ = improvement over 100% compared to control Beneficial substitutions for both AVICEL® cellulose and biomass activity included N403DM, T419G, P425L, N404L, P428V, L340M, D400R, A418S, G440D, N346D, and G401D. Substitutions that were beneficial in the AVICEL® cellulose assay, but neutral in the biomass activity assay included Q435G and R446G. The substitution T417G was found to be a beneficial substitution in the biomass assay, but neutral in the AVICEL® cellulose assay.

EXAMPLE 6

Additional Testing

A single colony of *S. cerevisiae* containing a plasmid with an improved C1 EG1b variant identified as described in Example 3 was inoculated into 3 ml of synthetic defined media (pH6.0) containing 60 g/L glucose, 6.7 g/L yeast nitrogen base without amino acids (Sigma Y0626), 3.06 g/L sodium phosphate (monobasic), 0.80 g/L sodium phosphate (dibasic), and 2 g/L amino acid drop-out mix minus uracil (USBio D9535). Cells were grown overnight (at least 16 hours) in an incubator at 30° C. with shaking at 250 rpm.

Then, 0.5 ml of this culture was diluted into 50 ml of synthetic defined expression media (pH6.0) containing 20 g/L glucose, 6.7 g/L yeast nitrogen base without amino acids (Sigma Y0626), 3.06 g/L sodium phosphate (monobasic), 0.80 g/L sodium phosphate (dibasic), and 2 g/L amino acid drop-out mix minus uracil (USBio D9535). In Rd 2, the inoculated culture was then incubated for 48hours and allowed to grow at 37° C. while shaking at 250 rpm. In Rd3 and 4, the inoculated culture was incubated for 64 hours and allowed to grow at 30° C. while shaking at 250 rpm. Cells were harvested by centrifugation (4000 rpm, 4° C., 15 minutes). The supernatant was decanted into a new tube and the activity of the EG1b variant were confirmed using the AVICEL® cellulose activity and thermostability assays (Examples 3B and C respectively) with the following exception: the *S. cerevisiae* supernatant containing secreted protein of a C1 EG1b variant is from the shakeflask culture of Example 4 instead of Example 2.

As indicated above, the best hit from Round 2 of evolution became the Rd3 backbone (SEQ ID NOS:6 and 7), with mutations E66R/Q201M/N218S/K228F/M274V/G350T over the Rd 2backbone. The supernatant from the shakeflask culture of the Rd3 backbone showed an improvement of more than 50% in the AVICEL® cellulose assay, as compared to the Rd2 backbone at 65° C., and pH 4.5. The thermostability of the Rd3 backbone was also slightly improved as compared to the Rd2backbone. After 2 hr incubation at 70° C., and pH 4.5, the Rd3 backbone showed 50% residual activity while Rd2 backbone had 40% residual activity.

The best hit from Round 3 of evolution became the Rd4 backbone, with a single mutation (A14Q) over the Rd3 backbone. The supernatant from the shakeflask culture of the Rd4 backbone showed 1.5-fold higher activity in both the AVICEL® cellulose and pretreated wheat straw biomass assays than that of the Rd3 backbone at 65° C., and pH 4.5.

While some particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of the present invention.

---

We claim:

1. A variant endoglucanase or enzymatically active fragment thereof comprising
   (a) an amino acid sequence at least 80% identical to the wild-type endoglucanase amino acid sequence of SEQ ID NO:3; and
   (b) an amino acid substitution introducing an amino acid other than phenylalanine at position 63,
   wherein the residue positions are numbered with reference to SEQ ID NO:2.

2. The variant endoglucanase of claim 1, wherein the variant comprises one or more amino acid substitutions selected from P34, T38, W39, T43, Q49, E66, S75, D85, N126, G137, V143, Q201, N218, K228, S241, S269, M274, D282, S328, L342, L342, G350, D397, T398, G399, D400, G401, N403, N403, N404, G405, G407, P408, P408, N409, S411, S412, T413, T414, T415, T417, T417, A418, T419, T420, P425, P428, Y433, G434, Q435, Q435, G438, K439, G440, G443, P444, R446, N457, and L464, wherein the residues are numbered with reference to SEQ ID NO:2.

3. The variant endoglucanase of claim 1, wherein the variant comprises one or more amino acid substitutions selected from 34R, 38A, 39R, 43C, 49R, 66R, 75P, 85V, 126K, 137T, 143M, 201L, 201M, 218S, 228F, 241K, 269L, 274V, 282G, 328Q, 342F, 342A, 350S, 397Y, 398M, 399C, 400R, 401D, 403D, 403M, 404L, 405C, 405Y, 405W, 407R, 408E, 408G, 409W, 411A, 412Q, 413E, 413P, 414L, 415G, 417G, 417H, 418C, 418S, 419G, 420G, 420I, 420L, 420K, 425S, 425L, 428C, 428V, 433F, 433V, 434D, 434P, 435G, 435K, 435R, 438A, 439P, 440D, 440R, 440T, 443E, 443S, 444Q, 446G, 457H, and 464Q, wherein the residues are numbered with reference to SEQ ID NO:2.

4. The variant endoglucanase of claim 1, wherein the variant comprises at least one substitution selected from N403D/M, T419G, P425L, N404L, P428V, L340M, D400R, A418S, G440D, N346D, G401D, Q435G, R446G, and T417G, wherein the residues are numbered with reference to SEQ ID NO:2.

5. A variant endoglucanase comprising an enzymatically active endoglucanase amino acid sequence wherein an amino acid substitution introduces an amino acid other than phenylalanine at position 63 and having at least 80% identity to an amino acid sequence set forth in any of SEQ IDs NOs:5, 7 or 9.

6. The variant endoglucanase of claim 1, wherein the variant is a variant of the *Myceliophthora thermophila* EG 1b amino acid sequence of SEQ ID NO:2.

7. The variant endoglucanase of claim 1, wherein the variant has increased thermoactivity at pH of about 4-5 and a temperature of about 65° C. in comparison to the wild-type endoglucanase 1b set forth in SEQ ID NO:3.

8. The variant endoglucanase of claim 1, wherein the variant has increased activity on cellulose in comparison to the wild-type endoglucanase 1b set forth in SEQ ID NO:3.

9. An enzyme composition comprising the variant endoglucanase of claim 1.

10. The enzyme composition of claim 9, further comprising at least one additional enzyme.

11. The enzyme composition of claim 9, further comprising one or more enzyme(s) selected from other endoglucanases (EG), β-glucosidases (BGL), Type 1 cellobiohydrolases (CBH1), and/or Type 2 cellobiohydrolases (CBH2).

12. A method for producing at least one fermentable sugar from a biomass substrate, comprising contacting the biomass substrate with the enzyme composition according to claim 9, under culture conditions whereby fermentable sugars are produced.

13. The method of claim 12, wherein the enzyme composition comprises at least one enzyme selected from other endoglucanases (EG), β-glucosidases (BGL), Type 1 cellobiohydrolases (CBH1), and Type 2 cellobiohydrolases (CBH2).

* * * * *